US012214092B2

(12) United States Patent
Church et al.

(10) Patent No.: US 12,214,092 B2
(45) Date of Patent: Feb. 4, 2025

(54) SYSTEMS AND METHODS FOR TREATING BIOLOGICAL FLUIDS

(71) Applicant: Cerus Corporation, Concord, CA (US)

(72) Inventors: Daniel Church, Danville, CA (US); Peter Bringmann, Concord, CA (US); Grace Castro, Martinez, CA (US); Thea Lu, Pleasant Hill, CA (US); Shelby Reinhardt, San Francisco, CA (US); Felicia Santa Maria, Bay Point, CA (US); Adonis Stassinopoulos, Del Mar, CA (US)

(73) Assignee: Cerus Corporation, Concord, CA (US)

( * ) Notice: Subject to any disclaimer, the term of this patent is extended or adjusted under 35 U.S.C. 154(b) by 221 days.

(21) Appl. No.: 18/084,344

(22) Filed: Dec. 19, 2022

(65) Prior Publication Data
US 2023/0226232 A1    Jul. 20, 2023

Related U.S. Application Data

(62) Division of application No. 16/236,193, filed on Dec. 28, 2018, now Pat. No. 11,554,185.
(Continued)

(51) Int. Cl.
| | |
|---|---|
| *A61L 2/00* | (2006.01) |
| *A01N 1/02* | (2006.01) |
| *A61K 31/37* | (2006.01) |
| *A61K 41/17* | (2020.01) |
| *A61L 2/26* | (2006.01) |
| *A61M 1/36* | (2006.01) |
| *B01J 19/12* | (2006.01) |

(Continued)

(52) U.S. Cl.
CPC .......... *A61L 2/0047* (2013.01); *A01N 1/0215* (2013.01); *A01N 1/0294* (2013.01); *A61K 31/37* (2013.01); *A61K 41/17* (2020.01); *A61L 2/0076* (2013.01); *A61L 2/26* (2013.01); *A61M 1/3683* (2014.02); *B01J 19/123* (2013.01); *H01L 25/0753* (2013.01); *A61L 2/24* (2013.01); *A61L 2202/11* (2013.01); *A61L 2202/122* (2013.01); *A61L 2202/14* (2013.01); *A61L 2202/22* (2013.01); *A61M 2202/0415* (2013.01); *A61M 2202/0427* (2013.01)

(58) Field of Classification Search
CPC ............. A61L 2202/22; A61L 2202/11; A61L 2/0076; A61L 2/0047; A61M 1/3683
See application file for complete search history.

(56) References Cited

U.S. PATENT DOCUMENTS

| | | |
|---|---|---|
| 5,167,656 A | 12/1992 | Lynn |
| 5,221,608 A | 6/1993 | Cimino et al. |

(Continued)

FOREIGN PATENT DOCUMENTS

| | | |
|---|---|---|
| CN | 1284886 A | 2/2001 |
| CN | 1450916 A | 10/2003 |

(Continued)

OTHER PUBLICATIONS

Alhumaidan, H. et al. (2012). "Current Status of Additive Solution for Platelets," J. Clin Apheresis 27:93-98.
(Continued)

*Primary Examiner* — Sean E Conley
(74) *Attorney, Agent, or Firm* — MORRISON & FOERSTER LLP

(57) ABSTRACT

Provided are systems and methods for treating a biological fluid, e.g., to inactivate pathogens.

57 Claims, 15 Drawing Sheets

Related U.S. Application Data

(60) Provisional application No. 62/612,314, filed on Dec. 29, 2017.

(51) Int. Cl.
*H01L 25/075* (2006.01)
*A61L 2/24* (2006.01)

(56) References Cited

U.S. PATENT DOCUMENTS

| | | | |
|---|---|---|---|
| 5,288,605 A | 2/1994 | Lin et al. | |
| 5,399,719 A | 3/1995 | Wollowitz et al. | |
| 5,405,343 A | 4/1995 | Mohr | |
| 5,418,130 A | 5/1995 | Platz et al. | |
| 5,459,030 A | 10/1995 | Lin et al. | |
| 5,482,828 A | 1/1996 | Lin et al. | |
| 5,556,958 A | 9/1996 | Carroll | |
| 5,556,993 A | 9/1996 | Wollowitz | |
| 5,559,250 A | 9/1996 | Cook | |
| 5,571,082 A | 11/1996 | Bashikirov | |
| 5,578,736 A | 11/1996 | Wollowitz | |
| 5,585,503 A | 12/1996 | Wollowitz | |
| 5,589,462 A | 12/1996 | Patat | |
| 5,593,823 A | 1/1997 | Wollowitz et al. | |
| 5,618,662 A | 4/1997 | Lin et al. | |
| 5,625,079 A | 4/1997 | Wollowitz et al. | |
| 5,654,443 A | 8/1997 | Wollowitz | |
| 5,691,132 A | 11/1997 | Wollowitz et al. | |
| 5,709,991 A | 1/1998 | Lin et al. | |
| 5,712,085 A | 1/1998 | Wollowitz | |
| 5,871,900 A | 2/1999 | Wollowitz | |
| 5,908,742 A | 6/1999 | Lin et al. | |
| 5,965,349 A | 10/1999 | Lin | |
| 5,972,593 A | 10/1999 | Wollowitz | |
| 6,004,741 A | 12/1999 | Wollowitz | |
| 6,004,742 A | 12/1999 | Wollowitz | |
| 6,017,691 A | 1/2000 | Wollowitz et al. | |
| 6,093,725 A | 7/2000 | Cook et al. | |
| 6,133,460 A | 10/2000 | Wollowitz et al. | |
| 6,143,490 A | 11/2000 | Cook et al. | |
| 6,171,777 B1 | 1/2001 | Cook | |
| 6,177,441 B1 | 1/2001 | Cook et al. | |
| 6,194,139 B1 | 2/2001 | Wollowitz | |
| 6,218,100 B1 | 4/2001 | Wollowitz | |
| 6,251,580 B1 | 6/2001 | Lin | |
| 6,270,952 B1 | 8/2001 | Cook et al. | |
| 6,277,337 B1 | 8/2001 | Goodrich, Jr. et al. | |
| 6,281,225 B1 | 8/2001 | Hearst et al. | |
| 6,410,219 B1 | 6/2002 | Cook et al. | |
| 6,420,570 B1 | 7/2002 | Wollowitz | |
| 6,433,343 B1 | 8/2002 | Cimino et al. | |
| 6,455,286 B1 | 9/2002 | Wollowitz | |
| 6,469,052 B2 | 10/2002 | Wollowitz | |
| 6,503,699 B1 | 1/2003 | Wollowitz et al. | |
| 6,514,987 B1 | 2/2003 | Cook et al. | |
| 6,544,727 B1 | 4/2003 | Hei | |
| 6,548,242 B2 | 4/2003 | Horowitz et al. | |
| 6,565,802 B1 | 5/2003 | Hanley | |
| 6,586,749 B2 | 7/2003 | Cimino | |
| 6,686,480 B2 | 2/2004 | Wollowitz | |
| 6,709,810 B2 | 3/2004 | Cook | |
| 6,843,961 B2 | 1/2005 | Hlavinka et al. | |
| 6,949,753 B2 | 9/2005 | Cimino | |
| 6,951,713 B2 | 10/2005 | Hei et al. | |
| 6,986,867 B2 | 1/2006 | Hanley et al. | |
| 7,025,877 B1 | 4/2006 | De | |
| 7,037,642 B2 | 5/2006 | Hei et al. | |
| 7,105,093 B2 | 9/2006 | De | |
| 7,293,985 B2 | 11/2007 | Cook | |
| 7,425,304 B2 | 9/2008 | De | |
| 7,433,030 B2 | 10/2008 | Waldo et al. | |
| 7,459,695 B2 | 12/2008 | Hanley et al. | |
| 7,601,298 B2 | 10/2009 | Waldo et al. | |
| 7,611,831 B2 | 11/2009 | Hei | |
| 7,655,392 B2 | 2/2010 | Stassinopoulos | |
| 7,829,867 B2 | 11/2010 | Hlavinka et al. | |
| 8,296,071 B2 | 10/2012 | Edrich et al. | |
| 8,778,263 B2 | 7/2014 | Walker et al. | |
| 8,900,805 B2 | 12/2014 | Mufti et al. | |
| 9,259,525 B2 | 2/2016 | Hei | |
| 9,320,817 B2 | 4/2016 | Walker et al. | |
| 9,713,627 B2 | 7/2017 | Mufti | |
| 10,357,516 B2 | 7/2019 | Mufti | |
| 10,799,533 B2 | 10/2020 | Corash | |
| 10,842,818 B2 | 11/2020 | Vermeij | |
| 11,096,963 B2 | 8/2021 | Corash et al. | |
| 11,554,185 B2 | 1/2023 | Church et al. | |
| 2001/0009756 A1 | 7/2001 | Hei | |
| 2001/0018179 A1 | 8/2001 | Hei | |
| 2002/0006393 A1 | 1/2002 | Wollowitz | |
| 2002/0028432 A1 | 3/2002 | Cook | |
| 2002/0042043 A1 | 4/2002 | Stassinopoulos | |
| 2002/0115585 A1 | 8/2002 | Hei | |
| 2002/0192632 A1 | 12/2002 | Hei | |
| 2003/0035751 A1 | 2/2003 | Hanley et al. | |
| 2003/0062483 A1 | 4/2003 | Cimino | |
| 2003/0105339 A1 | 6/2003 | Wollowitz | |
| 2003/0113704 A1 | 6/2003 | Stassinopoulos | |
| 2003/0146162 A1 | 8/2003 | Metzel et al. | |
| 2003/0185804 A1 | 10/2003 | Wollowitz et al. | |
| 2003/0207247 A1 | 11/2003 | Stassinopoulos et al. | |
| 2003/0219354 A1 | 11/2003 | Hlavinka et al. | |
| 2004/0021809 A1 | 2/2004 | Sumiyoshi et al. | |
| 2004/0029897 A1 | 2/2004 | Cook | |
| 2004/0088189 A1 | 5/2004 | Veome et al. | |
| 2004/0180321 A1 | 9/2004 | Cook | |
| 2004/0185544 A9 | 9/2004 | Hei | |
| 2004/0185553 A9 | 9/2004 | Hei | |
| 2004/0197343 A1 | 10/2004 | Dubensky et al. | |
| 2004/0228877 A1 | 11/2004 | Dubensky et al. | |
| 2005/0142542 A1 | 6/2005 | Hei | |
| 2005/0175625 A1 | 8/2005 | Jaffee et al. | |
| 2005/0202395 A1 | 9/2005 | Edrich et al. | |
| 2005/0249748 A1 | 11/2005 | Dubensky et al. | |
| 2005/0281783 A1 | 12/2005 | Kinch et al. | |
| 2006/0093999 A1 | 5/2006 | Hei | |
| 2006/0115466 A1 | 6/2006 | Stassinopoulos | |
| 2006/0197031 A1 | 9/2006 | De et al. | |
| 2007/0031457 A1 | 2/2007 | Dubensky et al. | |
| 2007/0190029 A1 | 8/2007 | Pardoll et al. | |
| 2007/0190063 A1 | 8/2007 | Bahjat et al. | |
| 2007/0207170 A1 | 9/2007 | Dubensky et al. | |
| 2007/0207171 A1 | 9/2007 | Dubensky et al. | |
| 2007/0235376 A1 | 10/2007 | Daniel | |
| 2010/0133160 A1 | 6/2010 | Hei | |
| 2011/0286987 A1 | 11/2011 | Mufti | |
| 2013/0320299 A1 | 12/2013 | Li | |
| 2013/0323128 A1 | 12/2013 | Owen et al. | |
| 2014/0303547 A1 | 10/2014 | Loupis et al. | |
| 2014/0346370 A1 | 11/2014 | Dobrinsky et al. | |
| 2014/0353519 A1 | 12/2014 | Wang | |
| 2015/0157665 A1 | 6/2015 | Mufti | |
| 2016/0354533 A1 | 12/2016 | Hei | |
| 2017/0014538 A1 | 1/2017 | Rantala | |
| 2017/0027986 A1 | 2/2017 | Corash et al. | |
| 2017/0050046 A1 | 2/2017 | Walder et al. | |
| 2017/0202882 A1 | 7/2017 | Vermeij | |
| 2017/0252474 A1 | 9/2017 | Thompson et al. | |
| 2017/0304363 A1 | 10/2017 | Corash | |
| 2018/0008639 A1 | 1/2018 | Mufti | |
| 2018/0113066 A1 | 4/2018 | Freitag et al. | |
| 2018/0147306 A1 | 5/2018 | Crawley et al. | |
| 2018/0184985 A1 | 7/2018 | Håkansson et al. | |
| 2018/0185484 A1 | 7/2018 | Greenman et al. | |
| 2018/0289873 A1 | 10/2018 | David | |
| 2018/0318348 A1 | 11/2018 | Corash et al. | |
| 2019/0085289 A1 | 3/2019 | Greenman | |
| 2019/0099543 A1 | 4/2019 | Sasaki | |
| 2019/0100718 A1 | 4/2019 | Estes et al. | |
| 2019/0209718 A1 | 7/2019 | Church | |
| 2019/0321407 A1 | 10/2019 | Erickson et al. | |
| 2019/0369087 A1 | 12/2019 | North et al. | |
| 2020/0078406 A1 | 3/2020 | Weiner et al. | |
| 2020/0397931 A1 | 12/2020 | Church et al. | |

(56) References Cited

U.S. PATENT DOCUMENTS

| | | | |
|---|---|---|---|
| 2020/0397935 | A1 | 12/2020 | Church et al. |
| 2020/0405891 | A1 | 12/2020 | Church et al. |
| 2021/0038802 | A1 | 2/2021 | Madsen |
| 2021/0052804 | A1 | 2/2021 | Madsen |
| 2021/0187020 | A1 | 6/2021 | Corash et al. |
| 2021/0260114 | A1 | 8/2021 | Corash et al. |
| 2021/0322479 | A1 | 10/2021 | Vermeij |
| 2022/0031917 | A1 | 2/2022 | Cahyadi et al. |
| 2022/0118136 | A1 | 4/2022 | Church et al. |

FOREIGN PATENT DOCUMENTS

| | | | |
|---|---|---|---|
| CN | 203017432 | U | 6/2013 |
| CN | 106421864 | A | 2/2017 |
| CN | 107075478 | A | 8/2017 |
| EP | 1181061 | B1 | 8/2006 |
| EP | 3009946 | A1 | 4/2016 |
| WO | 199300005 | A1 | 1/1993 |
| WO | 199317553 | A1 | 9/1993 |
| WO | 199403054 | A1 | 2/1994 |
| WO | 199420090 | A1 | 9/1994 |
| WO | 199427433 | A1 | 12/1994 |
| WO | 199428120 | A1 | 12/1994 |
| WO | 199500141 | A1 | 1/1995 |
| WO | 199512973 | A1 | 5/1995 |
| WO | 199519705 | A1 | 7/1995 |
| WO | 199608965 | A1 | 3/1996 |
| WO | 199614737 | A1 | 5/1996 |
| WO | 199614739 | A1 | 5/1996 |
| WO | 199614740 | A1 | 5/1996 |
| WO | 199639815 | A1 | 12/1996 |
| WO | 199639818 | A1 | 12/1996 |
| WO | 199639820 | A1 | 12/1996 |
| WO | 199640857 | A1 | 12/1996 |
| WO | 199721346 | A1 | 6/1997 |
| WO | 199737536 | A1 | 10/1997 |
| WO | 199818908 | A1 | 5/1998 |
| WO | 199830327 | A1 | 7/1998 |
| WO | 199830545 | A1 | 7/1998 |
| WO | 199903976 | A2 | 1/1999 |
| WO | 199903976 | A3 | 5/1999 |
| WO | 199926476 | A1 | 6/1999 |
| WO | 199934839 | A1 | 7/1999 |
| WO | 199934914 | A1 | 7/1999 |
| WO | 199934915 | A1 | 7/1999 |
| WO | 199959645 | A1 | 11/1999 |
| WO | 199963981 | A2 | 12/1999 |
| WO | 199963981 | A3 | 4/2000 |
| WO | 200074731 | A1 | 12/2000 |
| WO | 200191775 | A2 | 12/2001 |
| WO | 200191775 | A3 | 6/2002 |
| WO | 2003047650 | A2 | 6/2003 |
| WO | 2003049784 | A2 | 6/2003 |
| WO | 2003049784 | A3 | 6/2003 |
| WO | 2003061379 | A2 | 7/2003 |
| WO | 2003065787 | A2 | 8/2003 |
| WO | 2003078023 | A1 | 9/2003 |
| WO | 2003061379 | A3 | 10/2003 |
| WO | 2003090794 | A1 | 11/2003 |
| WO | 2003065787 | A3 | 12/2003 |
| WO | 2003047650 | A3 | 2/2004 |
| WO | 2004033081 | A2 | 4/2004 |
| WO | 2004033081 | A3 | 6/2004 |
| WO | 2004049914 | A2 | 6/2004 |
| WO | 2004050029 | A2 | 6/2004 |
| WO | 2004050848 | A2 | 6/2004 |
| WO | 2004050897 | A2 | 6/2004 |
| WO | 2004050897 | A3 | 8/2004 |
| WO | 2004050029 | A3 | 10/2004 |
| WO | 2004084936 | A2 | 10/2004 |
| WO | 2004050848 | A3 | 12/2004 |
| WO | 2004110481 | A2 | 12/2004 |
| WO | 2004049914 | A3 | 2/2005 |
| WO | 2005009463 | A2 | 2/2005 |
| WO | 2004110481 | A3 | 3/2005 |
| WO | 2005037233 | A2 | 4/2005 |
| WO | 2004084936 | A3 | 6/2005 |
| WO | 2005009463 | A3 | 6/2005 |
| WO | 2005067460 | A2 | 7/2005 |
| WO | 2005071088 | A2 | 8/2005 |
| WO | 2005092372 | A2 | 10/2005 |
| WO | 2005071088 | A3 | 11/2005 |
| WO | 2005037233 | A3 | 1/2006 |
| WO | 2006021314 | A2 | 3/2006 |
| WO | 2006050328 | A1 | 5/2006 |
| WO | 2005092372 | A3 | 6/2006 |
| WO | 2005067460 | A3 | 10/2006 |
| WO | 2007022511 | A2 | 2/2007 |
| WO | 2007022520 | A2 | 2/2007 |
| WO | 2007022520 | A3 | 5/2007 |
| WO | 2007022511 | A3 | 9/2007 |
| WO | 2007103225 | A2 | 9/2007 |
| WO | 2007103261 | A2 | 9/2007 |
| WO | 2007117371 | A2 | 10/2007 |
| WO | 2007103225 | A3 | 5/2008 |
| WO | 2007103261 | A3 | 12/2008 |
| WO | 2007117371 | A3 | 12/2008 |
| WO | 2008156813 | A1 | 12/2008 |
| WO | 2009126786 | A2 | 10/2009 |
| WO | 2009126786 | A3 | 7/2010 |
| WO | 2011120172 | A1 | 10/2011 |
| WO | 2012018484 | A2 | 2/2012 |
| WO | 2012018484 | A3 | 4/2012 |
| WO | 2012071135 | A2 | 5/2012 |
| WO | 2012071135 | A3 | 8/2012 |
| WO | 2014051882 | A1 | 4/2014 |
| WO | 2014051906 | A1 | 4/2014 |
| WO | 2015168783 | A1 | 11/2015 |
| WO | 2016014854 | A1 | 1/2016 |
| WO | 2016057965 | A1 | 4/2016 |
| WO | 2016115535 | A1 | 7/2016 |
| WO | 2016149055 | A2 | 9/2016 |
| WO | 2016149055 | A3 | 12/2016 |
| WO | 2016210374 | A1 | 12/2016 |
| WO | 2017009534 | A1 | 1/2017 |
| WO | 2017062260 | A2 | 4/2017 |
| WO | 2017070619 | A1 | 4/2017 |
| WO | 2017062260 | A3 | 5/2017 |
| WO | 2017120545 | A2 | 7/2017 |
| WO | 2017120545 | A3 | 8/2017 |
| WO | 2018119462 | A1 | 6/2018 |
| WO | 2018125994 | A1 | 7/2018 |
| WO | 2018161020 | A1 | 9/2018 |
| WO | 2019060610 | A1 | 3/2019 |
| WO | 2020061537 | A1 | 3/2020 |
| WO | 2020263745 | A1 | 12/2020 |
| WO | 2020263759 | A2 | 12/2020 |
| WO | 2020264421 | A1 | 12/2020 |
| WO | 2020263759 | A3 | 1/2021 |
| WO | 2022087580 | A1 | 4/2022 |

OTHER PUBLICATIONS

International Preliminary Report on Patentability, issued Dec. 28, 2021, for PCT Application No. PCT/US2020/038950, filed Jun. 22, 2020, 9 pages.
International Preliminary Report on Patentability, issued Dec. 28, 2021, for PCT Application No. PCT/US2020/039011, filed Jun. 22, 2020, 13 pages.
International Preliminary Report on Patentability, issued Dec. 28, 2021, for PCT Application No. PCT/US2020/039984, filed Jun. 26, 2020, 8 pages.
International Preliminary Report on Patentability, issued Jun. 30, 2020, for PCT Application No. PCT/US2018/068048, 11 pages.
International Search Report and Written Opinion, mailed Aug. 19, 2002, for PCT Application No. PCT/US2020/038950, filed Jun. 22, 2020, 16 pages.
International Search Report and Written Opinion, mailed Dec. 23, 2020, for PCT Application No. PCT/US2020/039011, filed Jun. 22, 2020, 18 pages.
International Search Report and Written Opinion, mailed Jan. 17, 2022, for PCT Application No. PCT/US2021/0071920, filed Oct. 18, 2021, 14 pages.

(56) References Cited

OTHER PUBLICATIONS

International Search Report and Written Opinion, mailed May 3, 2019, for PCT Application No. PCT/US2018/068048, filed on Dec. 28, 2018 18 pages.

International Search Report and Written Opinion, mailed Sep. 29, 2020, for PCT Application No. PCT/US2020/039984, filed Jun. 26, 2020, 14 pages.

Irsch, J. et al. (2011, e-pub. Jan. 27, 2011). "Pathogen Inactivation of Platelet and Plasma Blood Components for Transfusion Using the Intercept Blood System™," Transfus. Med. Hemother. 38:19-31.

Prodouz, K.N. et al. (1992). "Effects of Two Viral Inactivation Methods on Platelets: Laser-UV Radiation and Merocyanie 540-Mediated Photoinactivation," Blood Cells 18(1): 101-116.

Prowse, C.V. (Apr. 2013, e-pub. Nov. 8, 2012). "Component Pathogen Inactivation: A Critical Review," Vox Sanguinis, 104(3):183-199,.

Reikvam, H. et al. (2010). "The Mirasol@ Pathogen Reduction Technology System and Quality of Platelets Stored in Platelet Additive Solution," Blood Transfus. 8:186-192.

Ringwald, J. et al. (Apr. 2006). "The New Generation of Platelet Additivie Solution for Storage at 22° C: Development and Current Experience," Transfusion Medicine Reviews, 20(2):158-164.

Schlenke, P. (2014, e-pub. Jul. 21, 2014). "Pathogen Inactivation Technologies for Cellular Blood Components: an Update," Transfus. Med. Hemother. 41:309-325.

Schlenke, P. et al. (2008). "Photochemical Treatment Of Plasma With Amotosalen and UVA Light: Process Validation In Three European Blood Centers," Transfusion 48:697-705, 9 pages.

Seltsam, A. et al. (2011, e-pub. Jan. 22, 2011). "UVC Irraditation For Pathogen Reduction of Platelet Concentrates and Plasma," Transfusion Medicine and Hemotherapy 38:43-54.

Sofer, G. (Aug. 2002). "Virus Inactivation In The 1990s—and Into the 21st Century: Part 2, Red Blood Cells and Platelets," BioPharm pp. 42-49.

U.S. Appl. No. 09/238,355, Greenman, W. et al., filed Jan. 27, 1999. (Copy not submitted herewith pursuant to the waiver of 37 C.F.R. § 1.98(a)(2)(iii) issued by the Office on Sep. 21, 2004.).

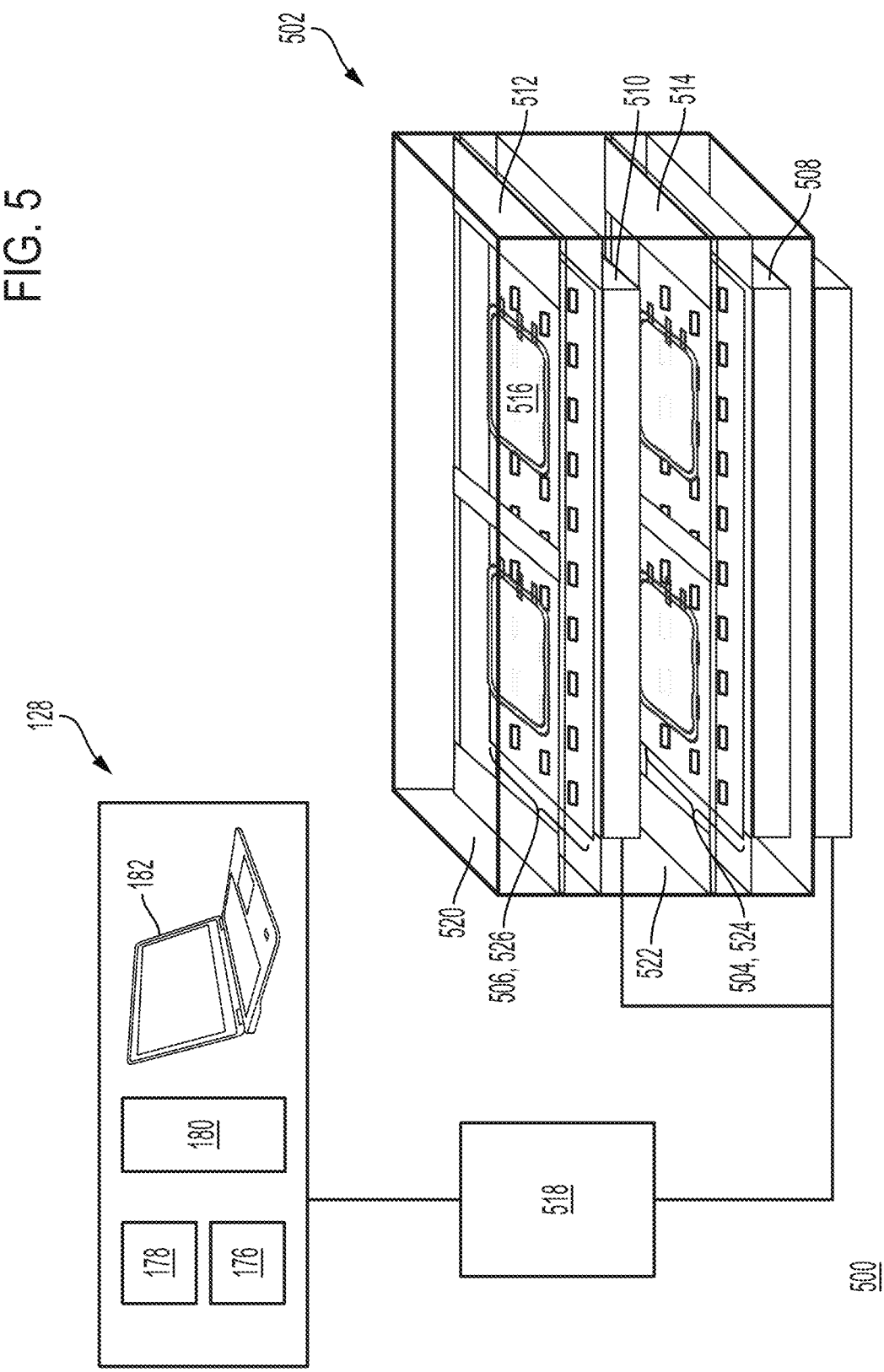

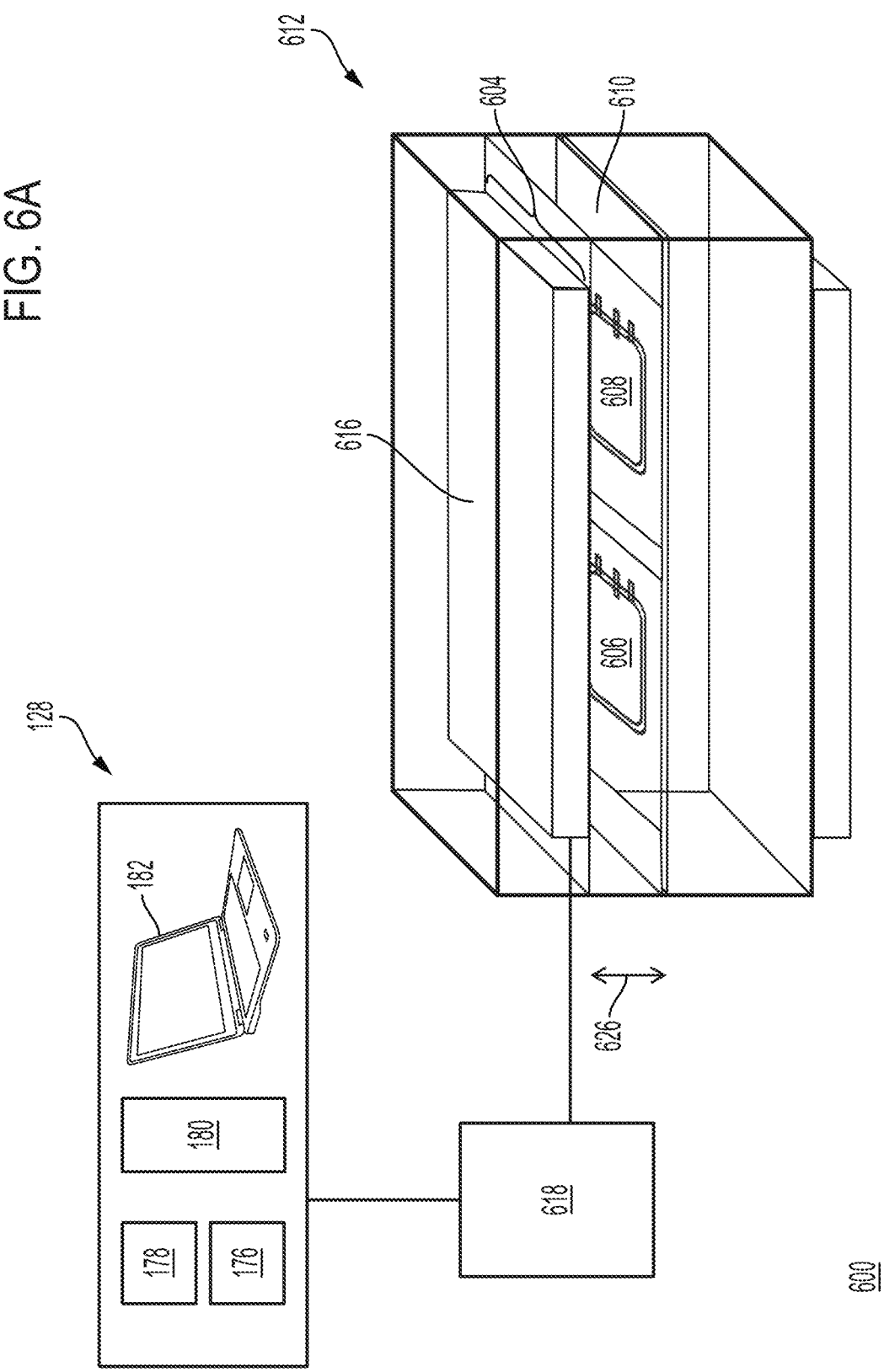

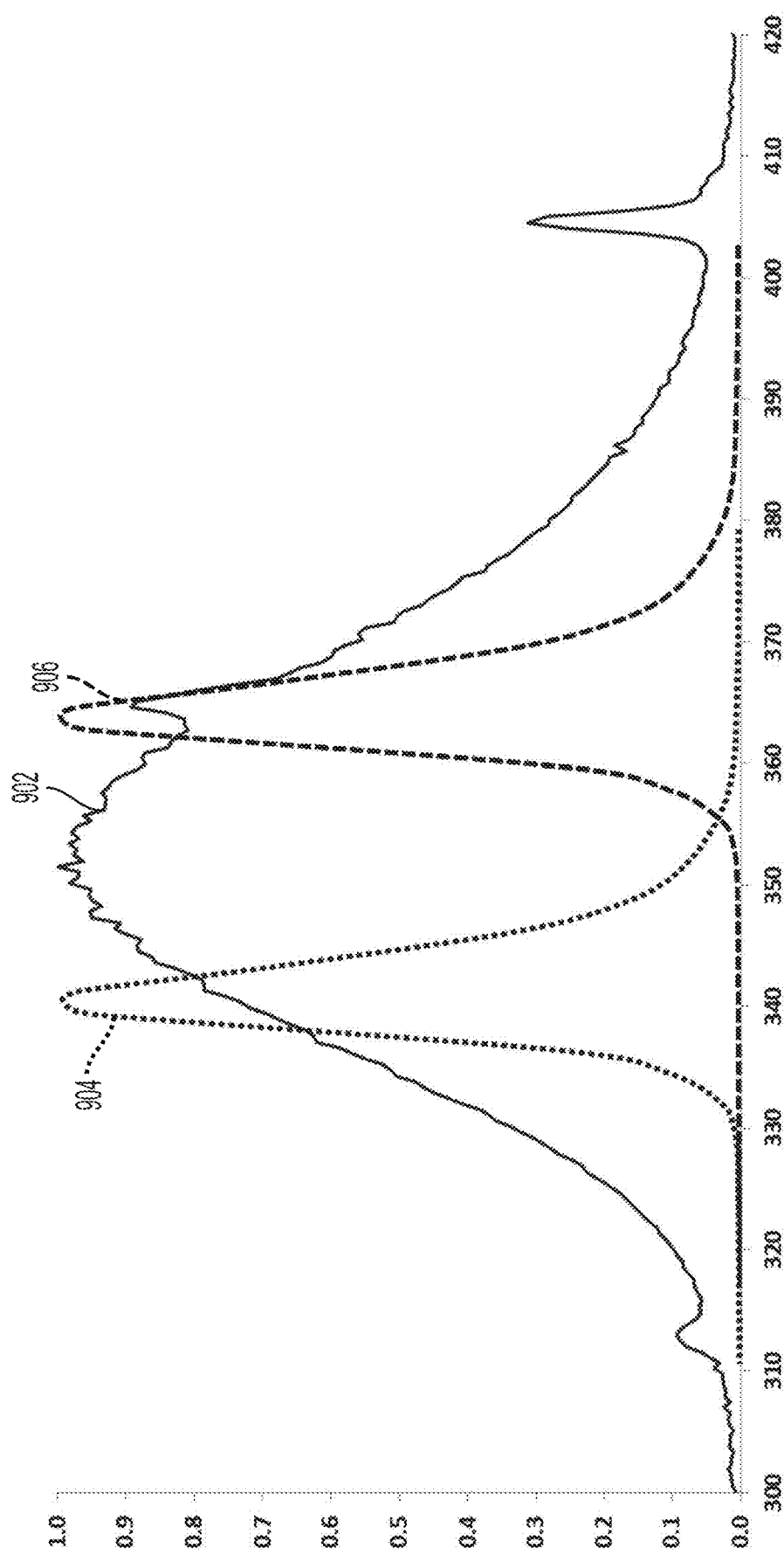

SYSTEMS AND METHODS FOR TREATING BIOLOGICAL FLUIDS

CROSS-REFERENCE TO RELATED APPLICATIONS

This application is a divisional application of U.S. patent application Ser. No. 16/236,193, filed Dec. 28, 2018, which claims priority to U.S. Provisional Application No. 62/612,314, filed Dec. 29, 2017, the disclosures of which are incorporated herein by reference in their entirety.

BACKGROUND

The present disclosure generally relates to systems and methods for treating biological fluids, including mixtures of biological fluids and photochemical agents, with light.

Systems and methods for treating biological fluids with light are well known. For example, U.S. Pat. Nos. 7,459,695, 6,986,867, and 5,593,823 describe a system for treating a biological fluid with light to inactivate pathogens in the biological fluid. In particular, the system includes a treatment chamber with drawers for introducing the biological fluid into the treatment chamber and light sources in the treatment chamber for illuminating the biological fluid. The light sources emit light within a selected range of wavelengths that are effective to inactivate pathogens in the biological fluid, particularly by photochemical inactivation of pathogens. Other systems and methods for treating biological fluids with light may include, for example, systems and methods described in U.S. Pat. Nos. 6,843,961, 7,829,867, 9,320,817 and 8,778,263, and Schlenke, 2014, Transfus. Med. Hemother. 41:309-325.

For systems and methods for treating biological fluids with light, such as blood products including for example, platelets and plasma, it is important to ensure that the blood products are free of pathogens to minimize the risk of infecting an individual receiving a blood product. Testing for the presence of a pathogen in blood is limited by the pathogens tested for and assay sensitivity. As an alternative or supplement to testing for pathogens, methods are known in the art for inactivating pathogens using various compound (e.g., chemical, photochemical)-based inactivation methods (e.g., as disclosed in Schlenke et al., Transfus Med Hemother, 2014, 41, 309-325 and Prowse, Vox Sanguinis, 2013, 104, 183-199). Photochemical pathogen inactivation systems based on psoralens and ultraviolet light for treating blood products include the commercially available INTERCEPT® Blood System (Cerus Corporation), which utilizes amotosalen and illumination with ultraviolet A light, followed by processing with a compound adsorption device (CAD), to remove residual amotosalen and photoproducts thereof.

While previous systems and methods for treating biological fluids have generally performed satisfactorily, it is desirable to develop improved systems and methods for treating biological fluids that more efficiently treat biological fluids, such as, for example, reducing levels (e.g., photoconversion) of a pathogen inactivation compound after photochemical treatment, while maintaining or improving inactivation of a pathogen, and/or provide for improved characteristics (e.g., quality) of the treated biological fluids, such as, for example, by minimizing damage to biological fluids that may be caused by various parameters of the treatment process. In addition, improved monitoring and greater control of various parameters of the treatment process may be desired.

BRIEF SUMMARY

Systems and methods for treating biological fluids with light are provided. In one exemplary embodiment, a treatment system may include a treatment chamber for receiving a biological fluid and one or more light sensors configured to detect light in the treatment chamber. A first array of light sources may be positioned to illuminate the biological fluid in the treatment chamber. The first array of light sources may comprise one or more light source channels that illuminate the biological fluid with light of selected peak wavelengths. For example, a first light source channel may emit light of a first peak wavelength, and a second light source channel may emit light of a second peak wavelength differing from the first peak wavelength by at least 5 nanometers. In other examples, the one or more light source channels may emit light of a first peak wavelength with a full-width half-maximum (FWHM) emission bandwidth of less than 20 nanometers.

Provided herein are systems for treating a biological fluid, the systems comprising: a treatment chamber for receiving a biological fluid (e.g., biological fluid in a container); one or more sensors configured to detect (e.g., measure) light (e.g., light intensity) in the treatment chamber; and a first array of light sources positioned to illuminate the biological fluid in the treatment chamber (e.g., positioned facing the biological fluid), wherein the first array of light sources comprises a first light source channel configured to emit ultraviolet light with a first peak wavelength and a second light source channel configured to emit light with a second peak wavelength, wherein the second peak wavelength differs from the first peak wavelength by at least 5 nanometers.

In some embodiments, the first array of light sources comprises a plurality of light source clusters, wherein each light source cluster of the first array of light sources comprises the first light source channel configured to emit ultraviolet light with the first peak wavelength and the second light source channel configured to emit light with the second peak wavelength. In some embodiments, the first light source channel and/or the second light source channel is configured to emit ultraviolet light. In some embodiments, the first peak wavelength is in an ultraviolet A spectrum (e.g., 315-400 nm). In some embodiments, the first light source channel is configured to emit ultraviolet light with a first peak wavelength of from about 315 nm to about 350 nm. In some embodiments, the first peak wavelength is from about 315 nm to about 335 nm. In some embodiments, the first peak wavelength is from about 330 nm to about 350 nm. In some embodiments, the first peak wavelength is in an ultraviolet A spectrum (e.g., 315-400 nm) and the second peak wavelength is in an ultraviolet C spectrum (e.g., 100-280 nm, 200-280 nm, 240-280 nm). In some embodiments, the first peak wavelength is in an ultraviolet A spectrum (e.g., 315-400 nm) and the second peak wavelength is in an ultraviolet B spectrum (e.g., 280-315 nm). In some embodiments, the first peak wavelength is in an ultraviolet A spectrum (e.g., 315-400 nm) and the second peak wavelength is in an ultraviolet A spectrum. In some embodiments, the first peak wavelength is in an ultraviolet A spectrum and the second peak wavelength is in a visible light spectrum (e.g., 400-800 nm). In some embodiments, the first peak wavelength is in an ultraviolet B spectrum and the second peak wavelength is in an ultraviolet C spectrum.

In some embodiments, the first peak wavelength is in an ultraviolet B spectrum and the second peak wavelength is in a visible light spectrum. In some embodiments, the first peak wavelength is in an ultraviolet C spectrum and the second peak wavelength is in a visible light spectrum. In some embodiments, the first light source channel and the second light source channel comprise one or more (e.g., a plurality of) light emitting diodes (LEDs). In some embodiments, the light intensity at 50% of the maximum peak intensity of light emitted by the first light source channel is within a spectral width of less than 20 nanometers of the first peak wavelength (e.g., no more than 10 nanometers greater than, no more than 10 nanometers less than the first peak wavelength; within 10 nanometers less than, within 10 nanometers greater than the first peak wavelength). In some embodiments, the full-width half-maximum (FWHM) spectral width (e.g., bandwidth) of light (e.g., spectral bandwidth at the maximum peak intensity) emitted by the first light source channel is within 20 nanometers of the first peak wavelength (e.g., no more than 10 nanometers greater than, no more than 10 nanometers less than the first peak wavelength; within 10 nanometers less than, within 10 nanometers greater than the first peak wavelength). In some embodiments, the first array comprises the only/sole light sources of the treatment chamber positioned to illuminate the biological fluid in the treatment chamber. In some embodiments, the systems further comprise a first platform (e.g., tray, well, plate, stage) positioned in the treatment chamber, the first platform configured to carry the biological fluid (e.g., one or more containers of biological fluid). In some embodiments, one or more sensors configured to detect light in the treatment chamber is positioned on or in the first platform. In some embodiments, the systems further comprise a heat exchanger thermally coupled to the first array of light sources. In some embodiments, the first platform is positioned above the first array of light sources and wherein the first array of light sources faces the first platform. In some embodiments, the first platform is positioned below the first array of light sources and wherein the first array of light sources faces the first platform.

In some embodiments, the light sources of the first array of light sources are positioned in a non-uniform distribution on the array. In some embodiments, the first array comprises an inner region having a first density of light sources and an outer region having a second density of light sources, wherein the first density of light sources is different from the second density of light sources. In some embodiments, the first array comprises a continuous inner region containing the midpoint of the first array and a continuous outer region surrounding the inner region, wherein the inner region occupies less than 50% (e.g., less than 40%, 30%, 20%, 10%, 10%-50%, 20%-40%, 10%-20%) of the surface area of the first array, and wherein the outer region occupies a remaining percentage (e.g., 50%, 60%, 70%, 80%, 90%) of the surface area of the first array. In some embodiments, the first array comprises a continuous inner region containing the midpoint of the first array and a continuous outer region surrounding the inner region, wherein the inner region occupies greater than 50% (e.g., greater than 60%, 70%, 80%, 90%, 50%-90%, 60%-80%) of the surface area of the first array, and wherein the outer region occupies a remaining percentage of the surface area of the first array (e.g., less than 50%, 40%, 30%, 20%, 1%, 10%-50%, 20%-40%, 10%-20%). In some embodiments, the outer region comprises a first region containing the outer edge of the first array and wherein no light sources are positioned in the first region. In some embodiments, a first density of light sources positioned in the outer region is greater than a second density of light sources positioned in the inner region. In some embodiments, a first density of light sources positioned in the outer region is less than a second density of light sources positioned in the inner region. In some embodiments, the first array is configured with the light sources positioned in a greater density in the outer 50% surface area of the array compared to the density of the light sources near the midpoint (e.g., inner 10%, 20% surface area) of the array. In some embodiments, the first array comprises a first region of light sources configured to illuminate a first biological fluid (e.g., first container with biological fluid) in the treatment chamber, and a second region of light sources configured to illuminate a second biological fluid (e.g., second container with biological fluid) in the treatment chamber. In some embodiments, a first density of light sources positioned in the first region of the first array and a second density of light sources positioned in the second region of the first array are each greater than a density of light sources positioned outside the first region and the second region of the first array. In some embodiments, the first array comprises a first region of light sources configured to illuminate a first biological fluid (e.g., first container with biological fluid) in the treatment chamber, and a second region of light sources configured to illuminate a second biological fluid (e.g., second container with biological fluid) in the treatment chamber. In some embodiments, a first density of light sources positioned in the first region of the array and a second density of light sources positioned in the second region of the array are each greater than the density of light sources outside the first region and the second region of the array. In some embodiments, the first array is configured such that the light sources illuminate the biological fluid in the treatment chamber with less than 25% variance in irradiance across a surface of the biological fluid (e.g., fluid container, fluid container intercept plane) facing the first array. In some embodiments, the first array is configured such that the light sources illuminate any 5 $cm^2$ area on the biological fluid (e.g., container with biological fluid) in the treatment chamber with less than 25% variance from the integrated irradiance (averaged over surface area) of the entire biological fluid (e.g., container with biological fluid) intercept plane.

In some embodiments, the first array of light sources further comprises a third light source channel configured to emit light of a third peak wavelength. (e.g., wherein each of the first, second, and third peak wavelengths differ from each other by at least 5 nanometers). In some embodiments, each light source cluster of the plurality of light source clusters further comprises a third light source channel configured to emit light of a third peak wavelength. In some embodiments, each light source cluster of the plurality of light source clusters further comprises a third light source channel configured to emit light of a third peak wavelength and a fourth light source channel configured to emit light of a fourth peak wavelength. In some embodiments, the first array of light sources further comprises a third light source channel configured to emit light of a third peak wavelength and a fourth light source channel configured to emit light of a fourth peak wavelength. In some embodiments, each of the first, second, third, and fourth peak wavelengths differs from each other by at least 5 nanometers. In some embodiments, the first peak wavelength is equal to the third peak wavelength and wherein the second peak wavelength is equal to the fourth peak wavelength. In some embodiments, the systems further comprise a barrier (e.g., light barrier, protective barrier) positioned in the treatment chamber between the first array of light sources and the first platform. In some embodiments, the systems further comprise a barrier (e.g., light barrier, protective barrier) positioned in the treatment chamber between the first array of light sources and the biological fluid (e.g., biological fluid in container). In some embodiments, the barrier is a light barrier (e.g., light filter) configured to reduce (e.g., minimize, attenuate, block) transmittance of light having a wavelength of less than the wavelength of light in the UVA spectrum. In some embodiments, the barrier is a light barrier configured to reduce transmittance of light having a wavelength of less than the wavelength of light in the UVB spectrum. In some embodiments, the barrier is a light barrier (e.g., light filter) configured to reduce (e.g., minimize, attenuate, block) transmittance of light having a wavelength at least 20 nm less than (e.g., at least 25 nm less than, at least 30 nm less than) the first peak wavelength and/or another peak wavelength (e.g., at least 20 nm less than the second, third, or fourth peak wavelength). In some embodiments, the barrier is a light barrier (e.g., light filter) configured to reduce transmittance of light having a wavelength at least 20 nm greater than (e.g., at least 25 nm greater than, at least 30 nm greater than) the first peak wavelength and/or another peak wavelength (e.g., at least 20 nm greater than the second, third, or fourth peak wavelength). In some embodiments, the barrier is transparent to light with a wavelength within 30 nm of the first peak wavelength (e.g., within 15 nanometers less than, within 15 nanometers greater than the first peak wavelength; no more than 15 nanometers greater than, no more than 15 nanometers less than the first peak wavelength). In some embodiments, one or more sensors configured to detect light in the treatment chamber is positioned on or in the barrier. In some embodiments, the first platform and the first array of light sources are configured to translate relative to each other to vary a distance between the first array of light sources and the first platform.

In some embodiments, the first platform comprises a first compartment and a second compartment separated from the first compartment. In some embodiments, the first platform is configured to separately hold at least a first container with a first biological fluid and a second container with a second biological fluid. In some embodiments, the first platform is transparent to light with a wavelength within 100 nm (e.g., 75 nm, 50 nm, 40 nm, 30 nm, 20 nm) of the first peak wavelength and/or another peak wavelength (e.g., second, third, or fourth peak wavelength). In some embodiments, the first platform is transparent to ultraviolet light. (e.g., UV-A, UV-B, and/or UV-C). In some embodiments, the first platform is slidably moveable (e.g., in a drawer configuration) for introducing and removing the biological fluid (e.g., container with biological fluid) to and from chamber. In some embodiments, one or more interior surfaces of a plurality of interior surfaces of the treatment chamber is configured to absorb light. In some embodiments, each interior surface of a plurality of interior surfaces of the treatment chamber is configured to absorb light. In some embodiments, one or more interior surfaces of a plurality of interior surfaces of the treatment chamber is configured to reflect light. In some embodiments, each interior surface of a plurality of interior surfaces of the treatment chamber is configured to reflect light.

In some embodiments, the system (e.g., first platform) is configured to agitate the biological fluid during treatment. In some embodiments, the first platform is configured to move (e.g., orbital, reciprocating, controllably move, move at specified rate) to agitate the biological fluid during treatment.

In some embodiments, the systems further comprise one or more heat sensors positioned in the treatment chamber, and/or one or more air flow sensors positioned in the treatment chamber. In some embodiments, the one or more sensors is positioned on the first array of light sources. In some embodiments, the systems further comprise one or more sensors for detecting the presence and/or type of a biological fluid (e.g., container with biological fluid) within the chamber (e.g., in contact with/on the platform).

In some embodiments, the light sources of the first array of light sources are connected in series. In some embodiments, the light sources of the first array of light sources are connected in parallel. In some embodiments, a first set of light sources of the first array of light sources are connected in parallel and a second set of light sources of the first array of light sources are connected in series. In some embodiments, the light sources of the first array of light sources are connected in by a combination of circuits in parallel and in series.

In some embodiments, the systems further comprise a second array of light sources facing an opposite direction as the first array of light sources, wherein each light source of the second array of light sources comprises a third light source channel configured to emit light with the first peak wavelength and a fourth light source channel configured to emit light with the second peak wavelength. In some embodiments, the first array of light sources and the second array of light sources are configured to translate relative to each other to vary a distance between the first array of light sources and the second array of light sources. In some embodiments, the systems further comprise a first platform positioned in the treatment chamber between the first array of light sources and the second array of light sources, the first platform configured to carry the biological fluid (e.g., container with biological fluid). In some embodiments, the systems further comprise a barrier positioned in the treatment chamber between the second array of light sources and the first platform.

In some embodiments, the systems further comprise a second array of light sources facing a same direction as the first array of light sources, wherein each light source of the second array of light sources comprises a third light source channel configured to emit light with the first peak wavelength and a fourth light source channel configured to emit light with the second peak wavelength, and wherein the first array of light sources and the second array of light sources define a first region between the first array of light sources and the second array of light sources. In some embodiments, the systems further comprise a first platform positioned in the treatment chamber in the first region, the first platform configured to carry a first biological fluid; and a second platform positioned in the treatment chamber outside the first region, the second platform configured to carry a second biological fluid, wherein the second array of light sources faces the second platform. In some embodiments, the systems further comprise a barrier positioned in the treatment chamber outside the first region and between the second array of light sources and the second platform. In some embodiments, the first array comprises the only light sources of the treatment chamber positioned to illuminate the biological fluid in the first region of the treatment chamber. In some embodiments, a first set of light sources of the first array of light sources is disposed on a first panel and wherein a second set of light sources of the first array of light sources is disposed on a second panel positioned adjacent to the first panel. In some embodiments, a first set of light sources of the second array of light sources is disposed on a first panel and wherein a second set of light sources of the second array of light sources is disposed on a second panel positioned adjacent to the first panel. In some embodiments, the first panel and the second panel are configured to translate relative to each other to vary a distance between the first panel and the second panel. In some embodiments, the first set of light sources are connected in series, wherein the second set of light sources are connected in series, and wherein the first panel and the second panel are connected in parallel.

In some embodiments, the systems further comprise a control circuitry (e.g., control circuitry operatively coupled (wireless or wired) to the treatment chamber, operatively coupled to one or more arrays). In some embodiments, the control circuitry is configured to adjust or set the first peak wavelength of light emitted by each first light source channel and to adjust or set the second peak wavelength of light emitted by each second light source channel. In some embodiments, the control circuitry is configured to adjust or set an intensity of each light source (e.g., each light source independently) of the first array of light sources. In some embodiments, the control circuitry is configured to adjust or set a first intensity of light emitted by each first light source channel and to adjust or set a second intensity of light emitted by each second light source channel. In some embodiments, the control circuitry is configured to adjust or set a duration of emission of light from each light source of the first array of light sources (e.g., each light source independently). In some embodiments, the control circuitry is configured to adjust or set a first duration of emission of light from each first light source channel and to adjust or set a second duration of emission of light from each second light source channel.

In some embodiments, the control circuitry adjusts or sets the first peak wavelength of light and the second peak wavelength of light based at least in part on a first set of parameters detected by at least one sensor (e.g., light sensor, air flow sensor, heat sensor, sensor for detecting the presence of a biological fluid or a property thereof, sensor for detecting a photochemical compound, sensor positioned to detect fluid depth of a biological fluid). In some embodiments, the control circuitry adjusts or sets the first peak wavelength of light and the second peak wavelength of light based at least in part on a first set of parameters detected by at least one sensor of the one or more sensors configured to detect light. In some embodiments, the control circuitry is configured to adjust or set a duration of emission of light from each light source of the first array of light sources based at least in part on a first set of parameters detected by at least one sensor (e.g., light sensor, air flow sensor, heat sensor, sensor for detecting the presence of a biological fluid or a property thereof, sensor for detecting a photochemical compound, sensor positioned to detect fluid depth of a biological fluid). In some embodiments, the control circuitry is configured to adjust or set a duration of emission of light from each light source of the first array of light sources based at least in part on a first set of parameters detected by at least one sensor of the one or more sensors configured to detect light. In some embodiments, the control circuitry is configured to adjust or set an intensity of emission of light from each light source of the first array of light sources based at least in part on a first set of parameters detected by at least one sensor (e.g., light sensor, air flow sensor, heat sensor, sensor for detecting the presence of a biological fluid or a property thereof, sensor for detecting a photochemical compound, sensor positioned to detect fluid depth of a biological fluid). In some embodiments, the control circuitry is configured to adjust or set an intensity of emission of light from each light source of the first array of light sources based at least in part on a first set of parameters detected by at least one sensor of the one or more sensors configured to detect light.

In some embodiments, the systems further comprise a depth sensor configured to detect a first depth of a first portion of the biological fluid, the biological fluid positioned in the treatment chamber. In some embodiments, the control circuitry is configured to adjust or set an intensity of light emitted by a first light source channel facing the biological fluid based on a depth of the biological fluid. In some embodiments, the control circuitry is configured to adjust or set an intensity of light emitted by a second light source channel facing the biological fluid based on a depth of the biological fluid. In some embodiments, the control circuitry is configured to adjust or set a first intensity of light emitted by each first light source channel facing a first portion of the biological fluid based on a depth of the first portion of the biological fluid and to adjust or set a second intensity of light emitted by each second light source channel facing a second portion of the biological fluid based on a depth of the second portion of the biological fluid. In some embodiments, the systems further comprise one or more depth sensors positioned in the treatment chamber, the one or more depth sensors configured to detect the depth of the first portion of the biological fluid and the depth of the second portion of the biological fluid.

In some embodiments, the systems further comprise a first container positioned within the interior of the treatment chamber (e.g., treatment container) for receiving and treating the biological fluid, wherein the first container is adapted for joining to a source container of the biological fluid, and wherein the first container is adapted for joining to a second container for receiving the biological fluid from the first container.

Further provided herein are systems for treating a biological fluid, the systems comprising: a treatment chamber for receiving a biological fluid (e.g., biological fluid in a container); one or more sensors configured to detect (e.g., measure) light (e.g., light intensity) in the treatment chamber; and a first array of light sources positioned to illuminate the biological fluid in the treatment chamber (e.g., positioned facing the biological fluid), wherein each light source of the first array of light sources comprises a first light source channel configured to emit ultraviolet light with a first peak wavelength in an ultraviolet A, ultraviolet B, and/or ultraviolet C spectrum (e.g., 315 to 400 nanometers), wherein the full-width half-maximum (FWHM) spectral bandwidth of light (e.g., spectral bandwidth at the maximum peak intensity) emitted by the first light source channel is less than 20 nanometers (e.g., within 10 nanometers less than, within 10 nanometers greater than the first peak wavelength; no more than 10 nanometers greater than, no more than 10 nanometers less than the first peak wavelength.

In some embodiments, each light source of the first array of light sources comprises a first light source channel configured to emit ultraviolet light with a first peak wavelength between about 315 nm and about 350 nm. In some embodiments, each light source of the first array of light sources comprises a first light source channel configured to emit ultraviolet light with a first peak wavelength between about 315 nm and about 335 nm (e.g., between about 320 nm and about 330 nm, or about 325 nm). In some embodiments, each light source of the first array of light sources comprises a first light source channel configured to emit ultraviolet light with a first peak wavelength between about 330 nm and about 350 nm (e.g., between about 335 nm and about 345 nm, or about 340 nm). In some embodiments, 50% of the maximum peak intensity of light emitted by the first light source channel is within 10 nanometers of the first peak wavelength. In some embodiments, the light intensity at 50% of the maximum peak intensity of light emitted by the first light source channel is within (e.g., defines) a spectral width less than 20 nanometers (e.g., no more than 10 nanometers greater than, no more than 10 nanometers less than the first peak wavelength; within 10 nanometers less than, within 10 nanometers greater than the first peak wavelength). In some embodiments, the first array of light sources further comprises a second light source channel configured to emit light (e.g., ultraviolet light) with a second peak wavelength. In some embodiments, the second peak wavelength differs from the first peak wavelength by at least 5 nanometers. In some embodiments, the second peak wavelength is in an ultraviolet A spectrum (e.g., 315-400 nm), an ultraviolet B spectrum (e.g., 280-315 nm), an ultraviolet C spectrum (e.g., 100-280 nm, 200-280 nm, 240-280 nm), or a visible light spectrum (e.g., 400-800 nm). In some embodiments, 50% of the maximum peak intensity of light emitted by the second light source channel is within 10 nanometers of the second peak wavelength (e.g., no more than 10 nanometers greater than, no more than 10 nanometers less than the second peak wavelength; within 10 nanometers less than, within 10 nanometers greater than the second peak wavelength). In some embodiments, the full-width half-maximum (FWHM) spectral bandwidth of light (e.g., spectral bandwidth at the maximum peak intensity) emitted by the second light source channel is less than 20 nanometers (e.g., no more than 10 nanometers greater than, no more than 10 nanometers less than the second peak wavelength; within 10 nanometers less than, within 10 nanometers greater than the second peak wavelength). In some embodiments, the first array of light sources comprises a plurality of light source clusters, and wherein each light source cluster of the first array of light sources comprises the first light source channel configured to emit ultraviolet light with the first peak wavelength and the second light source channel configured to emit light (e.g., ultraviolet light) with a second peak wavelength. In some embodiments, the first light source channel comprises one or more (e.g., a plurality of) LEDs. In some embodiments, the second light source channel comprises one or more (e.g., a plurality of) LEDs.

In some embodiments, the systems further comprise a first platform (e.g., tray, well, plate, stage) positioned in the treatment chamber, the first platform configured to carry the biological fluid (e.g., one or more containers of biological fluid). In some embodiments, the systems further comprise a heat exchanger thermally coupled to the first array of light sources. In some embodiments, the first platform is positioned above the first array of light sources and wherein the first array of light sources faces the first platform. In some embodiments, the first platform is positioned below the first array of light sources and wherein the first array of light sources faces the first platform. In some embodiments, one or more sensors configured to detect light in the treatment chamber is positioned on or in the first platform.

In some embodiments, the light sources of the first array of light sources are positioned in a non-uniform distribution on the array. In some embodiments, the first array comprises an inner region having a first density of light sources and an outer region having a second density of light sources, wherein the first density of light sources is different from the second density of light sources. In some embodiments, the first array comprises a continuous inner region containing the midpoint of the first array and a continuous outer region surrounding the inner region, wherein the inner region occupies less than 50% (e.g., less than 40%, 30%, 20%, 10%, 10%-50%, 20%-40%, 10%-20%) of the surface area of the first array, and wherein the outer region occupies a remaining percentage (e.g., 50%, 60%, 70%, 80%, 90%) of the surface area of the first array. In some embodiments, the first array comprises a continuous inner region containing the midpoint of the first array and a continuous outer region surrounding the inner region, wherein the inner region occupies greater than 50% (e.g., greater than 60%, 70%, 80%, 90%, 50%-90%, 60%-80%) of the surface area of the first array, and wherein the outer region occupies a remaining percentage of the surface area of the first array (e.g., less than 50%, 40%, 30%, 20%, 1%, 10%-50%, 20%-40%, 10%-20%). In some embodiments, a first density of light sources positioned in the outer region is greater than a second density of light sources positioned in the inner region. In some embodiments, a first density of light sources positioned in the outer region is less than a second density of light sources positioned in the inner region. In some embodiments, the outer region comprises a first region containing the outer edge of the first array and wherein no light sources are positioned in the first region. In some embodiments, the first array comprises a first region of light sources configured to illuminate a first biological fluid (e.g., first container with biological fluid) in the treatment chamber, and a second region of light sources configured to illuminate a second biological fluid (e.g., second container with biological fluid) in the treatment chamber. In some embodiments, a first density of light sources positioned in the first region of the first array and a second density of light sources positioned in the second region of the first array are each greater than a density of light sources positioned outside the first region and the second region of the first array. In some embodiments, the first array is configured such that the light sources illuminate the biological fluid in the treatment chamber with less than 25% variance in irradiance across a surface of the biological fluid (e.g., fluid container, fluid container intercept plane) facing the first array. In some embodiments, the first array is configured such that the light sources illuminate any 5 cm$^2$ area on the biological fluid (e.g., container with biological fluid) in the treatment chamber with less than 25% variance from the integrated or average irradiance of the entire biological fluid (e.g., container with biological fluid) intercept plane.

In some embodiments, the first array of light sources further comprises a third light source channel configured to emit light of a third peak wavelength. (e.g., wherein each of the first, second, and third peak wavelengths differs from each other by at least 5 nanometers). In some embodiments, each light source cluster of the plurality of light source clusters further comprises a third light source channel configured to emit light of a third peak wavelength.

In some embodiments, each light source cluster of the plurality of light source clusters further comprises a third light source channel configured to emit light of a third peak wavelength and a fourth light source channel configured to emit light of a fourth peak wavelength. In some embodiments, the first array of light sources further comprises a third light source channel configured to emit light of a third peak wavelength and a fourth light source channel configured to emit light of a fourth peak wavelength. In some embodiments, each of the first, second, third, and fourth peak wavelengths differs from each other by at least 5 nanometers. In some embodiments, the first peak wavelength is equal to the third peak wavelength and wherein the second peak wavelength is equal to the fourth peak wavelength.

In some embodiments, the systems further comprise a barrier (e.g., light barrier, protective barrier) positioned in the treatment chamber between the first array of light sources and the first platform. In some embodiments, the systems further comprise a barrier (e.g., light barrier, protective barrier) positioned in the treatment chamber between the first array of light sources and the biological fluid (e.g., biological fluid in container). In some embodiments, the barrier is a light barrier (e.g., light filter) configured to reduce (e.g., minimize, attenuate, block) transmittance of light having a wavelength of less than the wavelength of light in the UVA spectrum. In some embodiments, the barrier is a light barrier configured to reduce transmittance of light having a wavelength of less than the wavelength of light in the UVB spectrum. In some embodiments, the barrier is a light barrier (e.g., light filter) configured to reduce (e.g., minimize, attenuate, block) transmittance of light having a wavelength at least 20 nm less than (e.g., at least 25 nm less than, at least 30 nm less than) the first peak wavelength and/or another peak wavelength (e.g., at least 20 nm less than the second, third, or fourth peak wavelength). In some embodiments, the barrier is a light barrier (e.g., light filter) configured to reduce transmittance of light having a wavelength at least 20 nm greater than (e.g., at least 25 nm greater than, at least 30 nm greater than) the first peak wavelength and/or another peak wavelength (e.g., at least 20 nm greater than the second, third, or fourth peak wavelength). In some embodiments, the barrier is transparent to light with a wavelength within 30 nm of the first peak wavelength (e.g., within 15 nanometers less than, within 15 nanometers greater than the first peak wavelength; no more than 15 nanometers greater than, no more than 15 nanometers less than the first peak wavelength). In some embodiments, one or more sensors configured to detect light in the treatment chamber is positioned on or in the barrier. In some embodiments, the first platform and the first array of light sources are configured to translate relative to each other to vary a distance between the first array of light sources and the first platform.

In some embodiments, the first platform comprises a first compartment and a second compartment separated from the first compartment. In some embodiments, the first platform is configured to separately hold at least a first container with a first biological fluid and a second container with a second biological fluid. In some embodiments, the first platform is transparent to light with a wavelength within 100 nm (e.g., 75 nm, 50 nm, 40 nm, 30 nm, 20 nm) of the first peak wavelength and/or another peak wavelength (second, third, or fourth peak wavelength). In some embodiments, the first platform is transparent to ultraviolet light. (e.g., UV-A, UV-B, and/or UV-C). In some embodiments, the first platform is slidably moveable (e.g., in a drawer configuration) for introducing and removing the biological fluid (e.g., container with biological fluid) to and from chamber. In some embodiments, one or more interior surfaces of the treatment chamber (e.g., of a plurality of interior surfaces of the treatment chamber) is configured to absorb light. In some embodiments, each interior surface of a plurality of interior surfaces of the treatment chamber is configured to absorb light. In some embodiments, one or more interior surfaces of the treatment chamber (e.g., of a plurality of interior surfaces of the treatment chamber) is configured to reflect light. In some embodiments, each interior surface of the treatment chamber is configured to reflect light.

In some embodiments, the system (e.g., first platform) is configured to agitate the biological fluid during treatment. In some embodiments, the first platform is configured to move (e.g., orbital, reciprocating, controllably move, move at specified rate) to agitate the biological fluid during treatment.

In some embodiments, the systems further comprise one or more heat sensors positioned in the treatment chamber, and/or one or more air flow sensors positioned in the treatment chamber. In some embodiments, the one or more sensors is positioned on the first array of light sources. In some embodiments, the systems further comprise one or more sensors for detecting the presence and/or type of a biological fluid (e.g., container with biological fluid) within the chamber (e.g., in contact with/on the platform).

In some embodiments, the light sources of the first array of light sources are connected in series. In some embodiments, the light sources of the first array of light sources are connected in parallel. In some embodiments, a first set of light sources of the first array of light sources are connected in parallel and a second set of light sources of the first array of light sources are connected in series. In some embodiments, the light sources of the first array of light sources are connected in by a combination of circuits in parallel and in series.

In some embodiments, the systems further comprise a second array of light sources facing an opposite direction as the first array of light sources, wherein each light source of the second array of light sources comprises a third light source channel configured to emit light with the first peak wavelength and a fourth light source channel configured to emit light with the second peak wavelength. In some embodiments, the first array of light sources and the second array of light sources are configured to translate relative to each other to vary a distance between the first array of light sources and the second array of light sources. In some embodiments, the systems further comprise a first platform positioned in the treatment chamber between the first array of light sources and the second array of light sources, the first platform configured to carry the biological fluid (e.g., container with biological fluid). In some embodiments, the systems further comprise a barrier positioned in the treatment chamber between the second array of light sources and the first platform.

In some embodiments, the systems further comprise a second array of light sources facing a same direction as the first array of light sources, wherein each light source of the second array of light sources comprises a third light source channel configured to emit light with the first peak wavelength and a fourth light source channel configured to emit light with the second peak wavelength, and wherein the first array of light sources and the second array of light sources define a first region between the first array of light sources and the second array of light sources. In some embodiments, the systems further comprise a first platform positioned in the treatment chamber in the first region, the first platform configured to carry a first biological fluid; and a second platform positioned in the treatment chamber outside the first region, the second platform configured to carry a second biological fluid, wherein the second array of light sources faces the second platform. In some embodiments, the systems further comprise a barrier positioned in the treatment chamber outside the first region and between the second array of light sources and the second platform. In some embodiments, the first array comprises the only light sources of the treatment chamber positioned to illuminate the biological fluid in the first region of the treatment chamber. In some embodiments, a first set of light sources of the first array of light sources is disposed on a first panel and wherein a second set of light sources of the first array of light sources is disposed on a second panel positioned adjacent to the first panel. In some embodiments, a first set of light sources of the second array of light sources is disposed on a first panel and wherein a second set of light sources of the second array of light sources is disposed on a second panel positioned adjacent to the first panel. In some embodiments, the first panel and the second panel are configured to translate relative to each other to vary a distance between the first panel and the second panel. In some embodiments, the first set of light sources are connected in series, wherein the second set of light sources are connected in series, and wherein the first panel and the second panel are connected in parallel.

In some embodiments, the systems further comprise a control circuitry (e.g., control circuitry operatively coupled (wireless or wired) to the treatment chamber, operatively coupled to one or more arrays). In some embodiments, the control circuitry is configured to adjust or set the first peak wavelength of light emitted by each light source (e.g., each light source independently) of the first array of light sources. In some embodiments, the control circuitry is configured to adjust or set the first peak wavelength of light emitted by each first light source channel and to adjust the second peak wavelength of light emitted by each second light source channel. In some embodiments, the control circuitry is configured to adjust or set an intensity of each light source (e.g., each light source independently) of the first array of light sources. In some embodiments, the control circuitry is configured to adjust or set a first intensity of light emitted by each first light source channel and to adjust or set a second intensity of light emitted by each second light source channel. In some embodiments, the control circuitry is configured to adjust or set a duration of emission of light from each light source of the first array of light sources (e.g., each light source independently). In some embodiments, the control circuitry is configured to adjust or set a first duration of emission of light from each first light source channel and to adjust or set a second duration of emission of light from each second light source channel.

In some embodiments, the control circuitry is configured to adjust or set the first peak wavelength of light from each light source of the first array of light sources based at least in part on a first set of parameters detected by at least one sensor (e.g., light sensor, air flow sensor, heat sensor, sensor for detecting the presence of a biological fluid or a property thereof, sensor for detecting a photochemical compound, sensor positioned to detect fluid depth of a biological fluid). In some embodiments, the control circuitry is configured to adjust or set the first peak wavelength of light from each light source of the first array of light sources based at least in part on a first set of parameters detected by at least one sensor of the one or more sensors configured to detect light. In some embodiments, the control circuitry adjusts or sets the first peak wavelength of light and the second peak wavelength of light based at least in part on a first set of parameters detected by at least one sensor of the one or more sensors configured to detect light. In some embodiments, the control circuitry is configured to adjust or set a duration of emission of light from each light source of the first array of light sources based at least in part on a first set of parameters detected by at least one sensor (e.g., light sensor, air flow sensor, heat sensor, sensor for detecting the presence of a biological fluid or a property thereof, sensor for detecting a photochemical compound, sensor positioned to detect fluid depth of a biological fluid). In some embodiments, the control circuitry is configured to adjust or set a duration of emission of light from each light source of the first array of light sources based at least in part on a first set of parameters detected by at least one sensor of the one or more sensors configured to detect light. In some embodiments, the control circuitry is configured to adjust or set an intensity of emission of light from each light source of the first array of light sources based at least in part on a first set of parameters detected by at least one sensor (e.g., light sensor, air flow sensor, heat sensor, sensor for detecting the presence of a biological fluid or a property thereof, sensor for detecting a photochemical compound, sensor positioned to detect fluid depth of a biological fluid). In some embodiments, the control circuitry is configured to adjust or set an intensity of emission of light from each light source of the first array of light sources based at least in part on a first set of parameters detected by at least one sensor of the one or more sensors configured to detect light.

In some embodiments, the systems further comprise a depth sensor configured to detect a first depth of a first portion of the biological fluid, the biological fluid positioned in the treatment chamber. In some embodiments, the control circuitry is configured to adjust or set an intensity of light emitted by a first light source channel facing the biological fluid based on a depth of the biological fluid. In some embodiments, the control circuitry is configured to adjust or set an intensity of light emitted by a second light source channel facing the biological fluid based on a depth of the biological fluid. In some embodiments, the control circuitry is configured to adjust or set a first intensity of light emitted by each first light source channel facing a first portion of the biological fluid based on a depth of the first portion of the biological fluid and to adjust or set a second intensity of light emitted by each second light source channel facing a second portion of the biological fluid based on a depth of the second portion of the biological fluid. In some embodiments, the systems further comprise one or more depth sensors positioned in the treatment chamber, the one or more depth sensors configured to detect the depth of the first portion of the biological fluid and the depth of the second portion of the biological fluid.

In some embodiments, the systems further comprise a first container positioned within the interior of the treatment chamber (e.g., treatment container) for receiving and treating the biological fluid, wherein the first container is adapted for joining to a source container of the biological fluid, and wherein the first container is adapted for joining to a second container for receiving the biological fluid from the first container.

Further provided herein are methods for treating a biological fluid (e.g., inactivating a pathogen in a biological fluid), the methods comprising: providing a biological fluid in admixture with a pathogen-inactivating compound (e.g., photochemical agent); illuminating (e.g., exposing) the biological fluid with ultraviolet light of a first peak wavelength; and illuminating (e.g., exposing) the biological fluid with light (e.g., ultraviolet light) of a second peak wavelength, wherein the first peak wavelength differs from the second peak wavelength by at least 5 nm, wherein illuminating the biological fluid occurs for a duration and at an intensity sufficient to inactivate a pathogen in the biological fluid.

In some embodiments, the ultraviolet light of a first peak wavelength is provided by a first light source (e.g., within a treatment chamber) and wherein the light of the second peak wavelength is provided by a second light source (e.g., within a treatment chamber). In some embodiments, 50% of the maximum peak intensity of light emitted by the first light source is within 10 nanometers of the first peak wavelength (e.g., no more than 10 nanometers greater than, no more than 10 nanometers less than the first peak wavelength; within 10 nanometers less than, within 10 nanometers greater than the first peak wavelength). In some embodiments, the full-width half-maximum (FWHM) spectral bandwidth of light (e.g., spectral bandwidth at the maximum peak intensity) emitted by the first light source is less than 20 nanometers (e.g., no more than 10 nanometers greater than, no more than 10 nanometers less than the first peak wavelength; within 10 nanometers less than, within 10 nanometers greater than the first peak wavelength). In some embodiments, the ultraviolet light of the first peak wavelength is in an ultraviolet A spectrum (e.g., 315 to 400 nanometers). In some embodiments, the light of the second peak wavelength is in an ultraviolet B spectrum (e.g., 280-315 nm), an ultraviolet C spectrum (e.g., 100-280 nm, 200-280 nm, 240-280 nm), or a visible light spectrum (e.g., 400-800 nm). In some embodiments, the first peak wavelength is in an ultraviolet A spectrum (e.g., 315-400 nm) and the second peak wavelength is in an ultraviolet C spectrum (e.g., 100-280 nm, 200-280 nm, 240-280 nm). In some embodiments, the first peak wavelength is in an ultraviolet A spectrum (e.g., 315-400 nm) and the second peak wavelength is in an ultraviolet B spectrum (e.g., 280-315 nm). In some embodiments, the first peak wavelength is in an ultraviolet A spectrum (e.g., 315-400 nm) and the second peak wavelength is in an ultraviolet A spectrum. In some embodiments, the first peak wavelength is in an ultraviolet A spectrum and the second peak wavelength is in a visible light spectrum (e.g., 400-800 nm). In some embodiments, the first peak wavelength is in an ultraviolet B spectrum and the second peak wavelength is in an ultraviolet C spectrum. In some embodiments, the first peak wavelength is in an ultraviolet B spectrum and the second peak wavelength is in a visible light spectrum. In some embodiments, the first peak wavelength is in an ultraviolet C spectrum and the second peak wavelength is in a visible light spectrum. In some embodiments, illuminating the biological fluid with ultraviolet light of the first peak wavelength and illuminating the biological fluid with light of the second peak wavelength occurs sequentially or concurrently. In some embodiments, illuminating the biological fluid with ultraviolet light of the first peak wavelength includes illuminating the biological fluid with ultraviolet light of the first peak wavelength for a first duration and wherein illuminating the biological fluid with light of the second peak wavelength includes illuminating the biological fluid with light of the second peak wavelength for a second duration. In some embodiments, the first duration is different from the second duration. In some embodiments, the first duration is equal to the second duration. In some embodiments, illuminating the biological fluid with ultraviolet light of the first peak wavelength is performed by a first set of light sources, wherein illuminating the biological fluid with light of the second peak wavelength is performed by a second set of light sources, and wherein the first and the second set of light sources are disposed on an array of light source clusters. In some embodiments, first light source and the second light source comprise LEDs. In some embodiments, the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540. In some embodiments, the pathogen inactivation compound is a psoralen (e.g., amotosalen).

Further provided herein are methods for treating a biological fluid (e.g., inactivating a pathogen in a biological fluid) comprising: providing a biological fluid in admixture with a pathogen inactivation compound (e.g., photochemical agent); and illuminating (e.g., exposing) the biological fluid with ultraviolet light of a first peak wavelength provided by a first ultraviolet light source (e.g., within a treatment chamber), wherein the full-width half-maximum (FWHM) spectral bandwidth of the ultraviolet light (e.g., spectral bandwidth at the maximum peak intensity) emitted by the first ultraviolet light source is less than 20 nanometers (e.g., no more than 10 nanometers greater than, no more than 10 nanometers less than the first peak wavelength; within 10 nanometers less than, within 10 nanometers greater than the first peak wavelength), and wherein illuminating the biological fluid occurs for a duration and at an intensity sufficient to inactivate a pathogen in the biological fluid.

In some embodiments, the ultraviolet light of the first peak wavelength is in an ultraviolet A spectrum (e.g., 315 to 400 nanometers). In some embodiments, the first peak wavelength is between 330 nanometers and 350 nanometers (e.g., 340 nm+5 nm). In some embodiments, the ultraviolet light of the first peak wavelength is in an ultraviolet B spectrum. (e.g., 280-315 nanometers). In some embodiments, the ultraviolet light of the first peak wavelength is in an ultraviolet C spectrum (e.g., 100-280 nm, 200-280 nm, 240-280 nm). In some embodiments, the first light source comprises an LED. In some embodiments, illuminating the biological fluid with ultraviolet light of the first peak wavelength is performed using the first ultraviolet light source as the only light source of the treatment chamber illuminating the biological fluid. In some embodiments, the first light source comprises the only ultraviolet light source of the treatment chamber illuminating the biological fluid during the treatment. In some embodiments, the biological fluid is within a container and wherein illuminating the biological fluid with ultraviolet light of the first peak wavelength is performed by a first set of light sources disposed on an array of light sources, the first set of light sources facing only one side of the container. In some embodiments, the biological fluid is within a container, and wherein illuminating the biological fluid with ultraviolet light of the first peak wavelength is performed by a first set of light sources disposed on an array of light sources (e.g., within a treatment chamber), and wherein the array is positioned facing (e.g., illuminating) one side of the container of biological fluid during the treatment. In some embodiments, the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540. In some embodiments, the pathogen inactivation compound is a psoralen (e.g., amotosalen).

Further provided herein are methods for treating a biological fluid (e.g., inactivating a pathogen in a biological fluid), comprising: introducing a biological fluid (e.g., biological fluid in a container) in admixture with a pathogen inactivation compound (e.g., photochemical agent) into a treatment chamber, the treatment chamber comprising, one or more light sensors configured to detect (e.g., measure) light (e.g., light intensity) in the treatment chamber and a first array of light sources configured to illuminate the biological fluid in the treatment chamber, wherein each light source of the first array of light sources is included in a first light source channel configured to emit ultraviolet light with a first peak wavelength or in a second light source channel configured to emit light (e.g., ultraviolet light) with a second peak wavelength, the first peak wavelength differing from the second peak wavelength by at least 5 nanometers; and illuminating the biological fluid by emitting light with the first peak wavelength from each first light source channel and emitting light with the second peak wavelength from each second light source channel for a duration and at an intensity sufficient to inactivate a pathogen in the biological fluid.

In some embodiments, the methods further comprise determining a set of characteristics of the biological fluid; determining a treatment profile based on the set of characteristics of the biological fluid; and adjusting or setting a set of parameters of the treatment chamber in accordance with the treatment profile.

In some embodiments, illuminating the biological fluid is performed in accordance with the treatment profile. In some embodiments, the duration and the intensity sufficient to inactivate the pathogen is determined from the treatment profile. In some embodiments, the first array of light sources comprises a plurality of light source clusters, wherein each light source cluster of the first array of light sources comprises the first light source channel configured to emit ultraviolet light with the first peak wavelength and the second light source channel configured to emit light with the second peak wavelength. In some embodiments, 50% of the maximum peak intensity of light emitted by the first light source channel is within 10 nanometers of the first peak wavelength (e.g., no more than 10 nanometers greater than, no more than 10 nanometers less than the first peak wavelength; within 10 nanometers less than, within 10 nanometers greater than the first peak wavelength). In some embodiments, the full-width half-maximum (FWHM) spectral bandwidth of light (e.g., spectral bandwidth at the maximum peak intensity) emitted by the first light source channel is less than 20 nanometers (e.g., no more than 10 nanometers greater than, no more than 10 nanometers less than the first peak wavelength; within 10 nanometers less than, within 10 nanometers greater than the first peak wavelength). In some embodiments, the set of characteristics of the biological fluid includes at least one of: a volume of the biological fluid, a type of the biological fluid, or a temperature of the biological fluid. In some embodiments, determining the treatment profile based on the set of characteristics comprises determining the first peak wavelength and the second peak wavelength. In some embodiments, determining the treatment profile based on the set of characteristics comprises determining a first intensity of ultraviolet light with the first peak wavelength and a second intensity of light with the second peak wavelength. In some embodiments, determining the treatment profile based on the set of characteristics comprises determining a first duration of emission of ultraviolet light with the first peak wavelength and a second duration of emission of light with the second peak wavelength. In some embodiments, the treatment chamber further comprising a first platform positioned in the treatment chamber, the first platform carrying the biological fluid (e.g., one or more containers of biological fluid). In some embodiments, the treatment chamber further comprising a heat exchanger thermally coupled to the first array of light sources. In some embodiments, adjusting or setting the set of parameters of the treatment chamber comprises adjusting or setting a distance between the first array of light sources and the first platform. In some embodiments, adjusting or setting the set of parameters of the treatment chamber comprises adjusting or setting a temperature of the treatment chamber. In some embodiments, the methods further comprise agitating the biological fluid. In some embodiments, adjusting or setting the set of parameters of the treatment chamber comprises adjusting or setting a parameter associated with agitation of the biological fluid.

Further provided herein are methods for treating a biological fluid (e.g., inactivating a pathogen in a biological fluid), comprising: introducing the biological fluid (e.g., biological fluid in a container) in admixture with a pathogen inactivation compound (e.g., photochemical agent) into a treatment chamber, the treatment chamber comprising one or more light sensors configured to detect (e.g., measure) light (e.g., light intensity) in the treatment chamber and a first array of light sources configured to illuminate the biological fluid in the treatment chamber, wherein each light source of the first array of light sources is included in a first light source channel configured to emit ultraviolet light with a first peak wavelength in the ultraviolet A, ultraviolet B, and/or ultraviolet C spectrum wherein the full-width half-maximum (FWHM) spectral bandwidth of light (e.g., spectral bandwidth at the maximum peak intensity) emitted by the first light source channel is less than 20 nanometers (e.g., no more than 10 nanometers greater than, no more than 10 nanometers less than the first peak wavelength; within 10 nanometers less than, within 10 nanometers greater than the first peak wavelength); and illuminating the biological fluid by emitting light with the first peak wavelength from each first light source channel for a first duration and at first intensity sufficient to inactivate a pathogen in the biological fluid.

In some embodiments, each light source of the first array of light sources comprises a first light source channel configured to emit ultraviolet light with a first peak wavelength between about 330 nm and about 350 nm (e.g., between about 335 nm and about 345 nm, or about 340 nm). In some embodiments, the methods further comprise determining a set of characteristics of the biological fluid; determining a treatment profile based on the set of characteristics of the biological fluid; and adjusting or setting a set of parameters of the treatment chamber in accordance with the treatment profile. In some embodiments, illuminating the biological fluid is performed in accordance with the treatment profile. In some embodiments, the first duration and the first intensity sufficient to inactivate the pathogen is determined from the treatment profile. In some embodiments, 50% of the maximum peak intensity of light emitted by the first light source channel is within 20 nanometers of the first peak wavelength (e.g., within 10 nanometers less than, within 10 nanometers greater than the first peak wavelength). In some embodiments, each light source of the first array of light sources further comprises a second light source channel configured to emit light of a second peak wavelength. In some embodiments, the second peak wavelength differs from first peak wavelength by at least 5 nm. In some embodiments, 50% of the maximum peak intensity of light emitted by the second light source channel is within 10 nanometers of the second peak wavelength (e.g., no more than 10 nanometers greater than, no more than 10 nanometers less than the first peak wavelength; within 10 nanometers less than, within 10 nanometers greater than the second peak wavelength). In some embodiments, a full-width half-maximum (FWHM) spectral bandwidth of light (e.g., spectral bandwidth at the maximum peak intensity) emitted by the second light source channel is less than 20 nanometers (e.g., no more than 10 nanometers greater than, no more than 10 nanometers less than the first peak wavelength; within 10 nanometers less than, within 10 nanometers greater than the second peak wavelength). In some embodiments, the first array of light sources comprises a plurality of light source clusters, and wherein each light source cluster of the first array of light sources comprises the first light source channel configured to emit ultraviolet light with the first peak wavelength and the second light source channel configured to emit ultraviolet light with the second peak wavelength. In some embodiments, the set of characteristics of the biological fluid includes at least one of: a volume of the biological fluid, a type of the biological fluid, or a temperature of the biological fluid. In some embodiments, determining the treatment profile based on the set of characteristics comprises determining the first peak wavelength. In some embodiments, determining the treatment profile based on the set of characteristics comprises determining the first intensity of light with the first peak wavelength. In some embodiments, determining the treatment profile based on the set of characteristics comprises determining the first duration of emission of light with the first peak wavelength. In some embodiments, the treatment chamber further comprising a first platform positioned in the treatment chamber, the first platform carrying the biological fluid (e.g., one or more containers of biological fluid). In some embodiments, the treatment chamber further comprising a heat exchanger thermally coupled to the first array of light sources. In some embodiments, adjusting or setting the set of parameters of the treatment chamber comprises adjusting or setting a distance between the first array of light sources and the first platform. In some embodiments, adjusting or setting the set of parameters of the treatment chamber comprises adjusting or setting a temperature of the treatment chamber. In some embodiments, the methods further comprise agitating the biological fluid. In some embodiments, adjusting or setting the set of parameters of the treatment chamber comprises adjusting or setting a parameter associated with agitation of the biological fluid.

In some embodiments of any of the above embodiments, the method for treating is sufficient to inactivate at least 1 log (e.g., at least 2 logs, at least 3 logs, at least 4 logs) of a pathogen in the biological fluid. In some embodiments, the method for treating is sufficient to inactivate at least 1 log (e.g., at least 2 logs, at least 3 logs, at least 4 logs) of a pathogen in the biological fluid, and wherein the biological fluid after illuminating is suitable for infusion into a subject without further processing to remove residual pathogen inactivation compound or photoproducts thereof. In some embodiments, illuminating the biological fluid in admixture with the pathogen inactivation compound reduces the concentration of pathogen inactivation compound to 5 µM or less (e.g., 4 µM or less, 3 µM or less, 2 µM or less, 1 µM or less, 0.5 µM or less) after illumination. In some embodiments, the biological fluid comprises 5 µM or less (e.g., 4 µM or less, 3 µM or less, 2 µM or less, 1 µM or less, 0.5 µM or less) of pathogen inactivation compound after illuminating (e.g., without further processing to remove residual pathogen inactivation compound, such as prior to any subsequent compound removal step, e.g., subjecting the biological fluid to a CAD). In some embodiments, the concentration of pathogen inactivation compound in admixture with the biological fluid prior to illumination is at least 10 µM (e.g., at least 15 µM, at least 20 µM, at least 30 µM, at least 40 µM, at least 50 µM, at least 60 µM, at least 70 µM, at least 80 µM, at least 90 µM, at least 100 µM, at least 110 µM, at least 120 µM, at least 130 µM, at least 140 µM, or at least 150 µM). In some embodiments, the concentration of pathogen inactivation compound in admixture with the biological fluid prior to illumination is about 10 µM to about 1500 µM, about 10 µM to about 1000 µM, about 10 µM to about 500 µM, about 10 µM to about 250 µM, about 10 µM to about 200 µM, about 10 µM to about 150 µM, about 15 µM to about 150 µM, about 15 µM to about 130 µM, about 15 µM to about 110 µM, about 15 µM to about 90 µM, about 30 µM to about 150 µM, about 30 µM to about 130 µM, about 30 µM to about 110 µM, about 30 µM to about 90 µM, about 30 µM to about 60 µM, about 60 µM to about 150 µM, about 60 µM to about 130 µM, about 60 µM to about 110 µM, or about 60 µM to about 90 µM. In some embodiments, the concentration of pathogen inactivation compound in admixture with the biological fluid prior to illumination is about 10 µM, about 15 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM, about 95 µM, about 100 µM, about 110 µM, about 120 µM, about 130 µM, about 140 µM, or about 150 µM. In some embodiments, the concentration of pathogen inactivation compound in admixture with the biological fluid after illuminating is at least 3-fold (e.g., at least 4-fold, at least 5-fold, at least 10-fold, or more) less than the concentration of pathogen inactivation compound in admixture with the biological fluid prior to illuminating (e.g., without further processing to remove residual pathogen inactivation compound, such as prior to any subsequent compound removal step, e.g., subjecting the biological fluid to a CAD).

Further provided herein is a pathogen inactivated biological fluid prepared by the methods according to any of the above embodiments. In some embodiments, the biological fluid comprises 5 µM or less (e.g., 4 µM or less, 3 µM or less, 2 µM or less, 1 µM or less, 0.5 µM or less) of pathogen inactivation compound after illuminating (e.g., prior to any subsequent compound removal step).

Further provided here are methods for treating a biological fluid comprising: providing a biological fluid in admixture with a photoactive pathogen inactivation compound; and illuminating the biological fluid with ultraviolet light with a first peak wavelength of from about 315 nm to about 350 nm emitted by a set of one or more first light sources, wherein each of the one or more first light sources emits light having a full-width half-maximum (FWHM) spectral bandwidth of less than 20 nanometers, and wherein illuminating the biological fluid occurs for a duration and at an intensity sufficient to inactivate a pathogen in the biological fluid.

In some embodiments, the first peak wavelength is from about 315 to about 335 nm. In some embodiments, the first peak wavelength is from about 330 nanometers to about 350 nanometers. In some embodiments, the first peak wavelength is a peak wavelength of one first light source of the set of one or more first light sources. In some embodiments, the first peak wavelength is a peak wavelength of each of a plurality of first light sources of the set of one or more first light sources. In some embodiments, the first peak wavelength is the average peak wavelength of the set of one or more first light sources.

In some embodiments, the methods further comprise illuminating the biological fluid with ultraviolet light with a second peak wavelength emitted by a set of one or more second light sources, wherein each of the one or more second light sources emits light having a full-width half-maximum (FWHM) spectral bandwidth of less than 20 nanometers, and wherein the second peak wavelength differs from first peak wavelength by at least 5 nm. In some embodiments, the second peak wavelength is a peak wavelength of one second light source of the set of one or more second light sources. In some embodiments, the second peak wavelength is a peak wavelength of each of a plurality of second light sources of the set of one or more second light sources. In some embodiments, the second peak wavelength is the average peak wavelength of the set of one or more second light sources.

In some embodiments, the set of one or more first light sources comprises one or more LEDs. In some embodiments, the biological fluid is contained within a container, and the set of one or more first light sources is disposed as an array of light sources, the set of one or more first light sources facing only one side of the container. In some embodiments, the photoactive pathogen inactivation compound is a psoralen. In some embodiments, the photoactive pathogen inactivation compound is amotosalen.

In some embodiments, the methods further comprise, prior to illuminating the biological fluid with the ultraviolet light with the first peak wavelength: introducing the biological fluid in admixture with the photoactive pathogen inactivation compound into a treatment chamber, the treatment chamber comprising one or more light sensors configured to detect light in the treatment chamber and a first array of light sources configured to illuminate the biological fluid in the treatment chamber, wherein the first array of light sources comprises a first light source channel comprising the set of one or more first light sources, wherein illuminating the biological fluid comprises emitting light with the first peak wavelength from the first light source channel for a first duration and at first intensity sufficient to inactivate a pathogen in the biological fluid. In some embodiments, each light source of the first light source channel is configured to emit ultraviolet light with a first peak wavelength between about 315 nm and about 350 nm. In some embodiments, the methods further comprise: determining a set of characteristics of the biological fluid; determining a treatment profile based on the set of characteristics of the biological fluid; and adjusting or setting a set of parameters of the treatment chamber in accordance with the treatment profile. In some embodiments, illuminating the biological fluid is performed in accordance with the treatment profile, and the first duration and the first intensity sufficient to inactivate the pathogen are determined from the treatment profile. In some embodiments, the first array of light sources comprises a second light source channel configured to emit light of a second peak wavelength. In some embodiments, the second peak wavelength differs from the first peak wavelength by at least 5 nm. In some embodiments, the second peak wavelength is in an ultraviolet A, ultraviolet B, or ultraviolet C spectrum. In some embodiments, the second light source channel comprises a set of one or more second light sources, wherein each of the one or more second light sources emits light having a full-width half-maximum (FWHM) spectral bandwidth of less than 20 nanometers. In some embodiments, the set of characteristics of the biological fluid includes one or more of a group comprising: a volume of the biological fluid, a type of the biological fluid, and a temperature of the biological fluid. In some embodiments, determining the treatment profile based on the set of characteristics of the biological fluid comprises determining the first intensity of light with the first peak wavelength or determining the first duration of emission of light with the first peak wavelength. In some embodiments, the treatment chamber further comprises a first platform positioned in the treatment chamber, the first platform carrying the biological fluid. In some embodiments, adjusting or setting the set of parameters of the treatment chamber comprises adjusting or setting a distance between the first array of light sources and the first platform.

In some embodiments, the methods further comprise agitating the biological fluid. In some embodiments, a total dose of ultraviolet light illuminating the biological fluid is about 0.5 J/cm$^2$ to about 50 J/cm$^2$. In some embodiments, a total dose of ultraviolet light illuminating the biological fluid emitted by the set of one or more first light sources is about 0.5 J/cm$^2$ to about 50 J/cm$^2$. In some embodiments, the methods for treating are sufficient to inactivate at least 1 log of a pathogen in the biological fluid when present, and the biological fluid after illuminating is suitable for infusion into a subject without further processing to remove residual pathogen inactivation compound or photoproduct(s) thereof. In some embodiments, the methods for treating are sufficient to inactivate at least 1 log (e.g., at least 2 logs, at least 3 logs, at least 4 logs) of a pathogen in the biological fluid when present, and the biological fluid after illuminating is suitable for infusion into a subject without subjecting the biological fluid to a compound removal step (e.g., subjecting the biological fluid to a CAD) to remove residual pathogen inactivation compound or photoproduct(s) thereof. In some embodiments, the methods for treating are sufficient to inactivate at least 1 log (e.g., at least 2 logs, at least 3 logs, at least 4 logs) of a pathogen in the biological fluid when present, and the biological fluid comprises 5 μM or less (e.g., 4 μM or less, 3 μM or less, 2 μM or less, 1 μM or less, 0.5 μM or less) of the pathogen inactivation compound after illuminating. In some embodiments, the methods for treating are sufficient to inactivate at least 1 log (e.g., at least 2 logs, at least 3 logs, at least 4 logs) of a pathogen in the biological fluid when present, and the biological fluid comprises 2 μM or less of the pathogen inactivation compound after illuminating. In some embodiments, a concentration of the pathogen inactivation compound in admixture with the biological fluid prior to illuminating is at least about 10 μM (e.g., at least about 30 μM, at least about 60 μM, at least at least about 90 μM, at least about 110 μM). In some embodiments, a concentration of the pathogen inactivation compound in admixture with the biological fluid prior to illuminating is about 15 μM to about 150 μM (e.g., about 30 μM to about 110 μM, about 60 μM to about 90 μM, about 75 μM). In some embodiments, a concentration of the pathogen inactivation compound in admixture with the biological fluid after illuminating is at least 3-fold less than the concentration of pathogen inactivation compound in admixture with the biological fluid prior to illuminating. In some embodiments, the methods for treating are sufficient to inactivate at least 4 log of a pathogen in the biological fluid when present. In some embodiments, the method for treating is sufficient to inactivate at least about 4 log of a pathogen when present, wherein a concentration of the pathogen inactivation compound in admixture with the biological fluid prior to illuminating is about 30 μM to about 110 μM, and wherein the biological fluid comprises about 5 μM or less of PIC, after illumination. In some embodiments, the method for treating is sufficient to inactivate at least about 4 log of a pathogen when present, wherein a concentration of the pathogen inactivation compound in admixture with the biological fluid prior to illuminating is about 30 μM to about 110 μM, and wherein the biological fluid comprises about 2 μM or less of PIC, after illumination. In some embodiments, the biological fluid after illuminating maintains sufficient biological activity so that the biological fluid is suitable for infusion into a subject.

In some embodiments, the biological fluid comprises a blood product. In some embodiments, the biological fluid comprises a plasma composition. In some embodiments, the concentration of fibrinogen in the plasma composition after illuminating is at least 70% of the concentration of fibrinogen in the plasma composition prior to illuminating. In some embodiments, the concentration of factor VIII in the plasma composition after illuminating is at least 70% of the concentration of factor VIII in the plasma composition prior to illuminating. In some embodiments, the concentration of factor II, factor V, factor X, factor XI, Protein C and/or Protein S in the plasma composition after illuminating is at least 70% of the concentration of the corresponding factor II, factor V, factor X, factor XI, Protein C and/or Protein S in the plasma composition prior to illuminating.

In some embodiments, the biological fluid comprises a platelet composition. In some embodiments, the biological fluid further comprises a platelet additive solution. In some embodiments, the amount of platelets in the platelet composition after illuminating is at least 80% platelet recovery. In some embodiments, the platelet recovery of the platelet composition after illuminating is at least 80% (e.g., at least 80% of the platelet composition prior to illuminating). In some embodiments, the pH at 22° C. of the platelet composition after illuminating (e.g., after treating) is at least 6.2 (e.g., at least 6.4, at 5 days after illuminating, at 7 days after illuminating). In some embodiments, the methods comprise, prior to illuminating, incubating the biological fluid with the photoactive pathogen inactivation compound for a period of from 30 minutes to 24 hours (e.g., about 2 hours, 4 hours, 6 hours, 8 hours, 10 hours, 12 hours, 16 hours, 20 hours, 24 hours).

Further provided herein is a pathogen inactivated biological fluid prepared by the methods according to any of the above embodiments. In some embodiments, the pathogen inactivated biological fluid comprises 5 µM or less of the pathogen inactivation compound. In some embodiments, the pathogen inactivated biological fluid comprises 2 µM or less of the pathogen inactivation compound.

Further provided herein are systems for treating a biological fluid, the systems comprising: a treatment chamber configured to receive a biological fluid; one or more sensors configured to detect light in the treatment chamber; and a first array of light sources positioned to illuminate the biological fluid in the treatment chamber, wherein the first array of light sources comprises a first light source channel configured to emit ultraviolet light with a first peak wavelength of the first array of from about 315 nm to about 350 nm, and wherein the first light source channel comprises one or more light sources, each of which emits light having a full-width half-maximum (FWHM) spectral bandwidth of less than 20 nanometers.

In some embodiments, the first peak wavelength of the first array is from about 315 nm to about 335 nm. In some embodiments, the first peak wavelength of the first array is from about 330 nm to about 350 nm. In some embodiments, the first peak wavelength of the first array is the average peak wavelength of the one or more light sources of the first light source channel. In some embodiments, the one or more light sources of the first light source channel comprises one or more light emitting diodes (LEDs). In some embodiments, the first array of light sources further comprises a second light source channel configured to emit light with a second peak wavelength of the first array, wherein the second light source channel comprises one or more light sources, each of which emits light having a full-width half-maximum (FWHM) spectral bandwidth of less than 20 nanometers, and wherein the second peak wavelength of the first array differs from the first peak wavelength of the first array by at least 5 nanometers. In some embodiments, the second peak wavelength of the first array is in an ultraviolet A, ultraviolet B, or ultraviolet C spectrum In some embodiments, the second light source channel comprises one or more LEDs.

In some embodiments, light sources of the first array of light sources are positioned in a non-uniform distribution on the array. In some embodiments, the systems are configured to agitate the biological fluid during treatment. In some embodiments, the first array of light sources comprises two or more panels of light sources. In some embodiments, the first array is configured such that light sources of the first array illuminate the biological fluid in the treatment chamber with less than 25% variance in irradiance across a surface of the biological fluid facing the first array.

In some embodiments, the systems further comprise a first platform positioned in the treatment chamber, the first platform configured to carry the biological fluid. In some embodiments, the first platform and the first array of light sources are configured to translate relative to each other to vary a distance between the first array of light sources and the first platform. In some embodiments, the first platform is slidably moveable for introducing and removing the biological fluid into and out of the treatment chamber. In some embodiments, the first platform is configured to separately hold at least a first container with the biological fluid as a first container biological fluid and a second container with a second container biological fluid. In some embodiments, one or more of the one or more sensors are affixed to or positioned in the first platform.

In some embodiments, the systems further comprise a barrier positioned in the treatment chamber between the first array of light sources and the biological fluid. In some embodiments, the barrier positioned in the treatment chamber between the first array of light sources and the biological fluid is transparent to light with a wavelength within 30 nm of the first peak wavelength of the first array. In some embodiments, one or more of the one or more sensors are affixed to or positioned in the barrier positioned in the treatment chamber between the first array of light sources and the biological fluid. In some embodiments, the first array comprises: a first region of light sources configured to illuminate the biological fluid as a first illuminated biological fluid in the treatment chamber and a second region of light sources configured to illuminate a second illuminated biological fluid in the treatment chamber.

In some embodiments, the systems further comprise control circuitry. In some embodiments, the control circuitry is configured to adjust or set an intensity of or a duration of emission of light from each light source of the first array of light sources. In some embodiments, the control circuitry is configured to adjust or set the intensity of or the duration of emission of light from each light source of the first array of light sources based at least in part on a first set of parameters detected by at least one sensor of the one or more sensors configured to detect light. In some embodiments, the systems further comprise one or more sensors configured to detect the presence of a biological fluid within the treatment chamber.

In some embodiments, the systems further comprise a second array of light sources facing an opposite direction as the first array of light sources, wherein the second array of light sources comprises a first light source channel configured to emit light of a first peak wavelength of the second array, and wherein the first light source channel of the second array comprises one or more light sources, each of which emits light having a full-width half-maximum (FWHM) spectral bandwidth of less than 20 nanometers. In some embodiments, the first peak wavelength of the second array is substantially the same as the first peak wavelength of the first array. In some embodiments, the second array of light sources comprises a second light source channel configured to emit light of a second peak wavelength of the second array, wherein the second light source channel of the second array comprises one or more light sources, each of which emits light having a full-width half-maximum (FWHM) spectral bandwidth of less than 20 nanometers, and wherein the second peak wavelength of the second array differs from the first peak wavelength of the second array by at least 5 nanometers. In some embodiments, the first array of light sources and the second array of light sources are configured to translate relative to each other to vary a distance between the first array of light sources and the second array of light sources. In some embodiments, the systems further comprise a second array of light sources facing a same direction as the first array of light sources, wherein the second array of light sources comprises a first light source channel configured to emit light of a first peak wavelength of the second array, and wherein the first array of light sources and the second array of light sources define a first region between the first array of light sources and the second array of light sources, and wherein first light source channel of the second array comprises one or more light sources, each of which emits light having a full-width half-maximum (FWHM) spectral bandwidth of less than 20 nanometers.

In some embodiments, the systems further comprise a first platform positioned in the treatment chamber between the first array of light sources and the second array of light sources, the first platform configured to carry the biological fluid. In some embodiments, the systems further comprise: a first platform positioned in the treatment chamber in the first region, the first platform configured to carry the biological fluid as a first carried biological fluid; and a second platform positioned in the treatment chamber outside the first region, the second platform configured to carry a second carried biological fluid, wherein the second array of light sources faces the second platform. In some embodiments, one or more of the one or more sensors are affixed to or positioned in the second platform.

In some embodiments, the systems further comprise a barrier positioned in the treatment chamber between the second array of light sources and a biological fluid. In some embodiments, the barrier positioned in the treatment chamber between the second array of light sources and a biological fluid is transparent to light with a wavelength within 30 nm of the first peak wavelength of the first array. In some embodiments, one or more of the one or more sensors are affixed to or positioned in the barrier positioned in the treatment chamber between the second array of light sources and a biological fluid.

In some embodiments, the systems further comprise control circuitry configured to adjust or set an intensity of or a duration of emission of light from each light source of the second array of light sources. In some embodiments, the control circuitry is configured to adjust or set the intensity of or the duration of emission of light from each light source of the second array of light sources based at least in part on a first set of parameters detected by at least one sensor of the one or more sensors configured to detect light. In some embodiments, the control circuitry is configured to a) determine a set of characteristics of the biological fluid; b) determine a treatment profile based on the set of characteristics of the biological fluid; c) adjust or set a set of parameters of the treatment chamber in accordance with the treatment profile; and d) illuminate the biological fluid in accordance with the treatment profile.

In some embodiments, the systems are configured to illuminate the biological fluid in admixture with a photoactive pathogen inactivation compound for a duration and at an intensity sufficient to inactivate a pathogen in the biological fluid when present. In some embodiments, the system are configured to illuminate the biological fluid in admixture with a photoactive pathogen inactivation compound for a duration and at an intensity sufficient to inactivate at least 1 log a pathogen in the biological fluid when present, and the biological fluid after illuminating is suitable for infusion into a subject without further processing to remove residual photoactive pathogen inactivation compound or photoproduct(s) thereof. In some embodiments, the system are configured to illuminate the biological fluid in admixture with a photoactive pathogen inactivation compound for a duration and at an intensity sufficient to inactivate at least 1 log of a pathogen in the biological fluid when present, and the biological fluid comprises 5 µM or less of photoactive pathogen inactivation compound after illuminating. In some embodiments, the system are configured to illuminate the biological fluid in admixture with a photoactive pathogen inactivation compound for a duration and at an intensity sufficient to reduce the concentration of the photoactive pathogen inactivation compound in admixture with the biological fluid by at least 3-fold relative to the concentration of photoactive pathogen inactivation compound in admixture with the biological fluid prior to illuminating. In some embodiments, the system are configured to illuminate the biological fluid in admixture with a photoactive pathogen inactivation compound for a duration and at an intensity sufficient to inactivate at least 4 log of a pathogen in the biological fluid when present.

In some embodiments, the biological fluid comprises a blood product. In some embodiments, the biological fluid comprises a plasma composition. In some embodiments, the biological fluid comprises a platelet composition. In some embodiments, the biological fluid further comprises a platelet additive solution. In some embodiments, the photoactive pathogen inactivation compound is a psoralen. In some embodiments, the photoactive pathogen inactivation compound is amotosalen.

BRIEF DESCRIPTION OF THE DRAWINGS

FIG. 5 is a perspective view of an exemplary system for treating biological fluids comprising multiple light source arrays facing the same direction.

FIGS. 6A-6B are perspective views of an exemplary system for treating biological fluids comprising a light source array facing a platform for biological fluids.

FIG. 9 illustrates exemplary spectral outputs for a broad band fluorescent bulb UV light source and narrow band LED UV light sources.

DETAILED DESCRIPTION

The following description is presented to enable a person of ordinary skill in the art to make and use the various embodiments. Descriptions of specific systems, devices, methods, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Biological fluids, such as for example blood and blood products, may contain contaminating pathogen(s) due to an infected donor, or introduction of pathogen(s) during processing. As such, it may be desirable to subject such biological fluids to a treatment process (e.g., pathogen inactivation, pathogen reduction) that reduces the risk of contaminating pathogens. Ideally, such a process results in the inactivation of a broad range of pathogens (e.g., viruses, bacteria, parasites) that may be present in the biological fluid. The treatment process may also inactivate other undesirable substances, such as for example cells (e.g., leukocytes) and nucleic acids that may be present in the biological fluid.

Advantageously, the present disclosure demonstrates methods and systems that unexpectedly provide a higher level of virus and/or bacterial inactivation (e.g., photochemical inactivation) with more efficient photoconversion of pathogen inactivation compounds, such as for example psoralen pathogen inactivation compounds (e.g., S-59). In some embodiments, the methods and systems may be sufficient to inactivate at least 1 log (at least 2 logs, at least 3 logs, at least 4 logs) of a pathogen in the biological fluid, and provide a pathogen-inactivated biological fluid (e.g., blood product) with sufficient photoconversion of the pathogen inactivation compound after illuminating that the biological fluid is suitable for infusion into a subject without further processing to remove residual pathogen inactivation compound or photoproducts thereof.

In some embodiments, the photoconversion of the pathogen inactivation compound (e.g., S-59) is determined as % (e.g., concentration, weight %) of the compound remaining after illumination relative to the amount (e.g., concentration, weight %) of input pathogen inactivation compound. In some embodiments, the % of the compound remaining after illumination is less than about 40%, less than about 35%, less than about 30%, less than about 25%, less than about 20%, less than about 15%, less than about 10%, or less than about 5%. In some embodiments, photoconversion of the pathogen inactivation compound is determined as the concentration (e.g., µM concentration) of residual pathogen inactivation compound remaining after illumination.

Figure 1A:
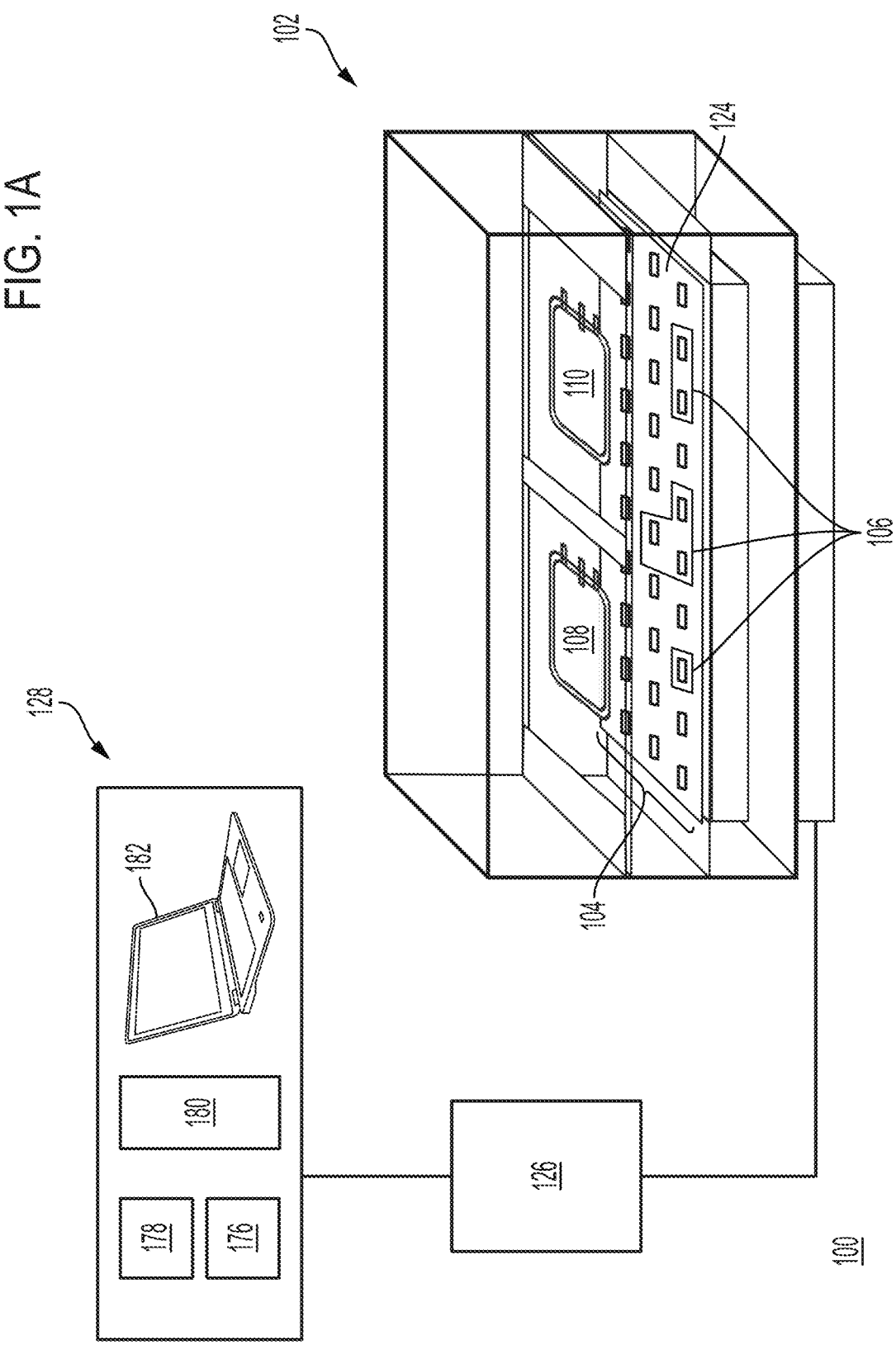
FIGS. 1A-1E show perspective views of an exemplary system for treating biological fluids.

FIG. 1A is a perspective view of an exemplary system 100 for treating a biological fluid. As used herein, a "biological fluid" refers to any fluid that is found in or derived from an organism (e.g., human, animal, plant, microorganism), or that comprises one or more components (e.g., biologics) found in, isolated from, or derived from an organism, including synthetic versions thereof. Biological fluids may include, but are not limited to, blood and blood products, vaccines, cells (e.g., primary cells, cell lines, cell cultures), natural and recombinant proteins (e.g., therapeutics, antibodies), bacterial cultures, virus suspensions and the like. As used herein, "blood product" refers to blood (e.g., whole blood) or a component or derivative of blood such as, for example, red blood cells, white blood cells, platelets, plasma, cryoprecipitate and cryo-poor (e.g., cryo-reduced) plasma, or a combination of one or more of such components that have been separated from blood. In some embodiments, a biological fluid may further comprise a non-biological fluid, such as for example, a physiological solution (e.g., diluent solution), including but not limited to saline, buffered solution, nutrient solution, platelet additive solution (PAS) and/or anticoagulant solution. In some embodiments, the biological fluid comprises a volume of about 50 mL to about 1000 mL (e.g., about 100 mL to about 750 mL, about 200 mL to about 600 mL, about 100 mL, about 200 mL, about 300 mL, about 400 mL, about 500 mL, about 600 mL).

In some embodiments, treatment system 100 may be used to inactivate pathogen(s) in one or more biological fluids, preferably biological fluids admixed with one or more pathogen inactivation compounds (e.g., photoactive pathogen inactivation compound, psoralen). In particular, treatment system 100 may illuminate a mixture of one or more pathogen inactivation compounds and a biological fluid with light (e.g., ultraviolet light) of certain wavelengths to cause a photochemical reaction and inactivate pathogens, such as viruses, bacteria, parasites and other contaminants, such as for example, cell contaminants (e.g., leukocytes) that may be present in the biological fluid. In some embodiments, treatment system 100 may illuminate a mixture of one or more pathogen inactivation compounds and a biological fluid having a volume of about 50 mL to about 1000 mL (e.g., about 100 mL to about 750 mL).

In some embodiments, after the treatment system 100 illuminates a mixture of one or more pathogen inactivation compounds and a biological fluid with light (e.g., ultraviolet light, ultraviolet A light) of certain wavelengths (e.g., about 315 nm to about 350 nm, about 315 nm to about 335 nm, about 330 nm to about 350 nm) to cause a photochemical reaction and inactivate pathogens, the biological fluid is suitable for infusion into a subject without further processing, including without exposure to a compound adsorption device (CAD), to remove residual components useful for photochemical inactivation of pathogens, such as a pathogen inactivating compound (PIC), or photoproducts thereof. In some embodiments, after the treatment system 100 illuminates a mixture of one or more pathogen inactivation compounds and a biological fluid with light (e.g., ultraviolet light) of certain wavelengths (e.g., about 315 nm to about 350 nm, about 315 nm to about 335 nm, about 330 nm to about 350 nm) to cause a photochemical reaction and inactivate pathogens, the biological fluid comprises less than 5 µM of PIC (e.g., less than 2 µM of PIC).

The term "pathogen inactivation compound" means any suitable compound, such as a small organic compound, that can be used to inactivate a pathogen that may be present in a biological fluid, such as for example, blood or a blood product. A pathogen inactivation compound that is a "photoactive" or "photoactivated" or "photochemical" or "photosensitizer" compound is a suitable compound that requires some level of light in order to sufficiently inactivate a pathogen. Such compounds are preferred in the inactivation of pathogens in biological products as they provide control over the inactivation process. In some embodiments, the pathogen inactivating compound is a photoactive pathogen inactivating compound selected from the group consisting of a psoralen, an isoalloxazine, an alloxazine, a phthalocyanine, a phenothiazine, a porphyrin, and merocyanine 540. In some embodiments, the pathogen inactivating compound is a psoralen. In some embodiments, the pathogen inactivating compound is amotosalen (e.g., S-59). Such photoactivated or photochemical pathogen inactivation compounds as described herein may include, but are not limited to, psoralens, isoalloxazines, alloxazines, phthalocyanines, phenothiazines, and porphyrins, where these terms are understood to encompass a general class of compounds, i.e. the core compound and suitable derivatives thereof. For example psoralens or a psoralen generally describes the psoralen core compound and any derivative thereof (e.g. amotosalen), isoalloxazines or an isoalloxazine generally describes the isoalloxazine core and any derivative thereof (e.g. riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 4'-(4-amino-2-oxa)butyl-4,5',8-trimethyl psoralen. Where the methods of the present disclosure include adding amotosalen HCl (the HCl salt of amotosalen), the removal of this compound from the biological fluid, such as for example a blood product (e.g., platelet composition, unit of platelets, plasma composition, whole blood composition, plasma composition) is not limited to the removal of amotosalen HCl, as the amotosalen can be present in solution as other salts or as the free base. As used in the methods described herein, removal of amotosalen means removal of the compound in any form, e.g. as the free base or as any salt, as measured by the assays described herein.

In some embodiments, the pathogen inactivation compound is a 4-primaryamino-substituted psoralen, which is a psoralen compound having an $NH_2$ group linked to the 4'-position of the psoralen by a hydrocarbon chain having a total length of 2 to 20 carbons, where 0 to 6 of those carbons are independently replaced by NH or O, and each point of replacement is separated from each other point of replacement by at least two carbons, and is separated from the psoralen by at least one carbon. 4'-primaryamino-substituted psoralens may have additional substitutions on the 4,5', and 8 positions of the psoralen, said substitutions include, but are not limited to, the following groups: H and $(CH_2)_nCH_3$, where n=0-6. In some embodiments, the 4'-primaryamino-substituted psoralen comprises: a) a substituent $R_1$ on the 4' carbon atom, selected from the group comprising: $—(CH_2)_u—NH_2$, $—(CH_2)_w—R_2—(CH_2)_z—NH_2$, $—(CH_2)_w—R_2—(CH_2)_x—R_3—(CH_2)_z—NH_2$, and $—(CH_2)_w—R_2—(CH_2)_x—R_3—(CH_2)_y—R_4—(CH_2)_z—NH_2$; wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4,5', and 8 carbon atoms respectively, independently selected from the group comprising H and $(CH_2)_vCH_3$, where v is a whole number from 0 to 5; or a salt thereof.

In some embodiments, the pathogen inactivation compound is a 5-primaryamino-substituted psoralen, which is a psoralen compound having an $NH_2$ group linked to the 5'-position of the psoralen by a hydrocarbon chain having a total length of 1 to 20 carbons, where 0 to 6 of those carbons are independently replaced by NH or O, and each point of replacement is separated from each other point of replacement by at least two carbons, and is separated from the psoralen by at least one carbon. 5'-primaryamino-substituted psoralens may have additional substitutions on the 4,4', and 8 positions of the psoralen, said substitutions include, but are not limited to, the following groups: H and $(CH_2)_nCH_3$, where n=0-6. In some embodiments, the 5'-primaryamino-substituted psoralen comprises: a) a substituent $R_1$ on the 5' carbon atom, selected from the group comprising: $—(CH_2)_u—NH_2$, $—(CH_2)_w—R_2—(CH_2)_z—NH_2$, $—(CH_2)_w—R_2—(CH_2)_x—R_3—(CH_2)_z—NH_2$, and $—(CH_2)_w—R_2—(CH_2)_x—R_3—(CH_2)_y—R_4—(CH_2)_z—NH_2$; wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5, where when $R_1$ is selected from the group comprising $—(CH_2)_u—NH_2$, $R_7$ is $(CH_2)_vCH_3$, and where when $R_5$, $R_6$, and $R_7$ are $(CH^2)_vCH_3$, u is a whole number from 3 to 10; or a salt thereof. Exemplary psoralen compounds are described, e.g., in U.S. Pat. No. 5,593,823.

In some embodiments, the biological fluid (e.g., platelet composition) is in admixture with a pathogen inactivation compound (PIC) in a platelet additive solution (PAS). In some embodiments, the PIC is admixed with the PAS prior to admixing with the biological fluid. Platelet additive solutions are known in the art, for example, as described by Alhumaidan et al. and Ringwald et al. (Alhumaidan, H. and Sweeney, J., *J Clin Apheresis*, 27: 93-98 (2012); Ringwald et al., *Transfusion Medicine Reviews*, 20: 158-64 (2006)), which are hereby incorporated by reference in their entirety. In some embodiments, the platelet additive solution (PAS) comprises one or more of chloride, acetate, citrate, potassium, magnesium, phosphate, gluconate, glucose, and bicarbonate. In some embodiments, the platelet additive solution (PAS) is a PAS approved by a regulatory agency or accrediting organization generally accepted in the field.

In some embodiments, the platelet additive solution (PAS) comprises one or more of sodium chloride, sodium acetate, sodium citrate, potassium chloride, magnesium chloride, sodium phosphate, sodium gluconate, glucose, and sodium bicarbonate.

In some embodiments, the PAS comprises chloride, citrate, phosphate, and potassium. In some embodiments, the PAS comprises chloride, citrate, and acetate. In some embodiments, the PAS comprises chloride, citrate, phosphate, and acetate. In some embodiments, the PAS comprises chloride, citrate, acetate, magnesium, potassium, and gluconate. In some embodiments, the PAS comprises chloride, citrate, phosphate, acetate, magnesium, and potassium. In some embodiments, the PAS comprises chloride, acetate, magnesium, potassium, and gluconate. In some embodiments, the PAS comprises chloride, citrate, phosphate, acetate, magnesium, potassium, and glucose.

In some embodiments, the PAS comprises sodium chloride, sodium acetate, potassium chloride, magnesium chloride, and sodium gluconate. In some embodiments, the PAS comprises sodium chloride, sodium acetate, and sodium citrate. In some embodiments, the PAS comprises sodium chloride, sodium acetate, sodium citrate, and sodium phosphate. In some embodiments, the PAS comprises sodium chloride, sodium citrate, sodium phosphate, and potassium chloride. In some embodiments, the PAS comprises sodium chloride, sodium acetate, sodium citrate, potassium chloride, magnesium chloride, and sodium phosphate. In some embodiments, the PAS comprises sodium chloride, sodium acetate, sodium citrate, potassium chloride, magnesium chloride, and sodium gluconate. In some embodiments, the PAS comprises sodium chloride, sodium acetate, sodium citrate, potassium chloride, magnesium chloride, sodium phosphate, glucose, and sodium bicarbonate. In some embodiments, the PAS comprises sodium chloride, sodium acetate, sodium citrate, potassium chloride, magnesium chloride, glucose, and sodium bicarbonate.

In some embodiments, the PAS is PAS-I. In some embodiments, the PAS is PlasmaLyte. In some embodiments, the PAS is Pas-II. In some embodiments, the PAS is T-Sol. In some embodiments, the PAS is PAS-III. In some embodiments, the PAS is Intersol. In some embodiments, the PAS is PAS-IIIM SSP. In some embodiments, the PAS is ComposolPAS-G. In some embodiments, the PAS is M-Sol. In some embodiments, the PAS is Isoplate. In some embodiments, the PAS is PAS-A. In some embodiments, the PAS is PAS-B. In some embodiments, the PAS is PAS-C. In some embodiments, the PAS is PAS-D. In some embodiments, the PAS is PAS-E. In some embodiments, the PAS is PAS-F. In some embodiments, the PAS is PAS-G.

In some embodiments, the biological fluid (e.g., plasma composition, platelet composition, platelet composition in PAS) is incubated with the photoactive pathogen inactivation compound prior to illumination: for a period of from 30 minutes to 24 hours (e.g., 2 hours to 24 hours, 4 hours to 24 hours, 8 hours to 24 hours, 12 hours to 24 hours).

Biological fluids, such as for example blood products, including for example, whole blood, red blood cells and platelet-containing and plasma-containing blood products (e.g., platelet composition, plasma composition), may contain pathogens, or may be contaminated with pathogens during processing. As such, it is desirable to subject such biological fluids (e.g., blood products) to a pathogen inactivation process in order to reduce the risk of transfusion-transmitted diseases. Various processes and methods have been used to mitigate the risk of transfusion-associated disease transmission in blood products, such as platelet-containing and plasma-containing blood products. Aside from screening and detection of pathogens and subsequent elimination of contaminated blood products, processes that incorporate treatments to inactivate pathogens (i.e., pathogen inactivation) that may be present are available. Ideally, such a process results in the inactivation of a broad range of pathogens such as viruses, bacteria and parasites that may be present in the blood product. For example, pathogen inactivation may involve the addition of a low molecular weight compound that inactivates various pathogens, where a preferred method involves the addition of a photosensitizer (e.g., photoactive compound, photochemical) that, when activated by illumination using light of suitable wavelengths, will inactivate a variety of pathogens that may be present. Two preferred methods that are commercially available include the addition of amotosalen or riboflavin to the blood product (e.g., platelets, plasma), with subsequent illumination with UV light. Other methods include illumination with UV light without addition of a photosensitizer (e.g., UV germicidal treatment), as well as illumination with other photoactive compounds, including psoralen derivatives other than amotosalen, isoalloxazines other than riboflavin, alloxazines, dyes such as phthalocyanines, phenothiazine dyes (e.g. methylene blue, azure B, azure C, thionine, toluidine blue), porphyrin derivatives (e.g. dihematoporphyrin ether, hematoporphyrin derivatives, benzoporphyrin derivatives, alkyl-substituted sapphyrin), and merocyanine 540 (Prodouz et al., Blood Cells 1992, 18(1):101-14; Sofer, Gail, BioPharm, August 2002). Other pathogen inactivation systems include, for example, those described in International application publication Nos. WO2012071135, WO2012018484, WO2003090794, WO2003049784, WO1998018908, WO1998030327, WO1996008965, WO1996039815, WO1996039820, WO1996040857, WO1993000005, U.S. Patent application No. US20050202395, and U.S. Pat. Nos. 8,296,071 and 6,548,242, the disclosures of which are hereby incorporated by reference as they relate to pathogen inactivation in blood products. In some embodiments, the pathogen inactivating compound is a photoactive pathogen inactivating compound selected from the group consisting of a psoralen, an isoalloxazine, an alloxazine, a phthalocyanine, a phenothiazine, a porphyrin, and merocyanine 540. In some embodiments, the pathogen inactivating compound is a psoralen. In some embodiments, the pathogen inactivating compound is amotosalen. Where addition of a compound to the biological fluid, such as for example, blood products (e.g., platelets, plasma), is used for pathogen inactivation, in some instances it is desirable to remove any residual pathogen inactivation compound or by-product (e.g., photoproduct, degradation product) thereof, such as for example, by more efficient photoconversion of the pathogen inactivation compound.

Some methods used for removal of pathogen inactivation compounds or by-products thereof include the use of a pathogen inactivation compound removal device, e.g., a device for reducing the concentration of pathogen inactivation compound, including a compound adsorption device (CAD), such as a small organic compound, and by-products thereof, in the biological fluid while substantially maintaining a desired biological activity of the biological fluid. In some embodiments, the removal device comprises porous adsorbent particles in an amount sufficient to reduce the pathogen inactivation compound to below a desired concentration, wherein the adsorbent particles have an affinity for the pathogen inactivation compound. A variety of adsorbent particles are known, including generally particles made from any natural or synthetic material capable of interacting with compounds to be removed, including particulates made of natural materials such as activated carbon, silica, diatomaceous earth, and cellulose, and synthetic materials such as hydrophobic resins, hydrophilic resins or ion exchange resins. Such synthetic resins include, for example, carbonaceous materials, polystyrene, polyacrylic, polyacrylic ester, cation exchange resin, and polystyrene-divinylbenzene. Detailed description of such removal devices and adsorbent particlescan be found in International application publication Nos. WO1996040857, WO1998030327, WO1999034914, and WO2003078023, and include, for example, Amberlite (Rohm and Haas) XAD-2, XAD-4, XAD-7, XAD-16, XAD-18, XAD-1180, XAD-1600, XAD-2000, XAD-2010; Amberchrom (Toso Haas) CG-71m, CG-71c, CG-161m, CG161c; Diaion Sepabeads (Mitsubishi Chemicals) HP20, SP206, SP207, SP850, HP2MG, HP20SS, SP20MS; Dowex (Dow Chemical) XUS-40285, XUS-40323, XUS-43493 (also referred to as Optipore V493 (dry form) or Optipore L493 (hydrated form)), Optipore V503, Optipore SD-2; Hypersol Macronet (Purolite) MN-100, MN-102, MN-150, MN-152, MN-170, MN-200, MN-202, MN-250, MN-252, MN-270, MN-300, MN-400, MN-500, MN-502, Purosorb (Purolite) PAD 350, PAD 400, PAD 428, PAD 500, PAD 550, PAD 600, PAD 700, PAD 900, and PAD 950. Materials used to form the immobilized matrix generally comprisea a low melting polymer, such as nylon, polyester, polyethylene, polyamide, polyolefin, polyvinyl alcohol, ethylene vinyl acetate, or polysulfone. In one example, removal devices of an amotosalen inactivated blood product are commercially available, including for example, removal devices containing Hypersol Macronet MN-200 adsorbent contained within a sintered matrix, where the sintered matrix comprises PL2410 plastic as a binder.

Figure 8A:
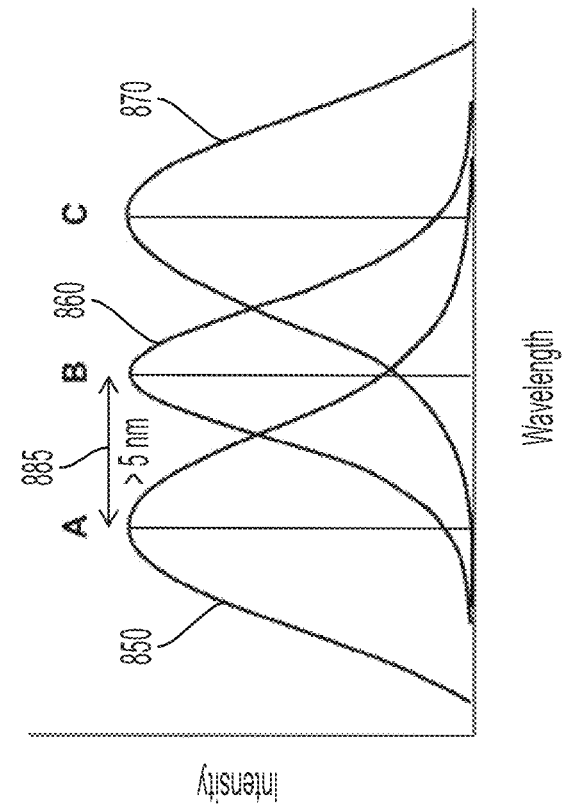
FIG. 8A illustrates an exemplary spectral output for a light source, and indicating wavelength of maximum peak intensity, 50% of maximum peak intensity, and full width at half maximum peak intensity.
Figure 8B:
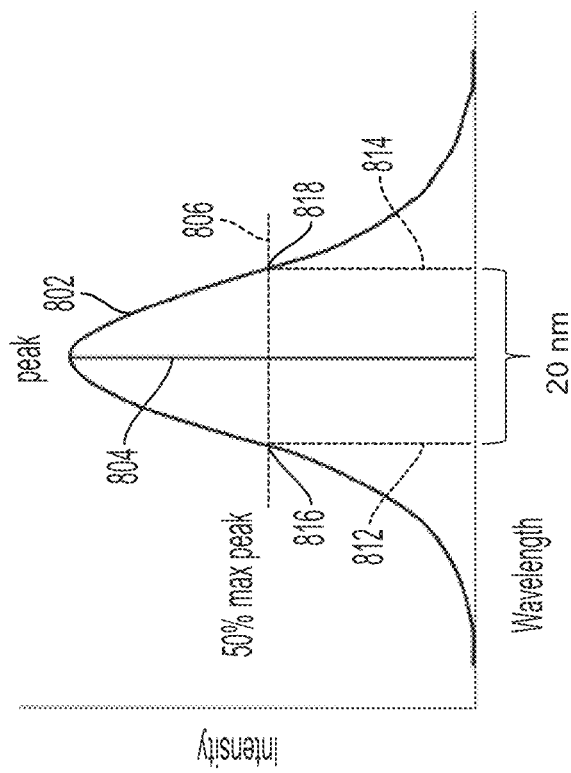
FIG. 8B illustrates exemplary spectral outputs for three light sources with different wavelengths of maximum peak intensity and wavelength distribution.

Inactivating pathogens in a biological fluid may require satisfying various treatment parameters that comprise a treatment profile for a biological fluid. Accordingly, the systems and methods discussed herein may be controlled and used to treat one or more biological fluids in accordance with their one or more respective treatment profiles. As used herein, a treatment profile for a biological fluid refers to a set of treatment parameters required for inactivation of one or more types of pathogens present in the biological fluid. Such parameters may include, but are not limited to, one or more peak wavelengths of light applied to (e.g., one or more peak wavelengths of light that illuminate) the biological fluid, the duration(s) for which one or more peak wavelengths of light are applied to the biological fluid, the intensities at which light of the one or more peak wavelengths are applied to one or more portions of the biological fluid, the energy dosages of the one or more peak wavelengths that are applied to one or more portions of the biological fluid, the angle of incidence at which light is applied to the biological fluid, the temperature during treatment of the biological fluid, the method of agitation/mixing of the biological fluid, the duration for which the biological fluid is agitated or mixed, the distance between light sources that are applied to the biological fluid and the type of biological fluid, and so on. As described herein, the "peak wavelength" of a light source refers to the wavelength at which the maximum intensity of light is emitted by the light source. FIG. 8A illustrates an exemplary spectral output 802 (e.g., spectral curve) for a light source, with the vertical solid line 804 identifying the wavelength of maximum peak intensity (e.g., peak wavelength), as well as a horizontal dashed line 806 representing 50% of the maximum peak intensity, and vertical dashed lines 812 and 814 identifying the points 816 and 818 on either side of the peak at half maximum representing the full-width (e.g., bandwidth) along the wavelength axis between those points (e.g., FWHM, 20 nm full-width, 10 nm half-width from peak). Spectral curves, including for example spectral curves 850, 860, 870 from light sources with similar peak intensities as illustrated in FIG. 8B, may be of symmetrical (B) or asymmetrical (A, C) wavelength distribution, and peak wavelengths of different light sources. Also depicted is an exemplary difference 885 in peak wavelengths (e.g., >5 nm).

Pathogens inactivated by the systems and methods of the present disclosure, may include for example, any number of viruses, bacteria and/or parasites. Exemplary pathogens may include enveloped viruses, non-enveloped viruses, DNA viruses, such as for example, viruses of the families Papillomaviridae, Parvoviridae, Herpesviridae, Poxviridae, Hepadnaviridae, Polyomaviridae, RNA viruses, such as for example, viruses of the families Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae, Retroviridae, the viruses human immunodeficiency virus (e.g., HIV-1), HTLV-1, HTLV-2, adenovirus, hepatitis A virus, hepatitis B virus, hepatitis C virus, yellow fever virus, Zika virus, hepatitis D virus, hepatitis E virus, West Nile virus, Lassa virus, Ebola virus, Marburg virus, alphaviruses (e.g., chikungunya virus), Epstein-Barr virus, dengue virus, cytomegalovirus, BK virus, influenza virus, blue tongue virus and/or adenovirus. Exemplary pathogens may include Gram positive bacteria, Gram negative bacteria, anaerobic bacteria, *Escherichia* (e.g., *E. coli*), *Yersinia* (e.g., *Y. enterocolitica*), *Klebsiella* (e.g., *K pneumoniae*), *Serratia* (e.g., *S. marcescens*), *Staphylococcus* (e.g., *S. epidermidis, S. aureus*), *Streptococcus* (e.g., *S. pyogenes*), *Bacillus* (e.g., *B. cereus*), *Clostridium* (e.g., *C. perfringens*), *Propionibacterium* (e.g., *P. acnes*), *Treponema* (e.g., *T. pallidum*), Borrrelia (e.g., *B. burgdorferi*), *Listeria* (e.g., *L. monocytogenes*), *Pseudomonas* (e.g., *P. aeruginosa*), *Haemophilus* (e.g., *H. parainfluenzae*), *Rickettsia* (e.g., *R. rickettsia*), *Anaplasma* (e.g., A. phagocytophilium), *Acinetobacter* (e.g., *A. baumannii*). Exemplary pathogens may also include the parasites *Plasmodium* (e.g., *Plasmodium falciparum*), *Babesia* (e.g., *Babesia microti*), *Trypanosoma* (e.g., *Trypanosoma cruzi*). *Leishmania* (e.g., *Leishmania braziliensis*). Additionally, the systems and methods of the present disclosure may inactivate one or more undesirable cell types, such as for example, leukocytes, in a biological fluid. It should be understood that treatment of a biological fluid to inactivate pathogens that may be present does not necessarily inactivate completely all pathogens that may be present, but substantially reduces the amount of pathogens to significantly reduce the risk arising from the presence of a pathogen (e.g., transfusion associated disease from a blood product, transfusion transmitted infection from a blood product). The inactivation of a pathogen may be assayed by measuring the number of infective pathogens (e.g., viral particles, bacteria) in a certain volume, and the level of inactivation is typically represented in the log reduction in the infectivity of the pathogen, or log reduction in titer. Methods of assaying log reduction in titer, and measurements thereof to assess levels of pathogen inactivation are well known in the art. When the inactivation process is tested against a variety of pathogens, the reduction in a particular pathogen is at least about 1 log, at least about 2 log, at least about 3 log, at least about 4 log, or at least about 5 log or more reduction in titer. Such pathogen inactivated biological fluid, in addition to use for treatment (e.g., transfusion, therapy) of a subject in need thereof, may also be further processed for other uses, for example further processing to provide a product derived from the biological fluid, such as for example, a platelet lysate product from a pathogen inactivated platelet preparation or a cryoprecipitate from a pathogen-inactivated plasma preparation.

Turning to FIG. 1A, exemplary system 100 for treating biological fluids includes a treatment chamber 102 for receiving one or more biological fluids 108 and 110 and an array of light sources 104 positioned to illuminate one or more biological fluids 108 and 110. In some embodiments, the array of light sources 104 may comprise the only light sources in chamber 102 positioned to illuminate the one or more biological fluids 108 and 110. In other embodiments described below with respect to FIGS. 3-5, multiple light source arrays may be used to illuminate one or more biological fluids positioned in various embodiments of chamber 102. As described herein, an "array of light sources" means one or more light sources disposed on any two or three dimensional surface (e.g., contiguous surface, non-contiguous surface).

One or more light source channels 106 are included in array of light sources 104. Each light source channel 106 may be a set of one or more light sources having the same wavelength (e.g., peak wavelength). In an exemplary set, one light source may have a peak wavelength. In another exemplary set, two light sources may have the same peak wavelength to each other. In yet another exemplary set, each of a plurality of light sources may have different peak wavelengths from each other. In a further exemplary set, a first subset of one or more light sources may have one peak wavelength, and a second subset of one or more light sources may have a different peak wavelength. Within a light source channel having a plurality of light sources, all of the light sources may have respective peak wavelengths that all are within a wavelength range (e.g., range of 1-20 nm; e.g., 1 nm, 2 nm, 3 nm, 4 nm, 5 nm or more, greater than and/or less than a particular wavelength) for the light source channel. For example, in some embodiments, within a light source channel having a plurality of light sources, all of the light sources may have peak wavelengths within a range set forth in the present disclosure, such as for example of about 315 nm to about 350 nm (e.g., about 315 nm to about 335 nm, about 330 nm to about 350 nm). In light source channel 106, each light source may be any light source providing light of a desirable property (e.g., peak wavelength, spectral bandwidth) including, but not limited to, solid-state lighting (SSL), light-emitting diodes (LEDs), organic light-emitting diodes (OLEDs), polymer light-emitting diodes (PLEDs), and laser diodes. The light source channels 106 of the array of light sources 104 may be connected in a series circuit, in a parallel circuit, or in a combination of series and parallel circuits. In a light source channel 106 having a plurality of light sources, those light sources may be controlled together or separately.

Each light source channel 106 may be tilted (e.g., adjustably tilted) with respect to a normal direction of a surface (e.g., perpendicular to a surface) each light source channel 106 is disposed on. For example, each light source channel 106 may be tilted at an angle of >0° to about 50°, such as for example to about 45°, 40°, 35° 30°, 25°, 20°, 15°, 10°, 5°, 4°, 3°, 2° or to about 1°, or <50°, <45°, <40°, <35°, <30°, <25°, <20°, <15°, <10°, <50°, <40°, <30°, <2°, or <1° with respect to a normal direction of surface 124 defined by the plane of array of light sources 104. Each light source channel 106 (e.g., light source therein) may be independently tilted, for example, whereby one or more light source channels 106 (e.g., light source(s) therein) are tilted at an angle different from one or more other light source channels 106 (e.g., light source(s) therein). Tilting the one or more light source channels 106 may be desirable to control the intensity of light and/or the angle of incidence of light that illuminates biological fluids 108 and 110.

Each light source channel 106 may be adjusted or set to emit light at different intensities (e.g., adjust the light dosage, adjust the energy dosage) at which light of the one or more peak wavelengths are applied to one or more portions of the biological fluid. For example, each light source channel may emit light at maximum intensity (e.g., 100%), or at less than maximum intensity (e.g., about 90%, about 80%, about 70%, about 60%, about 50%, about 40%, about 30%, about 20%, or less).

Each light source channel 106 may emit various types of light. For example, each light source channel may emit ultraviolet light, ultraviolet A light, ultraviolet B light, ultraviolet C light, and/or visible light. Additionally, each light source channel 106 may emit light of various peak wavelengths. For example, the emitted peak wavelength(s) may be in the ultraviolet A spectrum (e.g., 315-400 nm), the ultraviolet B spectrum (e.g., 280-315 nm), the ultraviolet C spectrum (e.g., 100-280 nm, 200-280 nm, 240-280 nm), or the visible light spectrum (e.g., 400-800 nm). In some embodiments, the emitted peak wavelength(s) may be between about 240 nm and about 250 nm, about 245 nm and about 255 nm, about 250 nm and about 260 nm, about 255 nm and about 265 nm, about 260 nm and about 270 nm, about 265 nm and about 275 nm, about 270 nm and about 280 nm, or about 275 nm and about 285 nm. In some embodiments, the emitted peak wavelength(s) may be between about 280 nm and about 290 nm, about 285 nm and about 295 nm, about 290 nm and about 300 nm, about 300 nm and about 310 nm, about 305 nm and about 315 nm, or about 310 nm and about 320 nm. In some embodiments, the emitted peak wavelength(s) may be between about 315 nm and about 325 nm, about 320 nm and about 330 nm, about 325 nm and about 335 nm, about 330 nm and about 340 nm, about 335 nm and about 345 nm, about 340 nm and about 350 nm, about 345 nm and about 355 nm, about 350 nm and about 360 nm, about 355 nm and about 365 nm, about 360 nm and about 370 nm, about 365 nm and about 375 nm, about 370 nm and about 380 nm, about 375 nm and about 385 nm, about 380 nm and about 390 nm, about 385 nm and about 395 nm, about 390 nm and about 400 nm. In some embodiments, the emitted peak wavelength may be about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, or about 400 nm. In some embodiments, the emitted peak wavelength may be between about 255 nm and about 275 nm (e.g., between about 260 nm and about 270 nm, 265 nm). In some embodiments, the emitted peak wavelength may be between about 275 nm and about 295 nm (e.g., between about 280 nm and about 290 nm, 285 nm). In some embodiments, the emitted peak wavelength may be between about 300 nm and about 320 nm (e.g., between about 305 nm and about 315 nm, 310 nm). In some embodiments, the emitted peak wavelength may be between about 315 nm and about 335 nm (e.g., between about 320 nm and about 330 nm, 325 nm). In some embodiments, the emitted peak wavelength may be between about 330 nm and about 350 nm (e.g., between about 335 nm and about 345 nm, 340 nm). In some embodiments, the emitted peak wavelength may be between about 355 nm and about 375 nm (e.g., between about 360 nm and about 370 nm, 365 nm). In some embodiments, the emitted peak wavelength may be between about 375 nm and about 395 nm (e.g., between about 380 nm and about 390 nm, 385 nm). In some embodiments, the emitted peak wavelengths may be in the (1) ultraviolet A spectrum (e.g., 315-400 nm); and (2) the ultraviolet B spectrum (e.g., 280-315 nm) or the ultraviolet C spectrum (e.g., 100-280 nm, 200-280 nm, 240-280 nm). In some embodiments, the emitted peak wavelength is in the ultraviolet A spectrum, between about 315 nm and about 350 nm (e.g., between about 320 nm and about 345 nm, between about 315 nm and about 335 nm, between about 330 nm and about 350 nm).

In some embodiments, all light source channels 106 of array of light sources 104 may emit light of about the same (e.g., within variance ±1 nm, ±2 nm, ±3 nm, ±4 nm, ±5 nm) peak wavelength. Light source channels may include a plurality of light sources with different peak wavelengths (e.g., measured peak wavelengths) within a range of variability. In some embodiments, the average peak wavelength across a plurality of light sources for a single light source channel may be the same as a particular peak wavelength for a particular light source in the single light source channel. In other embodiments, the average peak wavelength across a plurality of light sources of a single light source channel may be different (e.g., about 1 nm, 2 nm, 3 nm, 4 nm, 5 nm or more, greater than or less than) than all particular peak wavelengths of each light source in the single light source channel. In some embodiments, some light source channels may emit light of a first peak wavelength and other light source channels may emit light of a second peak wavelength. The first peak wavelength may differ from the second peak wavelength by at least (e.g., greater than) 5 nm, 10 nm, 15 nm, or 20 nm, or more. For example, in a non-limiting embodiment, a first light source channel may emit light with a peak wavelength in the ultraviolet A spectrum, such as described above (e.g., between about 330 nm and about 350 nm) and a second light source channel may emit light with a peak wavelength in the ultraviolet C spectrum, such as described above (e.g., between about 250 nm and about 260 nm, between about 260 nm and about 270 nm) or the ultraviolet B spectrum, such as described above (e.g., between about 305 nm and about 315 nm). In another non-limiting embodiment, a first light source channel may emit light with a peak wavelength in the ultraviolet A spectrum, such as described above (e.g., between about 330 nm and about 350 nm) and a second light source channel may emit light with a peak wavelength also in the ultraviolet A spectrum, such as described above (e.g., between about 315 nm and about 335 nm, between about 355 nm and about 375 nm). In some embodiments, a first peak wavelength is the average peak wavelength of the one or more light sources of a first light source channel. In some embodiments, the array of light sources 104 may comprise first, second, and third light source channels that each respectively emits light of a first, second, and third peak wavelength. In some embodiments, a first peak wavelength may differ from a second peak wavelength by at least (e.g., greater than) 5 nm, 10 nm, 15 nm, or 20 nm or more, and/or the second peak wavelength may differ from a third peak wavelength by at least (e.g., greater than) 5 nm, 10 nm, 15 nm, or 20 nm or more. Alternatively, each of a first, second, and third peak wavelengths may differ from each another by at least (e.g., greater than) 5 nm, 10 nm, 15 nm, or 20 nm, or more. In some embodiments, an array of light sources may comprise first, second, third, and fourth light source channels that each respectively emits light of a first, second, third, and fourth peak wavelength. In some embodiments, at least two, at least three, or at least four of the first, second, third, and fourth peak wavelengths may differ from each other by at least (e.g., greater than) 5 nm, 10 nm, 15 nm, or 20 nm or more. Alternatively, each of the first second, third, and fourth peak wavelengths may differ from each other by at least (e.g., greater than) 5 nm, 10 nm, 15 nm, or 20 nm, or more. Alternatively, the first peak wavelength may be the about same as (e.g., equal to, within variance ±1 nm, ±2 nm, ±3 nm, ±4 nm, ±5 nm) the third peak wavelength, the second peak wavelength may be the about same as (e.g., equal to) the fourth peak wavelength, and the first peak wavelength may differ from the second peak wavelength by at least (e.g., greater than) 5 nm, 10 nm, 15 nm, or 20 nm.

In some embodiments, each light source channel 106 may emit light with a narrow spectral bandwidth. For example, the full-width half-maximum (FWHM) spectral bandwidth of light (e.g., spectral bandwidth at the maximum peak intensity) emitted by each light source channel 106 may be less than 20 nm, less than 18 nm, less than 16 nm, less than 14 nm, less than 12 nm, less than 10 nm, less than 9 nm, less than 8 nm, less than 7 nm, less than 6 nm, or less than 5 nm. In some embodiments, the full-width half-maximum (FWHM) spectral bandwidth of light emitted by each light source channel is within 10 nm less than and/or within 10 nm greater than the peak wavelength (e.g., no more than 10 nm greater than, no more than 10 nm less than the peak wavelength). In some embodiments, the full-width half-maximum (FWHM) spectral bandwidth of light emitted by each light source channel may be greater than 1 nm, greater than 2 nm, greater than 3 nm, or greater than 4 nm, or more. In other examples, 50% of the maximum peak intensity of light emitted by each light source channel is within 10 nm, within 9 nm, within 8 nm, within 7 nm, within 6 nm, within 5 nm, within 4 nm, or within 3 nm of the peak wavelength (e.g., no more than 10 nm greater than, no more than 10 nm less than the peak wavelength; within 10 nm less than, within 10 nm more than the peak wavelength). In other examples, the light intensity at 50% of the maximum peak intensity of light emitted by each light source channel is within a spectral width less than 20 nm, less than 18 nm, less than 16 nm, less than 14 nm, less than 12 nm, less than 10 nm, less than 9 nm, less than 8 nm, less than 7 nm, less than 6 nm, or less than 5 nm (e.g., no more than 10 nm greater than, no more than 10 nm less than the peak wavelength; within 10 nm less than, within 10 nm greater than the peak wavelength). Commercially available LEDs and laser diodes are non-limiting examples of light sources that may provide such narrow spectral bandwidth illumination at the peak wavelengths discussed above.

Enabling narrow spectral bandwidth illumination of biological fluids at various selected peak wavelengths may advantageously maximize the efficiency of the photochemical reaction and/or pathogen inactivation while minimizing unnecessary exposure of biological fluids to light of wavelengths that may affect (e.g., reduce, impair, damage) biological function and/or desirable characteristics (e.g., quality) of the biological fluid. In addition, maximizing the efficiency of the photochemical process may in turn reduce the amount of pathogen inactivation compound required and/or reduce or eliminate the need to remove (e.g., adsorb) unreacted pathogen inactivation compound and/or photoproducts from biological fluids after the pathogen inactivation treatment.

Additionally, narrow spectral band illumination of biological fluids at one or more peak wavelengths may have unexpected advantages and results. For example, when a biological fluid in admixture with the psoralen pathogen inactivation compound amotosalen is illuminated with a narrow spectral band of ultraviolet-A light, such as for example from an LED (e.g., peak wavelength about 315-350 nm, peak wavelength of about 315-335 nm, peak wavelength of about 330-350 nm, peak wavelength of about 325 nm, peak wavelength of about 340 nm, peak wavelength of about 365 nm), increased levels of photoconversion may be observed compared to existing biological fluid treatment systems (INTERCEPT® Blood System, Cerus Corporation) that illuminate the same fluid mixture with broader spectral bandwidth ultraviolet-A (UVA) fluorescent bulbs (e.g., generally in range of 320-400 nm, peak wavelength about 352 nm). In addition, improved levels of pathogen inactivation (e.g., increased log reduction, broader spectrum of pathogens) and/or improved photoproduct profiles may be achieved when a narrow spectral bandwidth light of selected peak UVA wavelength(s) is applied to the biological fluid in admixture with the pathogen inactivation as compared using to existing broader spectrum UVA biological fluid treatment systems. Further, such improvements may be achieved, while retaining desired function and/or characteristics of the biological fluid after treatment with a pathogen inactivation compound and narrow spectral bandwidth light compared to the biological fluid treated using existing broader spectrum illumination sources.

In view of the advantages and unexpected results of treating (e.g., photochemically treating) a biological fluid with narrow spectral bandwidth light sources as provided herein, it may be desirable to control various parameters of the light sources capable of emitting light at such narrow bandwidths. Accordingly, the peak wavelength of emission, the spectral bandwidth of emission, the tilt angle, the duration of emission, and the intensity of emission of each light source channel 106 may be adjusted or set.

Adjustment of these various light source channel parameters may be performed by a control circuitry 126 operatively coupled (e.g., communicatively coupled) to treatment chamber 102, light source array 104, and/or to computer system 128. As used herein, "operatively coupled" refers to any wired or wireless connection between two or more components that enables the two or more components to exchange information, control instructions, and/or control signals. As will be discussed in more detail below, control circuitry 126 may receive control instructions and/or control signals from computer system 128 and send control instructions and/or control signals to various components of treatment chamber 102 to adjust or set various parameters associated with various components of chamber 102. Adjustment of various parameters of chamber 102 may be desirable to ensure that the chamber's treatment parameters are in accordance with the treatment profiles of the one or more biological fluids 108 and 110. It should be recognized that, in some examples, control circuitry 126 and/or the function of control circuitry 126 may be included within computer system 128. In some examples, control circuitry 126 may include computer system 128 and/or the function of computer system 128. In some examples, control circuitry 126 may be structurally attached to treatment chamber 102 (e.g., attached to external side, top, and/or bottom surface of treatment chamber 102). In some examples, control circuitry 126 may be integrated with treatment chamber 102 (e.g., located inside treatment chamber 126 or forming a part of the structure of treatment chamber 102).

Figure 1B:
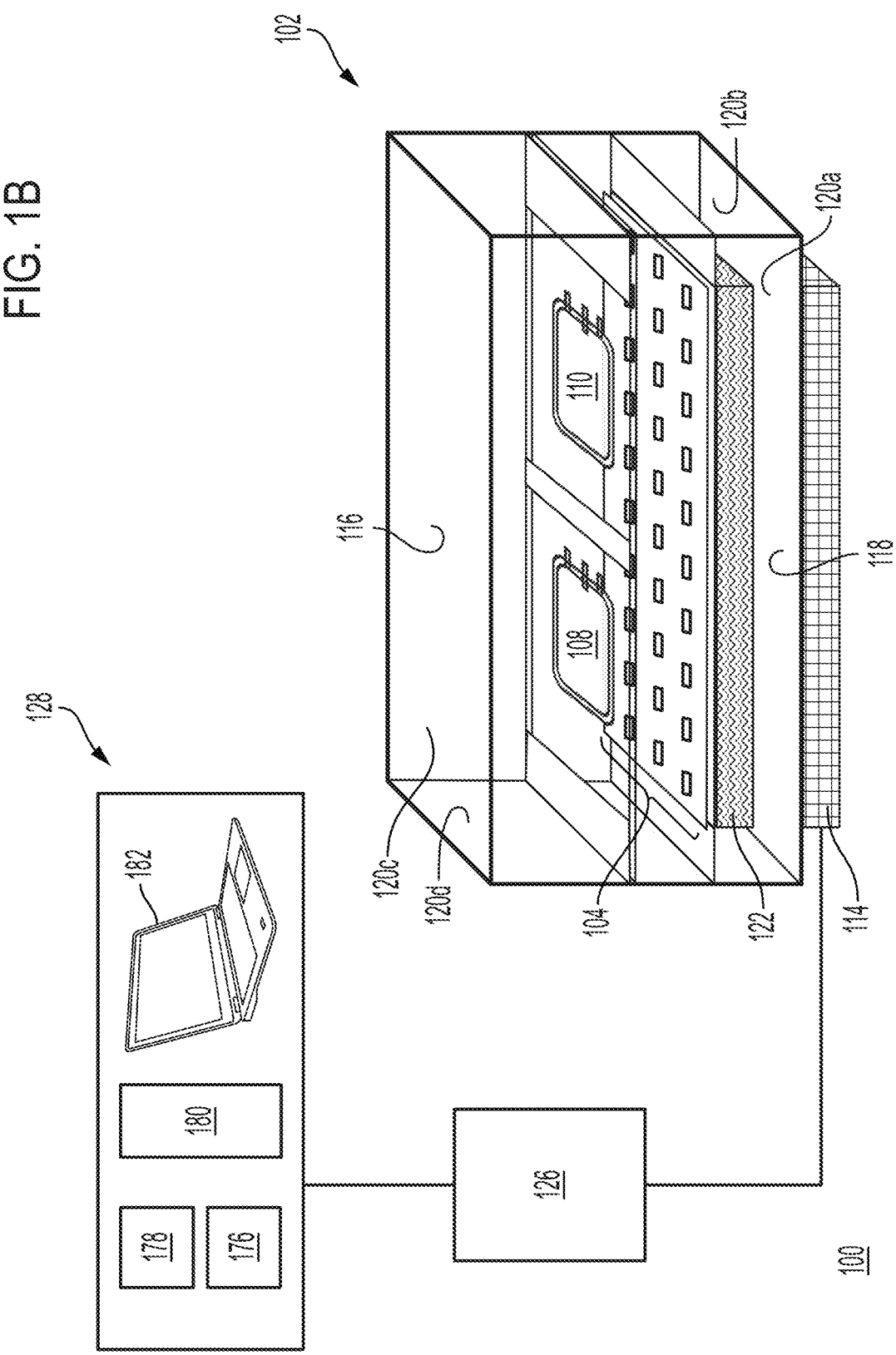

Turning now to additional or optional components of system 100, FIG. 1B shows that array of light sources 104 may be thermally coupled to a heat exchanger 122 (e.g., heat sink, fin heat sink, heat exchanger that may be operatively coupled to and controlled by control circuitry 126). Heat exchanger 122 may draw thermal energy away from array 104 facing one or more biological fluids 108 and 110, thus minimizing the exposure of biological fluids 108 and 110 to thermal energy (e.g., thermal energy that may damage biological function). Further control of the temperature of chamber 102 and/or the temperature of the one or more biological fluids 108 and 110 may be provided by a heating/cooling unit 114 that may be operatively coupled to and controlled by control circuitry 126 and configured to adjust or set the temperature of chamber 102. Heating/cooling 114 unit may be any suitable technology known in the art, such as for example, a fan, heat pump, Peltier cooler and/or heat pipe. Heating/cooling unit 114 may be external to, inside, and/or integrated with chamber 102.

Treatment chamber 102 may further include a plurality of interior surfaces configured to absorb light (e.g., each configured to absorb light). For example, treatment chamber 102 may comprise a top wall 116, a bottom wall 118, and four side walls 120a-d that are made of or coated by a material (e.g., black plastic, black silicate, black paint) that substantially absorbs light of certain wavelengths. As used herein, "substantially absorb" means that more than 50%, 60%, 70%, 80%, or 90% or more of light incident on a surface is not reflected (absorbed) by the surface. For example, each wall 116, 118, and 120a-d may substantially absorb ultraviolet light, ultraviolet-A light, ultraviolet-B light, ultraviolet-C light, visible light, or light with a wavelength of less than 500 nm, 450 nm, 400 nm, 375 nm, 350 nm, 325 nm, 300 nm, 280 nm, or 260 nm.

In some examples, the wavelengths of light substantially absorbed by the plurality of interior surfaces of treatment chamber 102 may depend on one or more peak wavelengths of light emitted by one or more light sources 106 of array of light sources 104. For example, the walls 116, 118, and 120a-d may absorb light with a wavelength equal to a peak wavelength of light emitted by one or more light sources 106 of array of light sources 104. The walls may absorb light with a wavelength within 100 nm, 75 nm, 50 nm, 40 nm, 30 nm, 20 nm, or 10 nm of a peak wavelength of light emitted by one or more light sources 106.

Alternatively or in addition, in some embodiments, treatment chamber 102 may further include one or more interior surfaces configured to reflect light (e.g., each configured to reflect light). For example, treatment chamber 102 may comprise a top wall 116, a bottom wall 118, and four side walls 120a-d, any or all of which are made of or coated by a material that substantially reflects light of certain wavelengths. As used herein, "substantially reflects" means that more than 50%, 60%, 70%, 80%, or 90% or more of light incident on a surface is reflected by the surface. For example, each wall 116, 118, and 120a-d may substantially reflect ultraviolet light, ultraviolet-A light, ultraviolet-B light, ultraviolet-C light, visible light, or light with a wavelength of less than 500 nm, 450 nm, 400 nm, 375 nm, 350 nm, 325 nm, 300 nm, 280 nm, or 260 nm.

Biological Fluid Containers

Figure 1C:
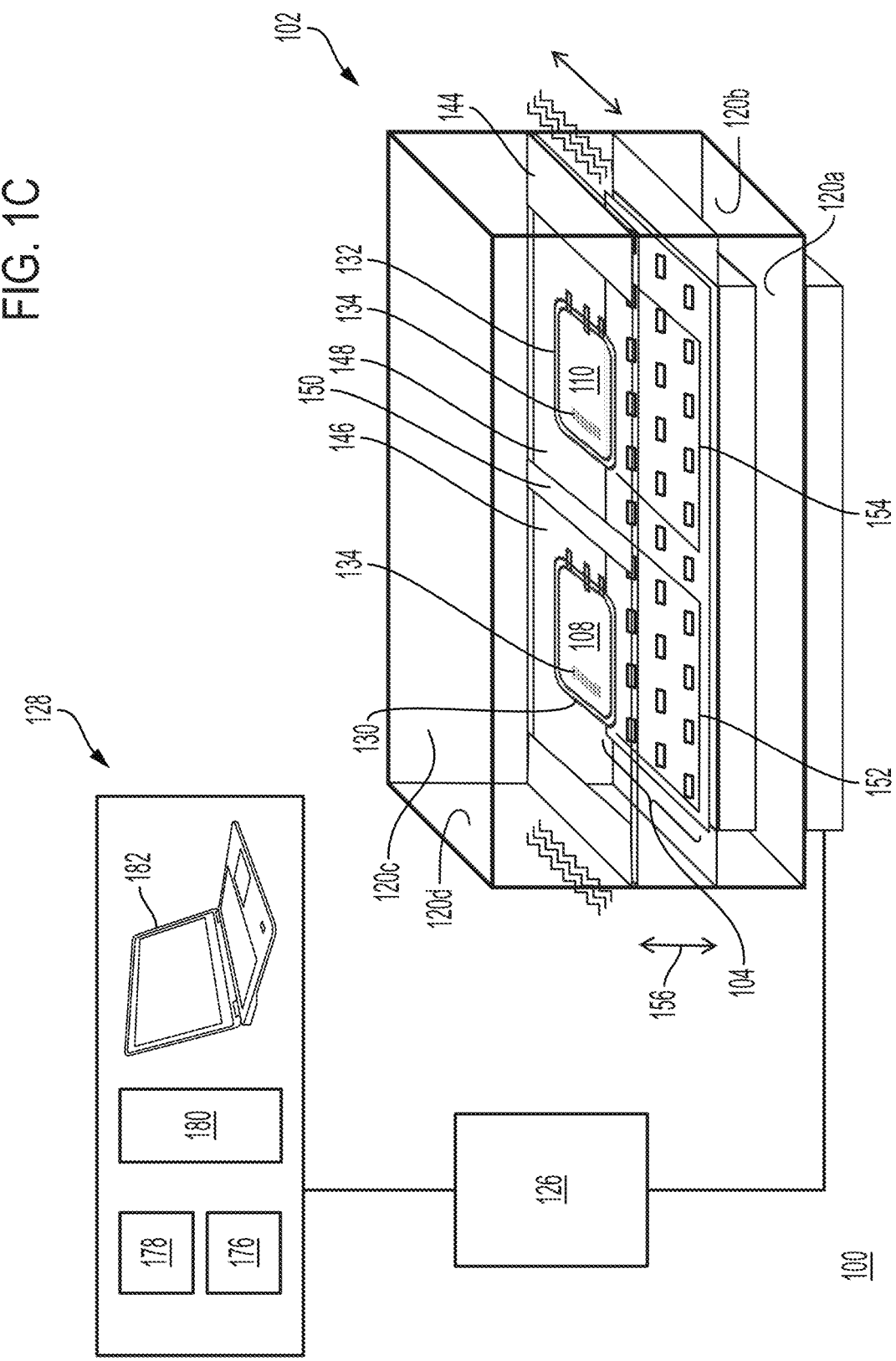

As shown in FIG. 1C, biological fluids 108 and 110 may be respectively contained in biological fluid containers 130 and 132. Containers 130 and 132 may include an identifier (e.g., barcodes 134, RFID, label) for identification of the contained biological fluid. In one example, the biological fluid containers 130 and 132 may be made from any translucent or transparent or otherwise substantially light-transmissive (e.g., light transmissive for ultraviolet peak wavelength provided herein) material that may also be sterilizable and/or flexible. When biological fluids comprise blood or a blood product, the biological fluid containers may comprise a hemocompatible material, such as for example, a polymer material used in the art for blood product bags (e.g., plasma bag, platelet bag).

In some embodiments, the biological fluid containers may be individual containers (e.g., container 130) not connected to other containers. In some embodiments, the biological fluid containers may be connected to one or more additional containers, such as for example a storage container and/or a compound adsorption device. Such biological fluid containers may, in some embodiments, be inserted into the treatment chamber for exposure of the biological fluid to a desired amount of light and then removed subsequent to such light exposure. In other embodiments, a biological fluid may be flowed into and out of treatment chamber 102 using multiple containers. In particular, the treatment chamber may include a treatment container 132 positioned in the treatment chamber for receiving and treating the biological fluid. The treatment container 132 may be adapted for joining to a source container positioned outside the treatment chamber, and an exit container positioned outside chamber 102 for receiving the treated biological fluid from treatment container 132. The joining between the source container, treatment container 132, and the exit container may be through tubing connecting the source container, treatment container 132, and the exit container. Pumps may be operably attached or otherwise connected to one or more of the source container, tubing, treatment container 132, and the exit container to transfer the biological fluid 110 between the containers. The pumps may be operatively coupled to control circuitry 126 and control circuitry 126 may control the volumetric flow rate of the biological fluid between the containers by controlling the pumps.

Platform for Carrying the Biological Fluid

As indicated in FIG. 1C, treatment chamber 102 may further comprise a platform 144 configured to hold one or more biological fluids 108 and 110 (e.g., containers of biological fluids). Platform 144 may be a tray, a well, or any other support suitable for carrying biological fluids or containers of biological fluids. Platform 144 may be positioned in a "drawer configuration" so that it is slidably movable manually into and out of chamber 102. Platform 144 may be slidably movable automatically by any suitable actuator, such as an electric motor or servo. Platform 144 carrying biological fluids 108 and 110 may be positioned above the light source array 104 with light source array 104 facing platform 144. However, in other embodiments, platform 104 carrying one or more biological fluids may be positioned below light source array 104 with light source array 104 facing the platform 144. In other embodiments, light sources may be disposed on an array parallel to one of sidewalls 120a-d of treatment chamber 102 to provide illumination of the one or more biological fluids 108 and 110 from various sides.

In some embodiments, platform 144 may comprise a first compartment 146 and a second compartment 148 separated from each other (e.g., by dividing wall 150). First compartment 146 may be configured to hold first biological fluid 108 and second compartment may be configured to hold second biological fluid 110. First biological fluid 108 may be a same or a different type of biological fluid as second biological fluid 110. In other embodiments, platform 144 may comprise more than two compartments each separated from each other (e.g., by dividing walls). Each compartment may be configured to separately hold a biological fluid.

In embodiments where platform 144 is configured to carry two or more biological fluids, treatment of two or more different biological fluids requiring different treatment profiles may be performed in a single treatment chamber. For example, as shown in FIG. 1C, a first set of light sources 152 facing first biological fluid 108 may be controlled to emit light in accordance with a treatment profile of first biological fluid 108, and a second set of light sources 154 facing second biological fluid 110 may be controlled to emit light in accordance with a treatment profile of second biological fluid 110.

In some embodiments, platform 144 may be translucent or transparent to light of selected wavelengths. In particular, platform 144 may be made of materials such as for example, a plastic or glass to achieve the selected wavelength translucencies or transparencies. These selected wavelengths may be determined by a peak wavelength of light emitted from one or more light source channels 106 of array of light sources 104. For example, the platform may be translucent or transparent to light having a wavelength within 200 nm, 150 nm, 100 nm, 75 nm, 40 nm, 30 nm, or 20 nm of a peak wavelength of light emitted from a light source channel of array 104. In other embodiments, platform 144 may be translucent or transparent to a specific type of light. For example, platform 144 may be transparent to light in the ultraviolet spectrum, ultraviolet-A spectrum, ultraviolet-B spectrum, ultraviolet-C spectrum, and/or visible light spectrum.

In examples where platform 144 is divided into a plurality of compartments, each compartment may be translucent or transparent to light of the selected wavelengths described above. In other words, each compartment of the plurality of compartments of platform 144 may be made of a different material to provide the desired translucencies or transparencies. For example, as shown in FIG. 1C, in an embodiment where platform 144 comprises a first compartment 146 and a second compartment 148, first compartment 146 may be translucent or transparent to light of a first selected range of wavelengths, while second compartment 148 may be translucent or transparent to light of a second selected range of wavelengths.

Platform 144 and array of light sources 104 may translate relative to each other to increase or decrease a distance 156 between array of light sources 104 and platform 144. In one example, the distance 156 may be adjusted or set in the range of 0-19 centimeters. Control circuitry 126, which may be operatively coupled to platform 144 and/or array of light sources 104, may control this translation. For example, control circuitry 126 may control the relative positioning of platform 144 and array of light sources 104 by controlling actuator(s) (e.g., electric motor, servo, etc.) that control the displacement and orientation of platform 144 and/or array of light sources 104. Further, control circuitry 126 may separately control movement of array of light sources 104 and movement of platform 144. Changing the distance 156 between platform 144 and array of light sources 104 may be desirable to change the dose of light energy (e.g., change the intensity of light) incident on the one or more biological fluids 108 and 110 and/or the degree of heat transfer between the array of light sources 104 and the one or more biological fluids 108 and 110.

In some embodiments, it may be desirable to agitate the one or more biological fluids 108 and 110 before, during and/or after illumination. In particular, agitation of a biological fluid may be desirable so that the fluid is sufficiently and uniformly exposed to emitted light and/or any pathogen inactivation compound. Accordingly, platform 144 may be configured to agitate one or more biological fluids 108 and 110 carried by platform 144. In particular, platform 144 may vibrate (e.g., due to a vibration motor attached to or integrated with platform 144), move with an orbital motion (e.g., due to an electric motor or servo that moves platform 144 through a preset orbital track or displacement path), or move with a reciprocating motion (e.g., from side-to side) at a specified frequency (e.g., due to a reciprocating motor). The frequency, onset, and type of such agitation may be based on instructions and/or control signals from control circuitry 126 received by and any suitable electromechanical drive mechanism attached to or integrated with platform 144.

Barrier

Treatment chamber 102 may further comprise a barrier 158 positioned between array of light sources 104 and one or more biological fluids 108 and 110. For example, barrier 158 may be positioned between array of light sources 104 and platform 144. Barrier 158 may be a protective barrier, such as for example, a barrier that separates one or more biological fluids 108 and 110 from array of light sources 104 to reduce the likelihood of contaminating and or need for cleaning the array of light sources 104. Alternatively or in addition, barrier 158 may be a light filter that transmits or attenuates the transmittance of light of certain wavelengths. Barrier 158 may be made of materials such as for example, a plastic or glass to transmit or attenuate the transmittance of light of all or certain wavelengths. Barrier 158 may, for example, have a thickness in the range of 1-10 mm.

In some examples, barrier 158 may be configured to transmit at least 50%, 60%, 70%, 80%, 90%, 95%, 97% or 99% or more of light of a desired wavelength (e.g., wavelengths of light emitted by light source channels 106, wavelengths of light that photoactivate a particular pathogen inactivation compound). In some examples, barrier 158 may be configured to attenuate transmittance of light having less than a certain wavelength, such as for example, a wavelength of less than 320 nm, 310 nm, 300 nm, 290 nm, 280 nm, 270 nm, 260 nm, 250 nm or 240 nm. In other embodiments, barrier 158 may be configured to attenuate transmittance of light having greater than a certain wavelength (e.g., greater than 350 nm, greater than 370 nm, greater than 400 nm, or more). As used herein, "attenuate" may mean that less than 50%, 40%, 30%, 20%, 10%, 5%, 4%, 3%, 2%, or 1% of light is transmitted through barrier 158.

In some examples, one or more wavelengths of light transmitted or attenuated by light barrier 158 may depend on one or more wavelengths of light emitted by light source channels 106. For example, barrier 158 may be configured to attenuate transmittance of light with wavelengths at least 5 nm, 10 nm, 20 nm, 25 nm, or 30 nm or more greater or less than a peak wavelength of light emitted by a light source channel 106. The barrier may be configured to be translucent or transparent to light with a wavelength within 5 nm, 10 nm, 15 nm, 20 nm, 25 nm, or 30 nm of a peak wavelength of light emitted by a light source channel 106 of the array of light sources 104.

In some examples, barrier 158 may be divided into a plurality of portions, wherein each portion may attenuate transmittance of light with any of the wavelengths described above, and/or to different levels. In other words, each portion of the plurality of portions of barrier 158 may be made of a different or a same material to provide desired transmittance or attenuation of light of certain wavelengths and/or to different levels. For example, in an embodiment where barrier 158 comprises a first portion 160 and a second portion 162, first portion 160 positioned below first compartment 146 of platform 144 may attenuate transmittance of light of a selected range of wavelengths, while second portion 162 of barrier 158 positioned below second compartment 148 of platform 144 may attenuate transmittance of light of another selected range of wavelengths.

In embodiments where platform 144 and/or barrier 158 are selectively translucent or transparent and selectively attenuate light of selected wavelengths and/or to different levels, one or more biological fluids 108 and 110 may only be substantially illuminated by wavelengths of light in accordance with their respective treatment profiles. Accordingly, wavelength selective illumination may result in a more efficient photochemical reaction and thus more efficient pathogen inactivation. In addition, the exposure of one or more biological fluids 108 and 110 to light of unwanted wavelengths that may damage biological function may be minimized.

Light Source Array Configurations

Turning to FIGS. 2A-2D, exemplary light source array configurations of array of light sources 104 are now described.

Figure 2A:
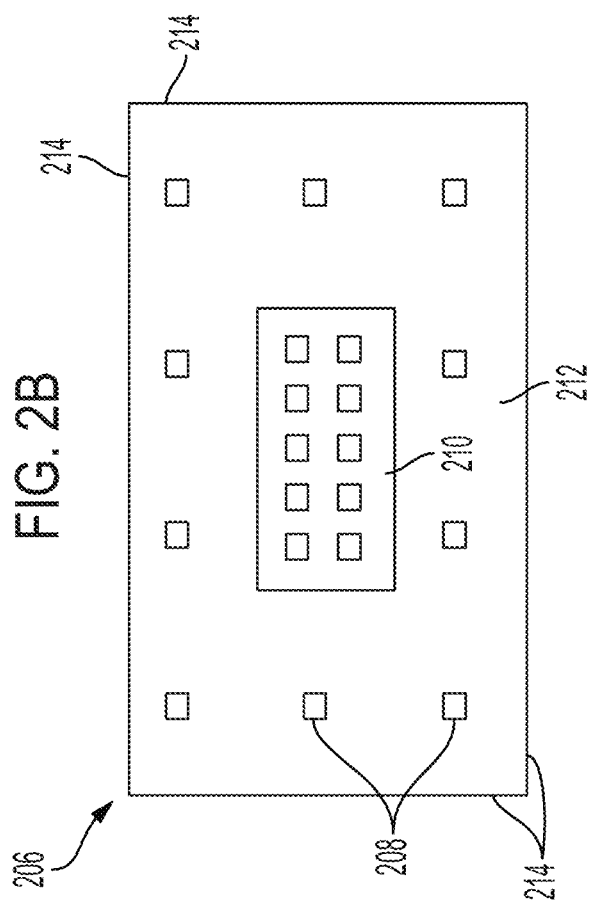
FIGS. 2A-2D illustrate exemplary light source array configurations.

FIG. 2A shows an exemplary light source array configuration where light sources 202 are positioned in a distribution on array of light sources 200. In particular, the light sources 202 may be positioned in light source clusters 204. Each light source 202 belonging to the same light source channel may emit light at the same wavelength (e.g., peak wavelength) in the visible light spectrum or in the ultraviolet light spectrum, such as for example, the ultraviolet-A spectrum, the ultraviolet B spectrum, or the ultraviolet-C spectrum. In other words, each light source channel may be a set of one or more light sources 202 having the same wavelength. As shown in FIG. 2A, each light source cluster may include two or more (e.g., three or more, four or more, five or more, six or more) light sources 202. In some examples, the two or more light sources 202 may emit peak wavelengths of light that differ from each other by at least (e.g., greater than) 5 nm, 10 nm, 15 nm, or 20 nm or more. In other examples, the two or more light sources 202 may include one or more (e.g., two or more, three or more) pairs of light sources. For example, as shown in FIG. 2A, each light source cluster 204 may include four light sources 202. A first pair of light sources of a common light source channel may emit light with a first peak wavelength and a second pair of light sources of another common light source channel may emit light with a second peak wavelength that differs from the first peak wavelength by at least (e.g., greater than) 5 nm, 10 nm, 15 nm, or 20 nm or more. Alternatively, a first pair of light sources (e.g., first and second light sources respectively of first and second light source channels) may emit light with a first peak wavelength and another light source (e.g., third light source of a third light source channel) may emit light with a second peak wavelength and yet another light source (e.g., fourth light source of a fourth light source channel) may emit light with a third peak wavelength, wherein the first peak wavelength differs from the second peak wavelength by at least (e.g., greater than) 5 nm, 10 nm, 15 nm, or 20 nm or more, and the second peak wavelength differs from the third peak wavelength by at least (e.g., greater than) 5 nm, 10 nm, 15 nm, or 20 nm or more. Alternatively, a first light source (e.g., first light source of a first light source channel) may emit light with a first peak wavelength, another light source (e.g., second light source of a second light source channel) may emit light with a second peak wavelength, yet another light source (e.g., third light source of a third light source channel) may emit light with a third peak wavelength and still yet another light source (e.g., fourth light source of a fourth light source channel) may emit light with a fourth peak wavelength, wherein the first peak wavelength differs from the second peak wavelength by at least (e.g., greater than) 5 nm, 10 nm, 15 nm, or 20 nm or more, and the second peak wavelength differs from the third peak wavelength by at least (e.g., greater than) 5 nm, 10 nm, 15 nm, or 20 nm or more, and the third peak wavelength differs from the fourth peak wavelength by at least (e.g., greater than) 5 nm, 10 nm, 15 nm, or 20 nm or more.

Figure 2B:
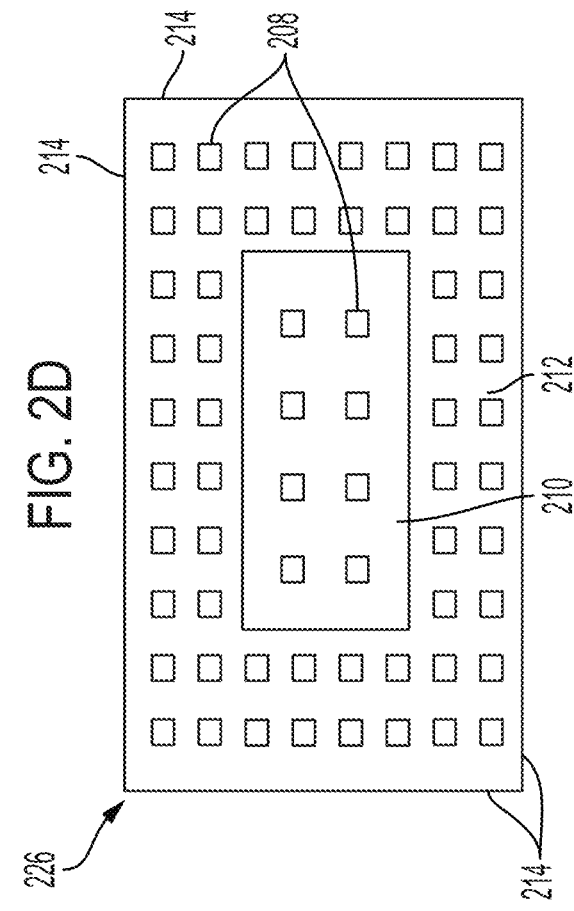

FIG. 2B shows another exemplary light source array configuration where light sources 208 (e.g., of the same light source channel) are positioned in a distribution on array of light sources 206. In particular, array of light sources 206 may comprise an inner region 210 and an outer region 212. The inner region 210 may occupy less than 50% (e.g., less than 40%, less than 30%, less than 20%, less than 10%) of the surface area of array 206 while outer region may occupy the remaining percentage of the surface area (e.g., 50%-90% or more) of array 206. Alternatively, the inner region 210 may occupy less than 90% (e.g., less than 80%, less than 70%, less than 60%) of the surface area of array 206 while outer region may occupy the remaining percentage of the surface area (e.g., 10%-50% or more) of array 206. A density of light sources 208 positioned in inner region 210 (e.g., of the same light source channel) may be greater than the density of light sources 208 positioned in outer region 212 (e.g., of the same light source channel). In other embodiments, as shown in FIG. 2D, a density of light sources 208 positioned in the inner region 210 (e.g., of the same light source channel) may be less than the density of light sources 208 positioned in outer region 212 (e.g., of the same light source channel) in array of light sources 216. In these examples, the density of light sources positioned in inner region 210 and the density of light sources positioned in outer region 212 may differ by at least 1.2-fold, 1.5-fold, 2-fold, 2.5-fold, 3.0-fold, or more (e.g., greater density in inner region versus outer region as in FIG. 2B, greater density in outer region versus inner region as in FIG. 2D).

As shown in FIG. 2B and FIG. 2D, in some embodiments, light sources 208 are not positioned on (e.g., near) one or more outer edges 214 of array 206. In other embodiments, the light sources 208 may be positioned on (e.g., near) one or more outer edges 214.

Figure 2C:
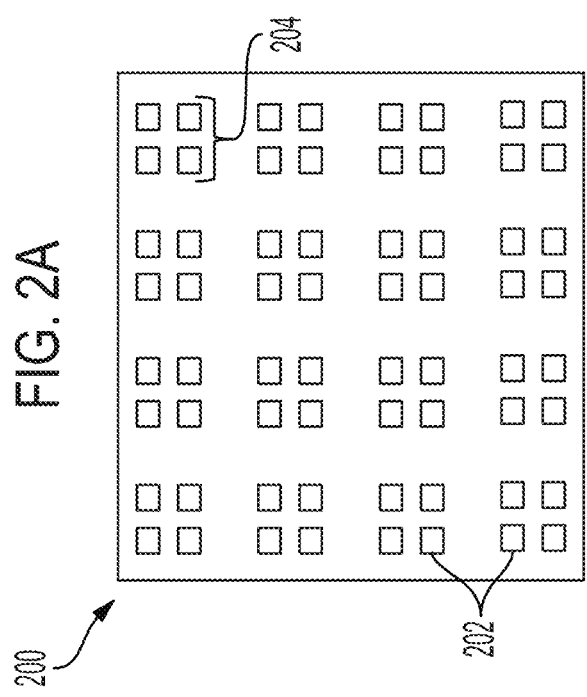
Figure 2D:
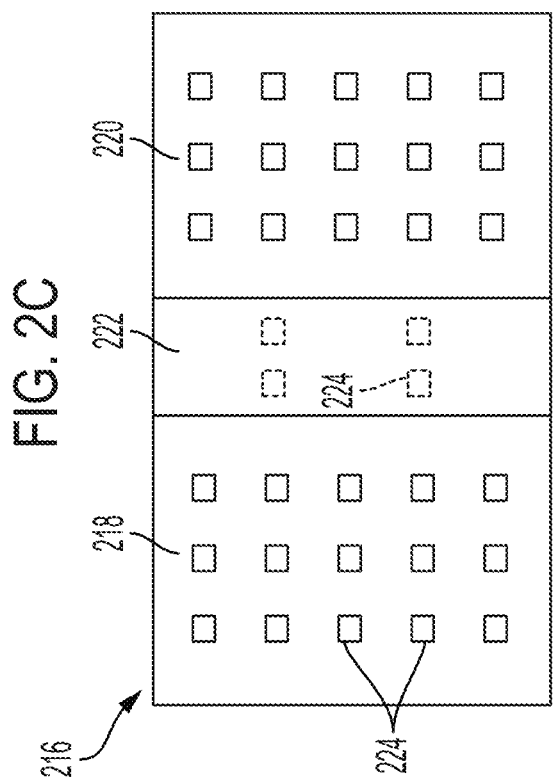

FIG. 2C shows another exemplary light source array configuration in which the array of light sources 216 comprises a first region 218 and a second region 220, separated by a third region 222. The density of light sources 224 positioned in the first region 218 and in the second region 220 may each be greater than the density of light sources positioned in regions outside the first region 218 and the second region 220 (e.g., the third region 222), such as for example, a third region comprising no light sources. In some embodiments, the third region does comprise one or more light sources. Such a light source array configuration may be desirable in embodiments discussed above where treatment chamber 102 includes first biological fluid 108 and second biological fluid 110. In particular, the light sources positioned in the first region 218 may face first biological fluid 108, and the light sources positioned in the second region 220 may face second biological fluid 110. The light sources of the first region 218 may illuminate first biological fluid 108 in accordance with a treatment profile for first biological fluid 108, and the light sources of the second region 220 may illuminate second biological fluid 110 in accordance with a treatment profile for second biological fluid 110. No light sources or a lower density of light sources may be positioned in regions (e.g., third region 222) that do not face either the first or the second biological fluid. For example, no light sources may be needed in third region 222 if the third region faces dividing wall 150 of platform 144. Alternatively, third region 222 may include light sources tilted toward the first or second biological fluid or both.

On a given light source array, light sources may be positioned in a uniform distribution. For example, FIG. 2A may be understood as showing light source clusters 204 (e.g., sixteen light source clusters 204) in a uniform distribution on light source array 200. For light source array 200, there may be four light source channels, each light source channel including one light source 202 at the same respective location in each cluster 204. Thus each cluster 204 may comprise four light sources, one each from four different light source channels. Alternatively, on a given light source array, the positioning of light sources and arrangement of light source channels may provide a non-uniform distribution. Light sources themselves may be positioned in a non-uniform distribution. Light sources for a given light source channel may be positioned in a non-uniform distribution. The one or more lights sources of an "array of light sources" may be in any positional arrangement (e.g., linear, curvilinear, row(s) and column(s), regular pattern, irregular spacing, etc.). Uniform distribution may be provided by a regular pattern and spacing uniformly applied for light sources of an entire array, as exemplified in FIG. 2A. Non-uniform distribution may be provided, for example, by an irregular pattern and spacing applied for light sources of an entire array, as exemplified by the inner and outer regions having different densities of light sources in FIG. 2B and FIG. 2D.

The various configurations of light sources discussed above may be desirable to illuminate various biological fluids requiring various respective treatment profiles. In addition, the various configurations of light sources may be desirable to achieve substantially uniform illumination of a surface of a biological fluid or a surface of a biological fluid container. For examples, various configurations of light source arrangements for an array are exemplified in FIGS. 2A-2D, and various configurations of light source distances from biological fluid are exemplified in FIG. 4 and FIG. 6B. A surface of the biological fluid may be defined by, for example, a surface of a biological fluid container holding the fluid or a plane intersecting any portion of the biological fluid. In one example, the light sources of the array of light sources 104 may be configured (e.g., positioned in the array) such that the light sources illuminate a biological fluid with less than 25% (e.g., less than 20%, less than 15%, less than 10%) variance in irradiance across a surface of biological fluid 108 facing array of light sources 104. In other words, the light intensity at any one portion of the surface of biological fluid 108 facing array of light sources 104 may differ from the light intensity at any other portion of the surface of biological fluid 108 facing array of light sources 104 by less than 25% (e.g., less than 20%, less than 15%, less than 10%).

In another example, the light sources of the array of light sources 104 may be configured such that the light sources illuminate any 5 square-centimeter area of a surface of biological fluid 108 with an irradiance less than 25% (e.g., less than 20%, less than 15%, less than 10%) from the averaged integrated irradiance across the entire surface of biological fluid 108. In other words, the light intensity received within any 5-square centimeter area of a surface of biological fluid 108 facing array 104 may differ from the total light intensity (averaged over surface area) received by the surface of biological fluid 108 facing array 104 by less than 25% (e.g., less than 20%, less than 15%, less than 10%).

Turning now to FIGS. 3-6B, additional embodiments of exemplary light source array configurations in treatment systems for treating one or more biological fluids are described.

Figure 3:
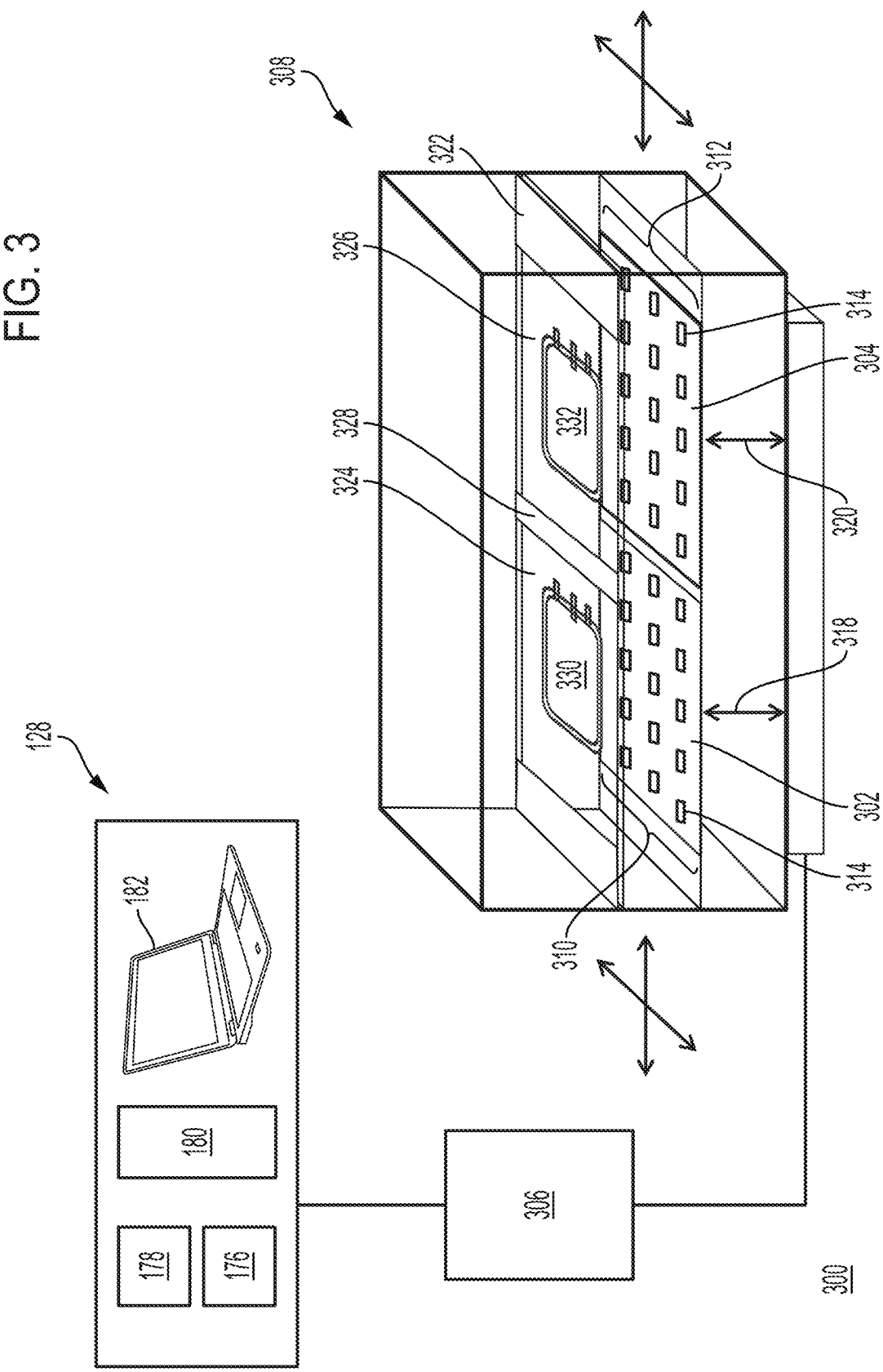
FIG. 3 is a perspective view of an exemplary system for treating biological fluids comprising a light source array with multiple panels of light sources.

FIG. 3 shows a perspective view of an exemplary system for treating biological fluids 300 comprising a light source array configuration comprising multiple panels of light sources 302 and 304 in treatment chamber 308. Although only two light source panels are depicted in FIG. 3, in other examples, light source array may include more than two (e.g., three, four, five or more) panels of light sources. Treatment chamber 308 may be operatively coupled to control circuitry 306 capable of adjusting or setting various parameters of treatment chamber 308, such as for example, adjusting or setting parameters of a light source (e.g., the peak wavelength of emission, the spectral bandwidth of emission, the tilt angle, the duration of emission, the intensity of emission) within the treatment chamber.

Each light source panel 302 and 304 may be independently removable from treatment chamber 308 (e.g., from an array of light sources) and operatively coupled to control circuitry 306. Each light source panel 302 and 304 may comprise an array of light sources, e.g., 310 and 312. Control circuitry 306 may adjust or set various parameters of each light source 314 of each light source panel 302 and 304. For example, the control circuitry may adjust or set the peak wavelength, the spectral bandwidth, the intensity, the duration, and the tilt angle of light emission of each light source 314 of each light source panel 302 and 304. Further, each of the corresponding light source arrays 310 and 312 may be independently configured with the various distributions of light sources discussed above for FIGS. 2A-2D.

Each light source 314 of each array of light sources 310 and 312 disposed respectively on panels 302 and 304 may be connected in a series circuit within each panel. Each panel 302 and 304 may be connected in a parallel circuit with the other panel.

In some embodiments, control circuitry 306 may adjust or set the positions of the light source panels 302 and 304 within treatment chamber 308. In particular, control circuitry 306 may send control instructions and/or control signals to, e.g., an electric motor(s), servo(s), or any suitable electromechanical drive mechanism attached to or integrated with each light source panel 302 and 304 and that cause the panels to translate relative to each other to increase or decrease a distance between light source panels 302 and 304. For example, first light source panel 302 may translate parallel to the plane of the first light source panel 302 and the second light source panel 304 may translate parallel to the plane of the second light source panel 304. First light source panel 302 may translate to increase or decrease a first distance 318 between bottom plane 316 of treatment chamber 308 and first light source panel 302. Similarly, second light source panel 304 may also translate to increase or decrease a second distance 320 between bottom plane 316 and second light source panel 304.

In some embodiments, treatment chamber 308 may include a platform 322 (e.g., a platform comprising one or more compartments). A panel of light sources of multiple panels of light sources in a light source array may face each compartment, e.g., in direct alignment without lateral offset. For example, as shown in FIG. 3, platform 322 may comprise a first compartment 324 and a second compartment 326 separated from each other by dividing wall 328. First compartment 324 may be configured to hold a first biological fluid 330 and second compartment may be configured to hold a second biological fluid 332. First panel of light sources 302 may face first compartment 324, and second panel of light sources 304 may face second compartment 326.

Configuring treatment chamber 308 to include multiple independently controllable light source panels may be desirable in examples where multiple types of biological fluids are to be treated in chamber 308. For example, if first biological fluid 330 is a different type than second biological fluid 332, different treatment profiles for the first and the second biological fluids may be desired. To deliver these different treatment profiles, first panel 302 facing first biological fluid 330 and second panel 304 facing second biological fluid 332 may be independently configured and controlled by control circuitry 306. For example, control circuitry 306 may set or adjust the configuration of light sources on first panel 302 and/or the configuration of light sources on light panel 304 to be different from each other. Further, control circuitry 306 may set or adjust the distance between the first panel 302 and the first biological fluid 330 and/or the distance between second panel 304 and second biological fluid 332 to be different from each other. Further still, control circuitry 306 may set or adjust the light characteristics (e.g., the duration, wavelength, intensity, spatial pattern, and temporal pattern of emission of light) emitted by first panel 302 and/or the light characteristics emitted by second panel 304 to differ from each other.

Figure 4:
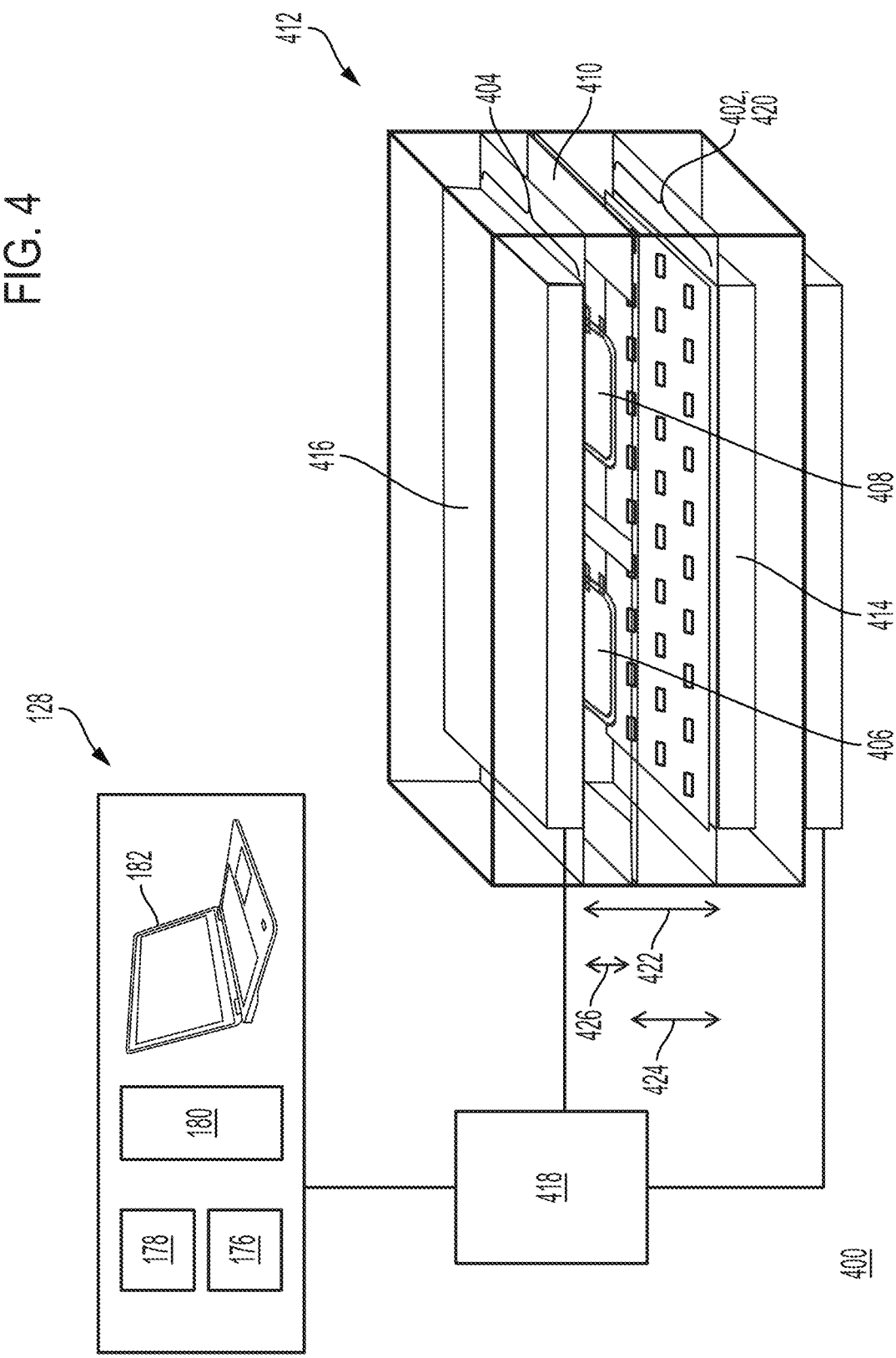
FIG. 4 is a perspective view of an exemplary system for treating biological fluids comprising opposing light source arrays facing a platform for biological fluids.

FIG. 4 shows a perspective view of an exemplary system 400 for treatment of one or more biological fluids 406 and 408 comprising opposing light source arrays 402 and 404 positioned in treatment chamber 412. Opposing light source arrays 402 and 404 may each be respectively thermally coupled to heat exchangers 414 and 416. Treatment chamber 412 may include platform 410 positioned between opposing light source arrays 402 and 404, the platform configured to hold one or more biological fluids 406 and 408. Providing illumination of biological fluids 406 and 408 from opposing sides may be desirable, for example, to more uniformly illuminate the biological fluids.

Treatment chamber 412, opposing light source arrays 402 and 404, heat exchangers 414 and 416, and platform 410 may each be operatively coupled to a control circuitry 418 that may adjust or set their respective parameters.

First opposing light source array 402 may comprise a first array of light source channels 420 and second opposing light source array 404 may comprise a second array of light source channels (not shown). Each light source channel 420 of the first opposing light source array 402 and each light source channel of the second opposing light source array 404 may be configured to emit light of the various peak wavelengths discussed above.

In some embodiments, one or more wavelengths of light emitted by first opposing light source array 402 may be the same as the one or more wavelengths of light emitted by second opposing light source array 404. For example, a first light source channel and a second light source channel of first opposing array 402 may respectively emit light of a first peak wavelength and a second peak wavelength differing from the first wavelength by at least (e.g., greater than) 5 nm, 10 nm, 15 nm, or 20 nm or more. A third light source channel and a fourth light source channel of second opposing array 404 may respectively emit light with a wavelength the same as (e.g., equal to) the first and the second peak wavelengths.

In some embodiments, all light sources of first opposing array 402 may emit light of a single peak wavelength (e.g., first peak wavelength). All light sources of second opposing array 404 may also emit light of a single peak wavelength (e.g., first peak wavelength). The peak wavelength of light emitted by all light sources of first opposing array 402 may be the same as (e.g., equal to) the peak wavelength of light emitted by all light sources of second opposing array 404. Alternatively, the peak wavelength of light emitted by all light sources of first opposing array 402 may differ from the peak wavelength of light emitted by all light sources of the second opposing array 404 by at least (e.g., greater than) 5 nm, 10 nm, 15 nm, or 20 nm, or more.

In some embodiments, first opposing array 402, second opposing array 404, and platform 410 may all be configured to translate relative to each other to increase or decrease distances 422, 424, and 426 between any pair of: first opposing array 402, second opposing array 404, and platform 410. This translation may be effected by any number of actuators (e.g., electric motor, servo, etc.) controlled by control circuitry 418, which may separately control translation of first opposing array 402, second opposing array 404, and platform 410.

FIG. 5 shows a perspective view of exemplary system 500 comprising treatment chamber 502 and multiple light source arrays 504 and 506 facing the same direction. Light source arrays 504 and 506 may each respectively be thermally coupled to heat exchangers 508 and 510. Treatment chamber 502 may optionally include multiple platforms 512 and 514 each configured to carry one or more (e.g., multiple) biological fluids 516. Such configuration of system 500 may provide separate treatment regions within the treatment chamber 502, each with separate access (e.g., separate openings, separate slideable drawers) for treating multiple biological fluids. Such configuration may be desirable for high-throughput treatment of biological fluids and/or treating biological fluids (e.g., different biological fluids) with different conditions or at different times (e.g., not concurrent treatment cycles).

Treatment chamber 502, each of the multiple light source arrays 504 and 506, each of the heat exchangers 508 and 510, and each of the platforms 512 and 514 may be operatively coupled (directly or indirectly) to a control circuitry 518 that may adjust or set their various parameters.

As shown in FIG. 5, first light source array 504 may face a same direction as second light source array 506. First platform 512 may be positioned in first region 520 between first light source array 504 and second light source array 506. First light source array 504 may comprise the only light sources of the treatment chamber 502 that illuminates one or more biological fluids in first region 520. For example, the treatment chamber 502 may be configured (e.g., with an opaque dividing wall) such that light from second light source array 506 may not illuminate region 520. Second platform 514 may be positioned in a second region 522 outside the first region 520 (e.g., above second array of light sources 506). Second light source array 506 may face the second platform 514. Second light source array 506 may be the only light source of the treatment chamber 502 that illuminates one or more biological fluids in second region 522. For example, the treatment chamber 502 may be configured (e.g., with an opaque dividing wall) such that light from first light source array 504 may not illuminate region 522.

Treatment chamber 502 may optionally include a third light source array and a fourth light source array (not shown) facing the same direction as first light source array 504 and second light source array 506. The third light source array may face a third platform (not shown) positioned between the third and the fourth array of light sources (e.g., in a third region). The fourth light source array may face a fourth platform (not shown). One of ordinary skill in the art will appreciate that treatment chamber 502 may be extended to accommodate any number of light source arrays facing in the same direction and any number of platforms. Each additional light source array may provide an additional region (not shown), for example, with each additional light source array providing the only light source of the treatment chamber 502 that illuminates one or more biological fluids in its respective region. Similarly, each separate treatment region within the treatment chamber may have separate access (e.g., separate openings, separate slideable drawers), for independently treating multiple biological fluids.

First light source array 504 may comprise one or more light source channels 524 and second light source array 506 may comprise one or more light source channels 526. Each light source channel 524 of first light source array 504 and each light source channel 526 of second light source array 506 may be configured to emit light of the various peak wavelengths discussed above.

In some embodiments, the peak wavelengths of light emitted by light source arrays 504 and 506 may be the same. This may be desirable in examples where multiple biological fluids 516 (e.g., biological fluids of the same type) requiring the same treatment profile or treatment with light of the same peak wavelength are to be treated in chamber 502. For example, a first light source channel and a second light source channel of first light source array 504 may respectively emit light of a first peak wavelength and a second peak wavelength differing from the first wavelength by at least (e.g., greater than) 5 nm, 10 nm, 15 nm or 20 nm, or more. A third light source channel and a fourth light source channel of second light source array 506 may respectively emit light with a wavelength the same as (e.g., equal to) the first and the second peak wavelengths.

In some embodiments, all light source channels 524 of first light source array 504 may emit light of a single peak wavelength (e.g., first peak wavelength). All light source channels 526 of second light source array 506 may also emit light of a single peak wavelength (e.g., first peak wavelength). The peak wavelength of light emitted by all light source channels 524 of first light source array 504 may be the same as (e.g., equal to) the peak wavelength of light emitted by all light source channels 526 of second light source array 506. Alternatively, the peak wavelength of light emitted by all light source channels 524 of first light source array 504 may differ from the peak wavelength of light emitted by all light source channels 526 of second light source array 506 by at least (e.g., greater than) 5 nm, 10 nm, 15 nm, and 20 nm or more.

In some embodiments, each of light source arrays 504 and 506, and each of platforms 512 and 514 may translate relative to each other to increase or decrease a distance between any pair of arrays of light sources 504 and 506 and platforms 512 and 514. Such translation may be effected by any number of actuators (e.g., electric motor, servo, etc.) controlled by control circuitry 518, which may separately control translation of each of arrays of light sources 504 and 506 and each of platforms 512 and 514. Similarly, additional light source arrays and platforms (e.g., third and fourth light source array, third and fourth platform, not shown) may translate relative to each other, with such translation effected by any number of actuators (e.g., electric motor, servo, etc.) controlled by control circuitry 518.

Figure 1D:
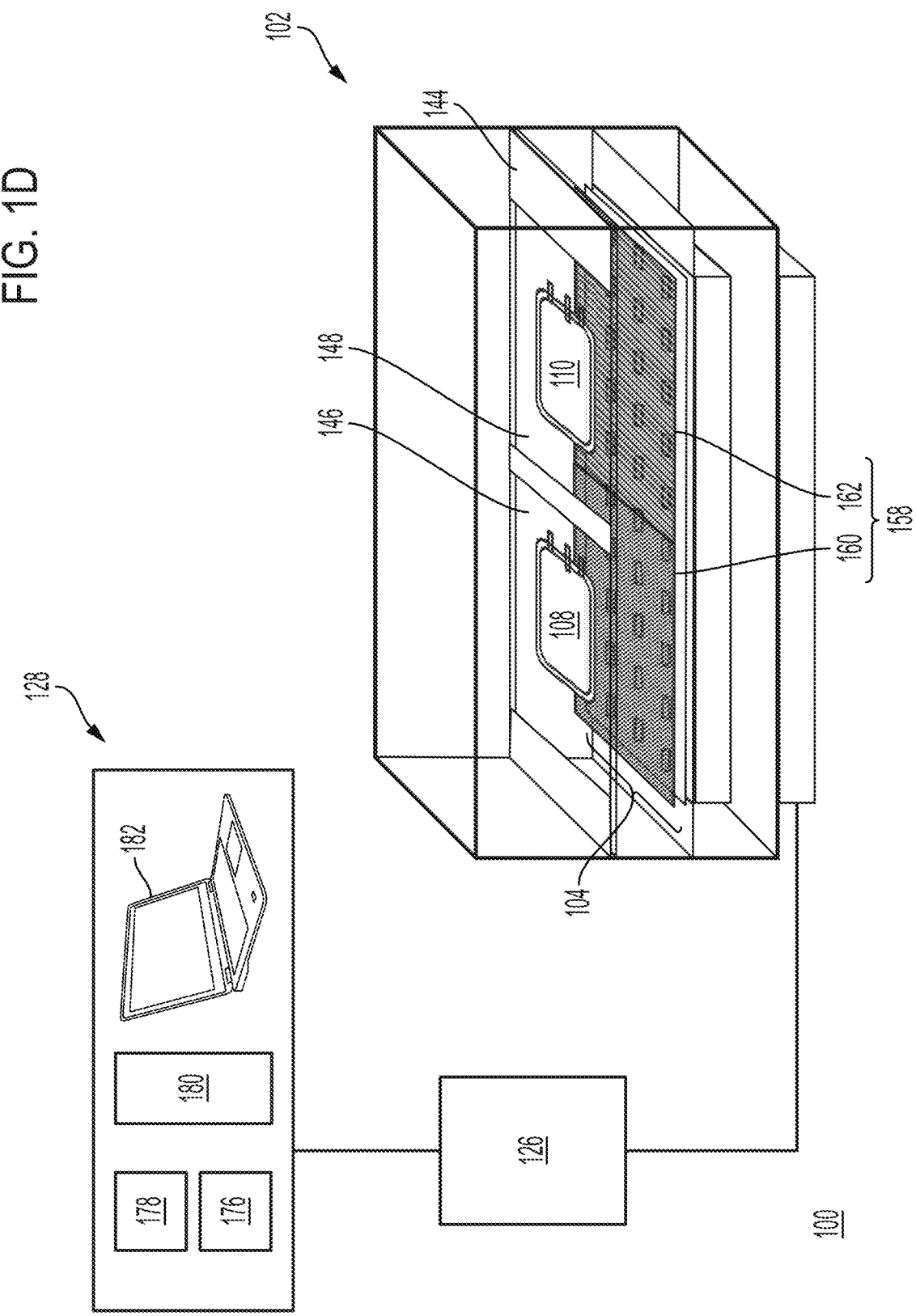
Figure 6B:
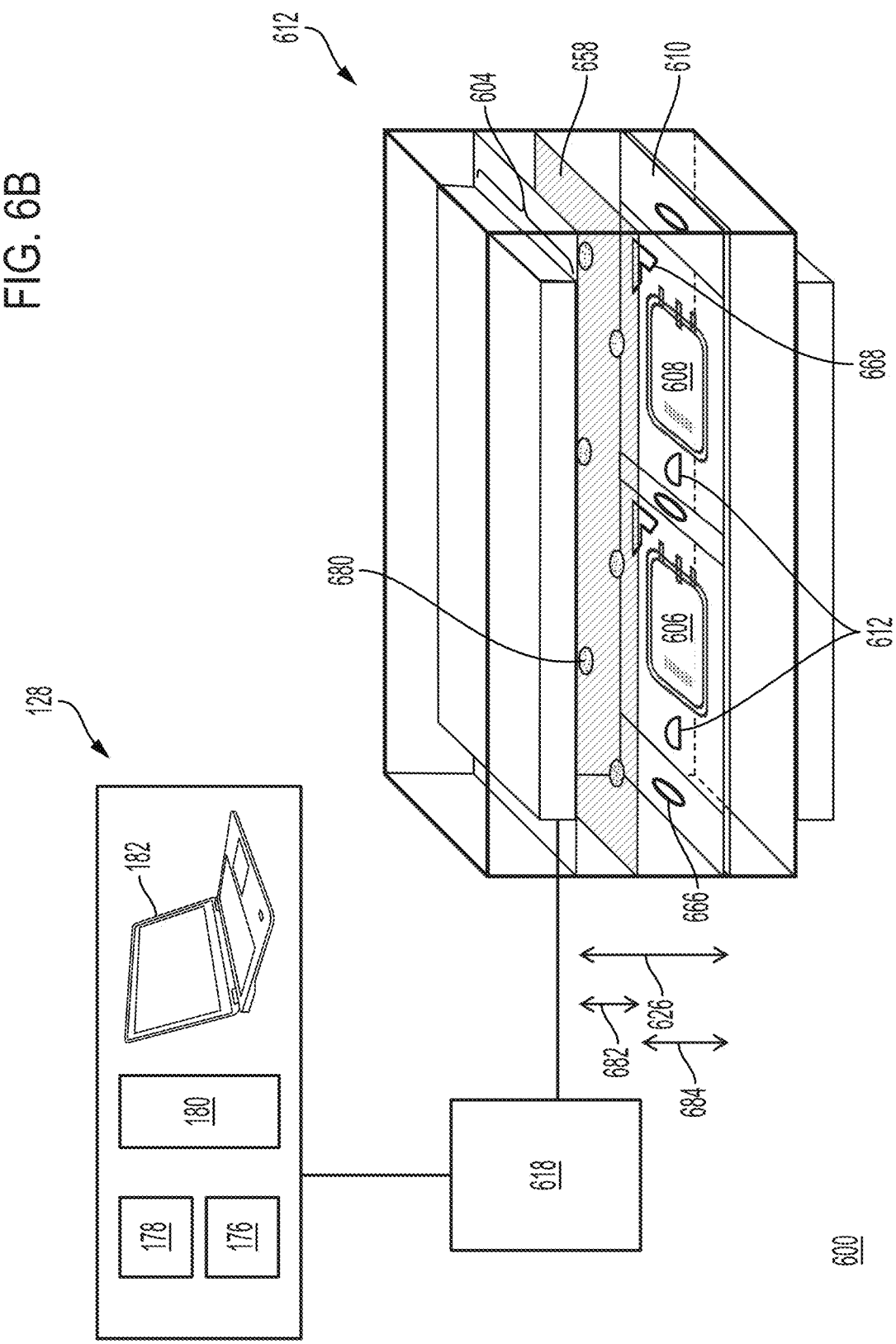

FIG. 6A shows a perspective view of an exemplary system 600 for treatment of one or more biological fluids 606 and 608 comprising a light source array 604 positioned in treatment chamber 612. Light source array 604 faces a platform 610 for biological fluids. Light source array 604 may be thermally coupled to heat exchanger 616. Treatment chamber 612 may include platform 610 positioned under light source array 604, the platform configured to hold one or more biological fluids 606 and 608. Treatment chamber 612, light source array 604, heat exchanger 616, and platform 610 may each be operatively coupled to control circuitry 618 that may adjust or set their respective parameters. FIG. 6B shows that exemplary system 600 may also include barrier 658 and various sensors 612, 666, 668, 680 in treatment chamber 612. Barrier 658 is positioned between array of light sources 604 and one or more biological fluids 606 and 608, and barrier 658 may have any of the characteristics discussed above for barrier 158 in FIG. 1D. Sensors 612, 666, 668 may be affixed to or positioned in platform 610. Sensors 680 may be affixed to (e.g., above or below) or positioned in barrier 658.

Light source array 604 may comprise an array of light source channels. Each light source channel of the light source array 604 may be configured to emit light of the various peak wavelengths discussed above and in the various arrangements of light sources and light source channels discussed above.

Light source array 604 and platform 610 may both be configured to translate relative to each other to increase or decrease distance 626 between them as in the translation discussed above. Platform 610 may be lowered to the bottom of treatment chamber 612, which may be raised from (e.g., by any structural base, including any components like sensors or circuitry), or flush with, an exterior bottom surface (e.g., floor, ground, desk, etc.). Lights source array 604 may be raised to the top of treatment chamber 612. In FIG. 6B, light source array 604, barrier 658, and platform 610 may all be configured to translate relative to each other to increase or decrease distances 626, 682, and 684 between any pair of: light source array 604, barrier 658, and platform 610. This translation may be effected by any number of actuators (e.g., electric motor, servo, etc.) controlled by control circuitry 618, which may separately control translation of light source array 604, barrier 658, and platform 610. In some embodiments, one or two of light source array 604, barrier 658, and platform 610 may be fixed in position in treatment chamber 612. For example, barrier 658 may be fixed in position in treatment chamber 612. As another example, barrier 658 and light source array 604 may be fixed in position relative to each other at a fixed distance 682 in treatment chamber 612 where platform 610 may be configured to translate to increase or decrease distances 626 and 684. As another example, barrier 658 and platform 610 may be fixed in position relative to each other at a fixed distance 684 in treatment chamber 612 where light source array 604 may be configured to translate to increase or decrease distances 626 and 682.

System 600 in FIGS. 6A-6B may be similar to system 100 in FIGS. 1A-1E in a number of ways including that, e.g., both system 600 and system 100 provide illumination of biological fluid onto one side: e.g., illumination onto one side of the container of the biological fluid, illumination onto one side of a platform. System 600 in FIGS. 6A-6B may be different from system 100 in FIGS. 1A-1E in a number of ways including that, e.g., system 600 provides illumination light onto biological fluid from above (e.g., above container of biological fluid, above a platform), but system 100 provides illumination from below (e.g., below container of biological fluid, below a platform).

System 600 in FIGS. 6A-6B may be similar to system 400 in FIG. 4 in a number of ways including that, e.g., both system 600 and system 400 provide illumination light onto biological fluid from above (e.g., above container of biological fluid, above a platform). System 600 in FIGS. 6A-6B may be different from system 400 in FIG. 4 in a number of ways including that, e.g., system 600 provides illumination of biological fluid onto one side, but not onto opposing sides as in system 400.

Providing illumination of biological fluids 606 and 608 from above may be desirable for any variety of reasons. For example, due to the downward force of gravity, biological fluids 606 and 608 may be stationary and passively resting on platform 610 (e.g., in containers, in wells, on tray). Thus, biological fluids 606 and 608 can be illuminated by light from above platform 610, and there may be no need for the light to pass through platform 610 to reach biological fluids 606 and 608. Loss and/or dispersion of illumination light energy due to platform 610 may be avoided. Additionally, there may be no need for platform 610 to be transparent or translucent to the illumination light. Platform 610 may be formed from materials and/or designs that are opaque to the illumination light.

Sensors

Figure 1E:
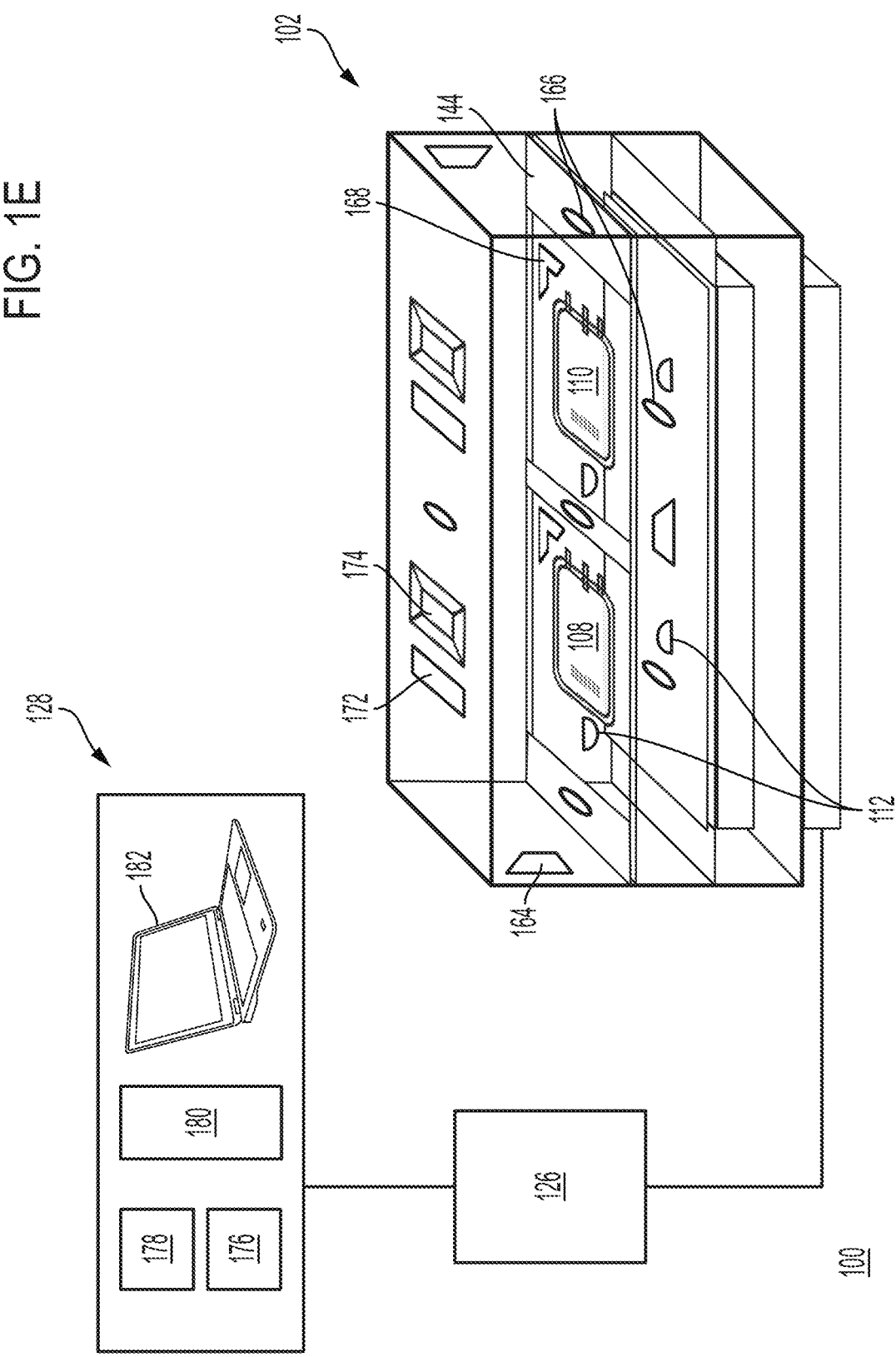

The exemplary embodiments of the systems discussed above may include one or more of various types of sensors implemented for their respective treatment chambers. Turning to FIG. 1E, each of the various types of sensors discussed below may be operatively coupled (directly or indirectly) to control circuitry 126 and/or computer system 128. Although various sensors are described below with respect to FIG. 1E, one of ordinary skill in the art will understand that the description may also apply to any other embodiments of the systems described above, as exemplified by the various sensors shown in FIG. 6B.

The various sensors that may be implemented for treatment chamber 102 include:

- one or more light sensors 112 configured to measure the light intensity at various portions of the treatment chamber and/or the light intensity incident on various portions of one or more biological fluids 108 and 110,
- one or more air flow sensors 164,
- one or more heat sensors 166 for measuring the temperature of treatment chamber 102 and/or the temperature of one or more biological fluids 108 and 110,
- one or more sensors 168 or 172 for detecting the presence of one or more biological fluids 108 and 110 (e.g. pressure sensors, optical retro-reflective sensors, optical transmissive sensors, label readers, barcode scanners, RFID sensors, etc.),
- one or more sensors 172 for detecting the type of one or more biological fluids 108 and 110 (e.g., label readers, barcode scanners, RFID sensors),
- one or more sensors 174 for detecting a property (e.g., transmissivity) of the biological fluid (e.g., optical sensors, spectroscopic sensors),
- one or more sensors 174 for detecting a photochemical compound in the biological fluid (e.g., fluorescence spectrometry), and
- one or more sensors 174 (e.g., ultrasonic sensors) positioned to detect the fluid depth of a portion (e.g., various portions) of one or more biological fluids 108 and 110.

Any of these various sensors may be positioned anywhere (e.g., external to, located inside, forming a part of the structure of a treatment chamber) for implementation with the various embodiments of the treatment chambers discussed above. For example, the one or more light sensors 112, the one or more heat sensors 166, and the one or more airflow sensors 164 may be positioned on array of light sources 104. As shown in FIG. 1E, in embodiments of treatment chamber 102 that include platform 144, the one or more light sensors 112 and the one or more sensors 168 for detecting the presence of the one or more biological fluids 108 and 110 may be positioned on platform 144. As shown in FIG. 6B, in embodiments of treatment chamber 612 that include platform 610 and barrier 658, one or more light sensors 612, one or more heat sensors 666, and one or more sensors 668 for detecting the presence of one or more biological fluids 606 and 608 may be affixed to or positioned in platform 610. Sensors 680, which may represent any of the various sensors discussed above, may be affixed to or positioned in barrier 658.

System Control and User Input

Mechanisms to control and adjust or set various parameters of the various components of the various embodiments of biological fluid treatment systems are now described. Although mechanisms to control and adjust or set various parameters of the various components of treatment system 100 are discussed below, one of ordinary skill in the art will understand that the below description may also apply to the adjustment of various parameters of the various other embodiments of the treatment systems discussed above.

In some embodiments, the various parameters of the various components of treatment system 100 may be dynamically or automatically adjusted or set based on feedback received at control circuitry 126 and/or computer system 128 from one or more of various types of sensors. Alternatively or additionally, the various parameters of the various components treatment system 100 may be adjusted or set based on user input at computer system 128.

Computer system 128 may be operatively coupled (directly or indirectly) to control circuitry 126 and/or to any of the various sensors discussed above. Computer system may include one or more processors 176, memory 178, an input/output (I/O) interface 180, and a user interface (UI) 182. One or more processors 176 may be one or more of any type of general-purpose computer processor. Memory, or computer readable medium 178 may include one or more of readily available memory such as random access memory (RAM), read-only memory (ROM), floppy disk, hard disk, optical storage media (e.g., compact disc or digital video disc), flash drive, or any other form of digital storage, local or remote. In some examples, a non-transitory computer-readable storage medium of memory 178 may be used to store instructions for illuminating one or more biological fluids in accordance with their one or more treatment profiles, as will be discussed below with reference to the flowcharts of FIGS. 7A-7B. Computer system 128 may encompass any variety of computers, such as a personal computer (PC), a desktop computer, a laptop, a computer terminal, a server computer, a tablet computer, a smartphone, a personal digital assistant (PDA), etc. In some examples, control circuitry 126 and/or the function of control circuitry 126 may be included within computer system 128.

Control circuitry 126 may be implemented as any suitable logic circuitry that can coordinate its control functionalities described herein. Such control functionalities can be provided via executing instructions implemented in a software program. Suitable logic circuitry may include a processor-readable medium storing the instructions implemented in the software program and processor(s) that, when executing the instructions, performs the control functionalities. Moreover, such control functionalities can also be provided via corresponding logic design implemented in hardware logic circuitry, such as a programmable logic device or an application-specific integrated circuit implementing logic designs that provide the control functionalities of control circuitry 126. Furthermore, such control functionalities can be provided via an implementation that combines both processor(s) running software and hardware logic circuitry.

In some examples, control circuitry 126 may include computer system 128 and/or the function of computer system 128.

At UI 182, a user may input one or more characteristics of a set of characteristics of one or more biological fluids 108 and 110. Alternatively, or additionally, the one or more characteristics of a set of characteristics of one or more biological fluids may be determined based on feedback input to computer system 128 and/or control circuitry 126 from one or more sensors for treatment chamber 102. The characteristics of the set of characteristics of a biological fluid may include, for example, the type of the biological fluid (e.g., blood product, such as plasma, platelets, red blood cells; cells, such as eukaryotic cells; proteins, such as antibodies; vaccines), the photochemical agent in the biological fluid (e.g., type, volume, concentration), the volume of the biological fluid, the transmissivity of the biological fluid, the type and/or shape of the container carrying the biological fluid, and the temperature of the biological fluid.

At UI 182, a user may input one or more parameters that comprise the treatment profiles of one or more biological fluids 108 and 110. Alternatively or additionally, computer system 128 may automatically determine one or more parameters of the one or more treatment profiles of one or more biological fluids 108 and 110 based on the respective set of characteristics of the one or more biological fluids 108 and 110. In particular, memory 178 may store a computer program comprising instructions that map one or more characteristics of a biological fluid to one or more parameters of a treatment profile of the biological fluid for each biological fluid. The instructions that that map one or more characteristics of a biological fluid to one or more parameters of a treatment profile of the biological fluid for each biological fluid may be implemented as a set of user-programmable rules.

Computer system 128 may send control instructions and/or control signals to control circuitry 126 to adjust or set various parameters of treatment chamber 102. In some embodiments, the various parameters of treatment chamber 102 may be adjusted or set based on the treatment profiles of one or more biological fluids 108 and 110 positioned in the treatment chamber. Alternatively or additionally, the various parameters of treatment chamber 102 may be adjusted or set based on feedback from various sensors positioned within treatment chamber 102.

Control circuitry 126 may adjust or set a peak wavelength of light emitted by each light source channel 106. Control circuitry 126 may adjust or set the intensity of light emitted by each light source channel 106. In particular, control circuitry 126 may adjust or set the intensity of light emitted by each light source channel 106 from the "off" state (0% intensity) to the maximum intensity state (100% intensity) in 0.4% increments. Control circuitry 126 may adjust or set the tilt angle of each light source channel 106 by physically re-orienting the light source channel 106 or by tuning the output direction of the light source channel 106. For example, the control circuitry may adjust or set the tilt angle of each light source channel with respect to a normal direction of (e.g., perpendicular to) a surface each light source channel is disposed on from 0° to 5°. Control circuitry 126 may adjust or set the duration of emission of light emitted by each light source channel 106. Control circuitry 126 may adjust or set the spectral bandwidth of emission of light emitted by each light source channel 106. Any of these parameters may be adjusted or set based on a set of parameters received from, for example, one or more light sensors 112 positioned within treatment chamber 102, and/or any of the other various sensors positioned within treatment chamber 102.

Enabling individual control of one or more of: the peak wavelength of emission, the duration of emission, the intensity of emission, and the angle of emission light from each light source channel 106 allows programming and control of various temporally and/or spatially varying light characteristics of light emitted by light source array 104. These light characteristics may be an important treatment parameter in the treatment profiles of biological fluids, and may be programmed by a user at computer system 128 and stored in memory 178. The light characteristics of one or more biological fluids may be automatically determined at computer system 128 based on a respective set of characteristics of the one or more biological fluids.

In an exemplary set of light characteristics, all light sources of array of light sources 104 may be turned on and off at the same time with a user adjustable frequency to generate a strobing output pattern. In another exemplary set of light characteristics, the intensity of light emitted by each light source channel may be temporally modulated to create a sinusoidal intensity output pattern. In another exemplary set of light characteristics, first set of light sources 152 of array of light sources 104 may illuminate a portion of first biological fluid 108 facing first set of light sources 152 with a first intensity, and second set of light sources 154 of array of light sources 104 may illuminate second biological fluid 110 facing second set of light sources 154 with a second intensity.

Adjustment of the various parameters of treatment chamber 102 may be performed by control circuitry 126 before illuminating the one or more biological fluids 108 and 110 in the treatment chamber 102. Such initial adjustments by control circuitry 126 may include, for example, instructing or controlling the heating/cooling unit 114 to adjust or set the temperature of treatment chamber 102, instructing or controlling array of light sources 104 to move closer to or further from one or more biological fluids 108 and 110, instructing or controlling pumps 142 to flow the biological fluid from source container 136 to treatment container 132, instructing or controlling the platform 144 to agitate the one or more biological fluids 108 and 110, and instructing or controlling each light source channel 106 to adjust or set the intensity of light from the "off" state to an initial intensity state.

Adjustment of the various parameters by control circuitry 126 may also be performed while the one or more biological fluids 108 and 110 are being illuminated. Such adjustments by control circuitry 126 may be dynamically made based on feedback received at computer system 128 and/or at control circuitry 126 from the various sensors discussed above. In particular, memory 178 may store a set of user-programmable rules that map input from various sensors to required adjustments of various components of treatment chamber 102. Enabling dynamic feedback response to data received by various sensors may advantageously allow for rapid correction by control circuitry 126 of treatment parameters that deviate from the intended treatment profiles of one or more biological fluids 108 and 110 being treated. This in turn may provide improved inactivation of pathogens in the one or more biological fluids being treated, while minimizing the exposure of the one or more biological fluids to treatment chamber conditions that may affect (e.g., reduce, impair, damage) biological function and/or desirable characteristics of the biological fluid.

Examples of dynamic control by control circuitry 126 of various parameters of treatment chamber 102 based on feedback from various sensors are now described.

In some examples, the adjustment of light intensity emitted by each light source channel 106 by control circuitry 126 may be based on data received by computer system 128 from the one or more light sensors 112. For example, if the light intensity incident on a portion of biological fluid 108 detected by one or more light sensors 114 is greater or less than a threshold value, control circuitry 126 may respectively decrease or increase the light intensity of one or more light sources of array of light sources 104 facing that portion of biological fluid 108. Alternatively or additionally, control circuitry 126 may increase or decrease distance 156 between platform 144 carrying biological fluid 108 and array of light sources 104 to change the intensity of light incident on that portion of biological fluid 108. The threshold intensity value may be based on, for example, one or more of: the depth of that portion of biological fluid 108, the type of biological fluid 108, the transmissivity of the biological fluid 108, the transmissivity of the container carrying the biological fluid 108, and the type of pathogen inactivation compound admixed with biological fluid 108. The threshold intensity value may be specified in the treatment profile of biological fluid 108 and/or in the set of characteristics of biological fluid 108. Suitable light sensors are well known in the art, such as for example photodiodes with a spectral response range that corresponds to (e.g., includes) the wavelength(s) of light sources provided herein (e.g., photodiode with spectral response range of 210-390 nm). Exemplary photodiodes may include silicon photodiodes, silicon carbide photodiodes, or other suitable photodiodes such as GaAsP photodiodes, GaP photodiodes, and GaN photodiodes.

In some examples, the intensity of light emitted by each light source channel 106 of array of light sources 104 may be adjusted or set by control circuitry 126 based on depth data received by computer system 128 from one or more depth sensors 174. Enabling depth dependent intensity control may be desirable in embodiments where container 130 carrying biological fluid 108 may vary in depth (e.g., maximum depth), for example due to different volumes of biological fluid (e.g., volumes less than capacity of a container carrying the biological fluid), and/or is non-uniform in depth (e.g., a blood bag). In particular, due to the characteristic central bulge of a blood bag, the central portions of the biological fluid in the blood bag have may a greater depth than the peripheral portions of the biological fluid in the blood bag. Consequently, the intensity of illumination required for sufficient pathogen inactivation for the biological fluid in the central region may be greater than the intensity of illumination required for sufficient pathogen inactivation for the biological fluid in the peripheral region. Accordingly, the one or more depth sensors 174 may detect this variation in fluid depth across container 130 and control circuitry 126 may adjust or set the intensity of emission of each light source facing various portions of the biological fluid 108 based on the detected depth of such portions. Alternatively, or in addition, a container of a particular capacity (e.g., 1000 mL) containing a volume of biological fluid less than (e.g., 300 mL) the container capacity, may have a depth less than for a volume of biological fluid closer to (e.g., 900 mL) the container capacity. Consequently, the intensity of illumination required for sufficient pathogen inactivation for the biological fluid of a larger volume may be greater than the intensity of illumination required for sufficient pathogen inactivation for the biological fluid of a smaller volume carried within a container of similar size.

Accordingly, the one or more depth sensors 174 may detect the fluid depth in container 130, and control circuitry 126 may adjust or set the intensity of emission of each light source facing the biological fluid 108 based on the detected depth.

Depth dependent intensity control and dynamic intensity adjustment by control circuitry 126 may also be important in examples where it is desirable to agitate biological fluids either continuously or periodically during treatment. In particular, in embodiments where biological fluid 108 is agitated during treatment, biological fluid 108 may develop a sloshing or wave motion, which may result in a standard wave pattern. Such motion may result in varying depths across various portions of biological fluid 108, thus changing the light energy dosage sufficient for inactivation of pathogens within such portions. Accordingly, based on feedback from one or more depth sensors 174, control circuitry 126 may dynamically adjust or set the intensity of light emitted by one or more light source channels 106. For example, the intensity of light emitted by one or more light source channels facing a portion of biological fluid 108 may be dynamically increased or decreased by control circuitry 126 based on whether the depth of that portion of biological fluid 108 detected by one or more depth sensors 174 is greater or less than a threshold depth. The threshold depth may be specified in the treatment profile of biological fluid 108 and/or in the set of characteristics of biological fluid 108. Alternatively, or additionally, a standard wave pattern may be determined based on variables, such as for example, biological fluid volume, biological fluid type, container size, container shape, agitation speed, agitation pattern and agitation stroke length, and computer system 128 may send control instructions and/or control signals to control circuitry 126 to adjust or set the intensity of light emitted by one or more light source channels using a set of user-programmable rules based on such wave patterns.

In some examples, the temperature of treatment chamber 102 and/or the temperature of the one or more biological fluids 108 and 110 may be adjusted or set by control circuitry 126 based on data received at computer system 128 from one or more heat sensors 166. Suitable heat sensors are well known in the art, such as for example a LM74 temperature sensor (Texas Instruments, Inc). For example, if the temperature of biological fluid 108 detected by one or more heat sensors 166 exceeds a threshold temperature, control circuitry 108 may adjust or set various operational parameters of treatment chamber 102 to lower the temperature of biological fluid 108. For example, control circuitry 108 may increase distance 156 between array of light sources 104 and biological fluid 108 and/or instruct or control the heating/cooling unit 114 to decrease the temperature of treatment chamber 102. Alternatively or additionally, control circuitry 126 may instruct or control heat exchanger 122 to increase the rate of heat transfer between array of light sources 104 and heat exchanger 122.

Although specific examples of how feedback from various sensors may cause control circuitry 126 to adjust or set various parameters of various components of treatment chamber 102 have been discussed above, these examples are not meant to be limiting. It should be understood that control circuitry 126 may adjust or set any of the various adjustable parameters of the possible components of the various embodiments of the treatment systems discussed above based on feedback data detected by any of the various sensors discussed above and/or based on any user input provided at UI 182 at computer system 128.

Methods for Treating Biological Fluids

Various methods used to treat biological fluids to sufficiently inactivate one or more pathogens present in biological fluids are discussed below. The below methods may optionally be performed using the various embodiments of the systems discussed above. However, the below described methods are not required to be performed by the various embodiments of the systems discussed above, and may be performed using any system capable of performing the below described methods.

Figure 7A:
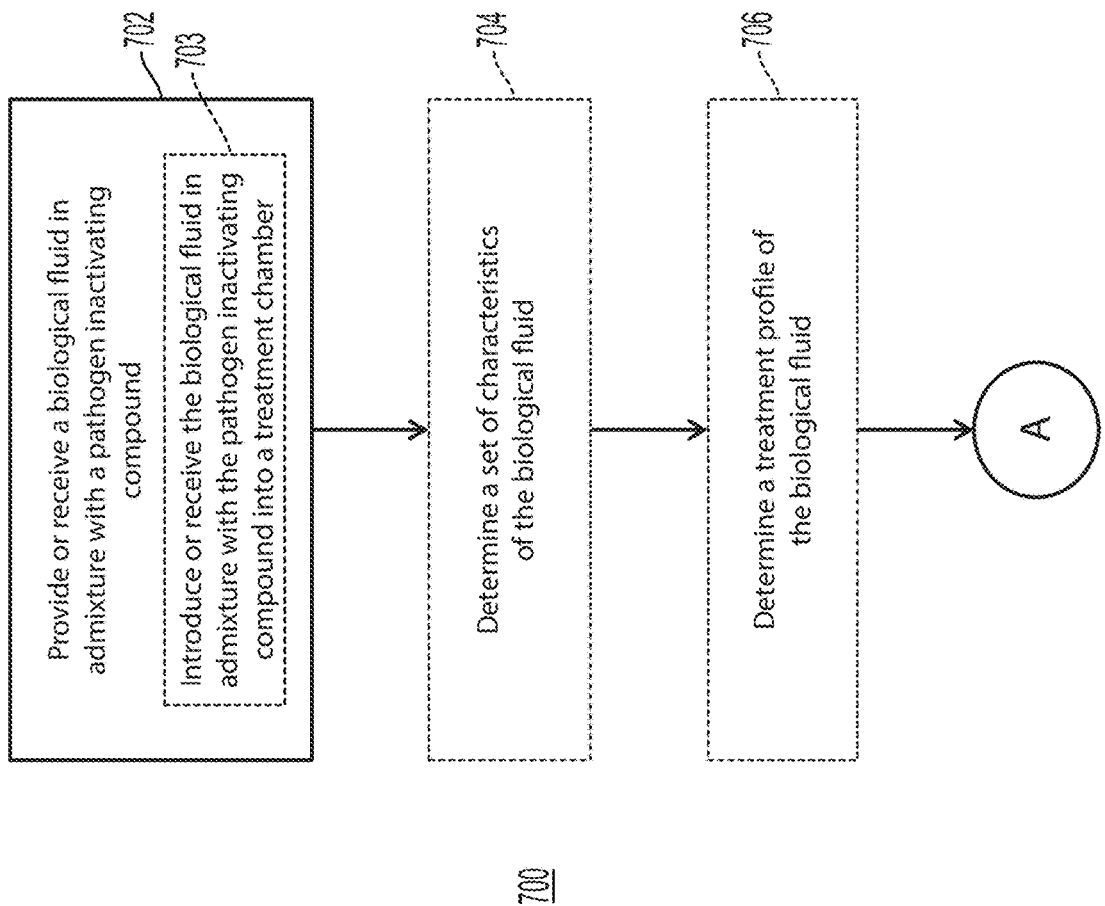
FIGS. 7A-7B are flowcharts depicting exemplary methods for treating biological fluids.
Figure 7B:
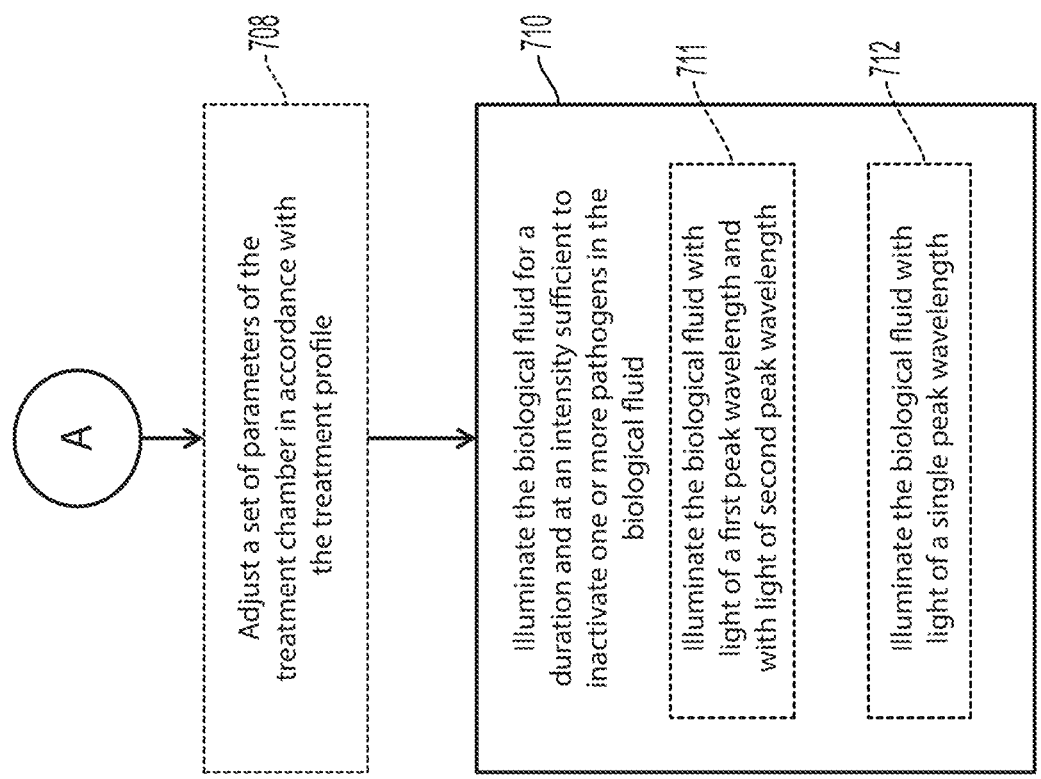

FIGS. 7A-7B are flow diagrams representing methods 700 for treating biological fluids according to certain implementations. In various implementations, some operations in the method may be combined and/or the order of some operations may be changed from the order shown in FIGS. 7A-7B. Also, in some implementations, operations shown in separate boxes/figures and/or discussed in association with separate methods may be combined to form other methods, and operations shown in the same boxes/figures and/or discussed in association with the same method may be separated into different methods.

At FIG. 7A, at step 702, a biological fluid in admixture with one or more pathogen inactivation compounds (hereinafter "the biological fluid") may be provided or received. In embodiments where a treatment chamber (such as chamber 102) is used to treat the biological fluid, step 702 may include optional step 703 where the biological fluid is introduced into or received by treatment chamber 102. For example, referring to FIG. 1C, in embodiments where treatment chamber 102 includes slidably movable platform 144, slidably movable platform 144 may be slid out of the treatment chamber, biological fluid 108 (e.g., biological fluid in a container) may be placed on the slidably moveable platform 144, and the platform may be slid back into treatment chamber 102.

In another example, in embodiments including multiple containers 132, 136, and 138, optional step 703 may comprise flowing biological fluid 110 into treatment chamber 102 from source container 136.

At optional step 704, a set of characteristics of the biological fluid may be determined. Determining one or more characteristics of the set of characteristics of a biological fluid may be based on user input at computer system 128 and/or based on feedback from the various types of sensors discussed above. For example, in embodiments wherein treatment chamber 102 includes one or more biological fluid type sensors 170, the one or more type sensors 170 may determine the type of the biological fluid.

In another example, the set of characteristics of the biological fluid may be determined using barcode scanner 172. In particular, barcode sensor 172 may scan barcode 134 on biological fluid container 130 to determine an identifier of biological fluid 108 and transmit this identifier to computer system 128. Computer system 128 may then determine the set of characteristics of biological fluid 108 based on a list stored in memory 178 that associates identifiers of one or more biological fluids with their respective set of characteristics.

At optional step 706, a treatment profile for the biological fluid may be determined. Determining the treatment profile may comprise determining any one or more of the parameters comprising the treatment profile discussed above. For example, determining the treatment profile may comprise determining one or more peak wavelengths of light to be used in illuminating the biological fluid. Determining the treatment profile may comprise determining one or more intensities of light at which to emit light at the one or more peak wavelengths. Determining the treatment profile may comprise determining one or more durations of emission at which to emit light at one or more peak wavelengths.

In some examples, determining the treatment profile for the biological fluid may be based on the set of characteristics of the biological fluid. For example, after computer system 128 determines the set of characteristics of the biological fluid, computer system 128 may use a set of programmable rules to determine the treatment profile of the biological fluid. The set of programmable rules may determine one or more parameters of the treatment profile based on one of more characteristics of the set of characteristics of the biological fluid. For example, a programmable rule may match a certain type of photochemical agent to a certain peak wavelength of light, a certain duration of emission, and a certain intensity of emission of that peak wavelength of light sufficient to inactivate a pathogen in the biological fluid admixed with that photochemical agent. In another example, a programmable rule may match the depth of a portion of the biological fluid to a certain intensity of light sufficient to inactivate a pathogen in that portion of the biological fluid.

In other examples, the one or more parameters of the treatment profile may be entered by the user at computer system 128.

Turning to FIG. 7B, in examples where treatment chamber 102 is used to treat the biological fluid, at optional step 708, a set of parameters of treatment chamber 102 may be adjusted or set by control circuitry 126 based on the treatment profile. The parameters of the set of parameters that may be adjusted or set based on the treatment profile may include, whether to agitate the biological fluid, one or more parameters associated with the agitation of the biological fluid (e.g., the frequency of the agitating motion and the type of the agitating motion), the temperature of treatment chamber 102, and a distance between array of light sources 104 and platform 144.

At step 710, the biological fluid (e.g., biological fluid admixture with photoactive pathogen inactivation compound) is illuminated for a duration and at an intensity (e.g., to provide a light dose, to provide a total light dose) sufficient to inactivate one or more pathogens in the biological fluid. In some embodiments, the illumination of the biological fluid is performed in accordance with the treatment profile.

In some examples, step 710 may comprise step 711, where the biological fluid may be illuminated with light of a first peak wavelength and illuminated with light of a second peak wavelength. In some embodiments of any of the methods provided herein, the first peak wavelength may differ from the second peak wavelength by at least (e.g., greater than) 5 nm, 10 nm, 15 nm, 20 nm or 25 nm or more. In some embodiments of any of the methods provided herein, light of the second peak wavelength is emitted by the one or more second light sources, each emitting light having a full-width half-maximum (FWHM) spectral bandwidth of less than 20 nanometers, and wherein the second peak wavelength different from the first peak wavelength by at least 5 nm, such as at least any of 10 nm, 15 nm, 20 nm or 25 nm. The first peak wavelength may be in the visible light spectrum or in the ultraviolet spectrum, such as for example, the ultraviolet A spectrum, the ultraviolet B spectrum, or the ultraviolet C spectrum. Similarly, the second peak wavelength may be in the visible light spectrum or in the ultraviolet spectrum, such as for example, the ultraviolet A spectrum, the ultraviolet B spectrum, or the ultraviolet C spectrum. In some embodiments, the first peak wavelength and/or the second peak wavelength may be between about 240 nm and about 250 nm, about 245 nm and about 255 nm, about 250 nm and about 260 nm, about 255 nm and about 265 nm, about 260 nm and about 270 nm, about 265 nm and about 275 nm, about 270 nm and about 280 nm, or about 275 nm and about 285 nm. In some embodiments, the first peak wavelength and/or the second peak wavelength may be between about 280 nm and about 290 nm, about 285 nm and about 295 nm, about 290 nm and about 300 nm, about 300 nm and about 310 nm, about 305 nm and about 315 nm, or about 310 nm and about 320 nm. In some embodiments, the first peak wavelength and/or the second peak wavelength may be between about 315 nm and about 325 nm, about 320 nm and about 330 nm, about 325 nm and about 335 nm, about 330 nm and about 340 nm, about 335 nm and about 345 nm, about 340 nm and about 350 nm, about 345 nm and about 355 nm, about 350 nm and about 360 nm, about 355 nm and about 365 nm, about 360 nm and about 370 nm, about 365 nm and about 375 nm, about 370 nm and about 380 nm, about 375 nm and about 385 nm, about 380 nm and about 390 nm, about 385 nm and about 395 nm, about 390 nm and about 400 nm. In some embodiments, the first peak wavelength and/or the second peak wavelength may be about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, or about 400 nm. In some embodiments, the first peak wavelength and/or the second peak wavelength may be between about 255 nm and about 275 nm (e.g., between about 260 nm and about 270 nm, 265 nm). In some embodiments, the first peak wavelength and/or the second peak wavelength may be between about 275 nm and about 295 nm (e.g., between about 280 nm and about 290 nm, 285 nm). In some embodiments, the first peak wavelength and/or the second peak wavelength may be between about 300 nm and about 320 nm (e.g., between about 305 nm and about 315 nm, 310 nm). In some embodiments, the first peak wavelength and/or the second peak wavelength may be between about 315 nm and about 335 nm (e.g., between about 320 nm and about 330 nm, 325 nm). In some embodiments, the first peak wavelength and/or the second peak wavelength may be between about 330 nm and about 350 nm (e.g., between about 335 nm and about 345 nm, 340 nm). In some embodiments, the first peak wavelength and/or the second peak wavelength may be between about 355 nm and about 375 nm (e.g., between about 360 nm and about 370 nm, 365 nm). In some embodiments, the first peak wavelength and/or the second peak wavelength may be between about 375 nm and about 395 nm (e.g., between about 380 nm and about 390 nm, 385 nm). In some embodiments, the first peak wavelength and/or the second peak wavelength may be between about 315 nm and about 350 nm.

In some embodiments of any of the methods provided herein, the total dose of ultraviolet light illuminating the biological fluid emitted by the set of one or more first light source is about 0.5 $J/cm^2$ to about 50 $J/cm^2$, such as any of about 0.5 $J/cm^2$ to about 10 $J/cm^2$, about 0.5 $J/cm^2$ to about 15 $J/cm^2$, about 0.5 $J/cm^2$ to about 25 $J/cm^2$, about 1 $J/cm^2$ to about 10 $J/cm^2$, about 1 $J/cm^2$ to about 15 $J/cm^2$, about 1 $J/cm^2$ to about 25 $J/cm^2$, about 3 $J/cm^2$ to about 10 $J/cm^2$, about 3 $J/cm^2$ to about 15 $J/cm^2$, about 3 $J/cm^2$ to about 25 $J/cm^2$, about 5 $J/cm^2$ to about 10 $J/cm^2$, about 5 $J/cm^2$ to about 15 $J/cm^2$, about 5 $J/cm^2$ to about 25 $J/cm^2$, about 10

J/cm² to about 30 J/cm², about 10 J/cm² to about 20 J/cm², about 15 J/cm² to about 50 J/cm², about 15 J/cm² to about 35 J/cm², about 20 J/cm² to about 30 J/cm², about 25 J/cm² to about 50 J/cm², about 30 J/cm² to about 40 J/cm², or about 40 J/cm² to about 50 J/cm². In some embodiments, the total dose of ultraviolet light illuminating the biological fluid emitted by the set of one or more first light source is about 0.5 J/cm² or more, such as about any of 1 J/cm² or more, 2 J/cm² or more, 3 J/cm² or more, 4 J/cm² or more, 5 J/cm² or more, 6 J/cm² or more, 7 J/cm² or more, 8 J/cm² or more, 9 J/cm² or more, 10 J/cm² or more, 15 J/cm² or more, 20 J/cm² or more, 25 J/cm² or more, 30 J/cm² or more, 35 J/cm² or more, 40 J/cm² or more, 45 J/cm² or more, or 50 J/cm² or more. In some embodiments, the total dose of ultraviolet light illuminating the biological fluid emitted by the set of one or more first light source is less than about 50 J/cm², less than about 40 J/cm², less than about 30 J/cm², less than about 25 J/cm², less than about 20 J/cm², less than about 15 J/cm², or less than about 10 J/cm². In some embodiments, illuminating the biological fluid occurs for a duration and at an intensity sufficient to provide a total dose (e.g., aforementioned total dose) of ultraviolet light illuminating the biological fluid (e.g., any suitable combination of duration and intensity sufficient to provide the total dose of ultraviolet light). In some embodiments, the intensity is between 1 and 1000 mW/cm² (e.g., between 1 and 100 mW/cm²). In some embodiments, the duration is between 1 second and 2 hours (e.g., between 1 minute and 60 minutes).

In some embodiments of any of the methods provided herein, the light of the first peak wavelength and the light of the second peak wavelength may be respectively provided by a first light source and a second light source. The first light source and/or the second light source may be, for example, solid-state lighting (SSL), light-emitting diodes (LEDs), organic light-emitting diodes (OLEDs), polymer light-emitting diodes (PLEDs), or laser diodes. In some examples, the first light source and the second light source may be included in light source channels 106 of light source array 104.

In some embodiments of any of the methods provided herein, the first and the second light sources may emit light with a narrow spectral bandwidth. In some examples, the full-width half maximum (FWHM) spectral bandwidth of light (e.g., spectral bandwidth at the maximum peak intensity) emitted by the first light source and/or the second light source may be less than 20 nm, less than 18 nm, less than 16 nm, less than 14 nm, less than 12 nm, less than 10 nm, less than 9 nm, less than 8 nm, less than 7 nm, less than 6 nm, or less than 5 nm. In some embodiments, the full-width half maximum (FWHM) spectral bandwidth of light emitted by the first light source and/or the second light source within 10 nm less than, within 10 nm greater than the peak wavelength of the first light source and/or second light source, respectively (e.g., no more than 10 nm greater than, no more than 10 nm less than the peak wavelength of the first light source and/or second light source, respectively). In some embodiments, the full-width at half maximum (FWHM) spectral bandwidth of light emitted by the first light source and/or the second light source may be greater than 1 nm, greater than 2 nm, greater than 3 nm, or greater than 4 nm, or more. In other examples, the intensity of light at 50% of the maximum peak intensity of light emitted by the first light source and/or the second light source may be within 10 nanometers of the peak wavelength of light emitted by the first and/or the second light source.

In some examples, illuminating the biological with light of the first peak wavelength and with light of the second peak wavelength occurs sequentially. In other examples, illuminating the biological fluid with light of the first peak wavelength and with light of the second peak wavelength occurs concurrently. In other examples, illuminating the biological fluid with light of the first peak wavelength and illuminating the biological fluid with light of the second peak wavelength partially overlaps (e.g., illuminating only (from among light sources of the treatment chamber) with light of the first peak wavelength for a period of time, followed by light of both the first and second peak wavelengths for a period of time, followed by only (from among light sources of the treatment chamber) light of the second peak wavelength for a period of time).

In some embodiments of any of the methods provided herein, illuminating the biological fluid with light of the first peak wavelength may occur for a first duration and illuminating the biological fluid with light of the second peak wavelength may occur for a second duration. The first duration may be equal to or different from the second duration. In some examples, the first duration may be at least 1.5, 2, 2.5, 3, 3.5, 4, 4.5, 5, 6, 7, 8, 9, or 10 or more times longer than the second duration. In other examples, the second duration may be at least 1.5, 2, 2.5, 3, 3.5, 4, 4.5, 5, 6, 7, 8, 9, or 10 or more times longer than the first duration.

In some examples, illuminating the biological fluid with light of the first peak wavelength and the second peak wavelength may be performed in accordance with the treatment profile. For example, the treatment profile may specify the light characteristics to be used in illuminating the biological fluid. An exemplary treatment profile may specify to first illuminate the biological fluid with light of a first peak wavelength for a first duration at a first intensity, and then to illuminate the biological fluid with light of a second peak wavelength for a second duration at a second intensity. Another exemplary treatment profile may specify to illuminate the biological fluid with light of a first peak wavelength for a first duration at a first intensity, and concurrently (e.g., overlapping at least in part) to illuminate the biological fluid with light of a second peak wavelength for a second duration at a second intensity. In some embodiments, the treatment profile may specify one or more agitation conditions to be used before, during and/or after illuminating the biological fluid. An exemplary treatment profile may specify one or more agitation conditions to be used before, during and/or after illuminating the biological fluid with light of a first peak wavelength, and one or more agitation conditions to be used before, during and/or after illuminating the biological fluid with light of a second peak wavelength.

In some embodiments of any of the methods provided herein, the biological fluid may be illuminated with light of a single peak wavelength (e.g., first peak wavelength). In some examples, step 710 may comprise step 712, wherein the biological fluid may be illuminated with light of a single peak wavelength (e.g., first peak wavelength). The single peak wavelength (e.g., first peak wavelength) may be in the visible light spectrum or in the ultraviolet spectrum, the ultraviolet A spectrum, the ultraviolet B, spectrum, the ultraviolet C spectrum. In other examples, the single peak wavelength (e.g., first peak wavelength) may be between about 240 nm and about 250 nm, about 245 nm and about 255 nm, about 250 nm and about 260 nm, about 255 nm and about 265 nm, about 260 nm and about 270 nm, about 265 nm and about 275 nm, about 270 nm and about 280 nm, or about 275 nm and about 285 nm. In some embodiments, the single peak wavelength (e.g., first peak wavelength) may be between about 280 nm and about 290 nm, about 285 nm and about 295 nm, about 290 nm and about 300 nm, about 300 nm and about 310 nm, about 305 nm and about 315 nm, or about 310 nm and about 320 nm. In some embodiments, the single peak wavelength (e.g., first peak wavelength) may be between about 315 nm and about 325 nm, about 320 nm and about 330 nm, about 325 nm and about 335 nm, about 330 nm and about 340 nm, about 335 nm and about 345 nm, about 340 nm and about 350 nm, about 345 nm and about 355 nm, about 350 nm and about 360 nm, about 355 nm and about 365 nm, about 360 nm and about 370 nm, about 365 nm and about 375 nm, about 370 nm and about 380 nm, about 375 nm and about 385 nm, about 380 nm and about 390 nm, about 385 nm and about 395 nm, about 390 nm and about 400 nm. In some embodiments, the single peak wavelength (e.g., first peak wavelength) may be about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, or about 400 nm. In some embodiments, the single peak wavelength (e.g., first peak wavelength) may be between about 255 nm and about 275 nm (e.g., between about 260 nm and about 270 nm, 265 nm). In some embodiments, the single peak wavelength (e.g., first peak wavelength) may be between about 275 nm and about 295 nm (e.g., between about 280 nm and about 290 nm, 285 nm). In some embodiments, the single peak wavelength (e.g., first peak wavelength) may be between about 300 nm and about 320 nm (e.g., between about 305 nm and about 315 nm, 310 nm). In some embodiments, the single peak wavelength (e.g., first peak wavelength) may be between about 315 nm and about 335 nm (e.g., between about 320 nm and about 330 nm, 325 nm). In some embodiments, the single peak wavelength (e.g., first peak wavelength) may be between about 330 nm and about 350 nm (e.g., between about 335 nm and about 345 nm, 340 nm). In some embodiments, the single peak wavelength (e.g., first peak wavelength) may be between about 355 nm and about 375 nm (e.g., between about 360 nm and about 370 nm, 365 nm). In some embodiments, the single peak wavelength (e.g., first peak wavelength) may be between about 375 nm and about 395 nm (e.g., between about 380 nm and about 390 nm, 385 nm). In some embodiments, the single peak wavelength (e.g., first peak wavelength) may be between about 315 nm and about 350 nm.

In some embodiments of any of the methods provided herein, the light of the single peak wavelength (e.g., first peak wavelength) may be provided by a first light source. In some examples, the first light source may be the only light source of the treatment chamber 102 used to illuminate the biological fluid. The first light source may be, for example, one or more solid-state lights (SSL), light-emitting diodes (LEDs), organic light-emitting diodes (OLEDs), polymer light-emitting diodes (PLEDs), or laser diodes. For example, the first light source may be included in the light source channels 106 of array of light sources 104. As shown in FIGS. 1A-1E, the light source channels 106 may face only one side of container 130 carrying the biological fluid 108.

The first light source may emit light with a narrow spectral bandwidth. In particular, the intensity of light at 50% of the maximum peak intensity of light emitted by the first light source may be emitted at a wavelength of less than 10, 20, 30, or 40 nanometers from the peak wavelength of light emitted by the first light source. In other examples, the full-width at half maximum (FWHM) spectral bandwidth of light emitted by the first light source light source may be less than 20 nm, 18 nm, 16 nm, 14 nm, 12 nm, 10 nm, 9 nm, 8 nm, 7 nm, 6 nm, 5 nm, or less than 5 nm.

In some embodiments of any of the methods provided herein, the method for treating is sufficient to inactivate at least about 1 log of a pathogen, if present (e.g., when present), such as at least about any of 2 logs, 3 logs, 4 logs, 5 logs, 6 logs, 7 logs, 8 logs, 9 logs, or 10 logs (e.g., after the admixture is exposed to light sufficient to photochemically inactivate the pathogen). In some embodiments, the method for treating is sufficient to inactivate at least about 1 log of a pathogen, if present (e.g., when present), such as at least about any of 2 logs, 3 logs, 4 logs, 5 logs, 6 logs, 7 logs, 8 logs, 9 logs, or 10 logs, and wherein the biological fluid comprises about 5 M or less, such as about any of 4 μM or less, 3 μM or less, 2 μM or less, or 1 μM or less of PIC, after illumination. In some embodiments, the method for treating is sufficient to inactivate at least about 1 log of a pathogen, if present (e.g., when present), such as at least about any of 2 logs, 3 logs, 4 logs, 5 logs, 6 logs, 7 logs, 8 logs, 9 logs, or 10 logs, wherein a concentration of the pathogen inactivation compound in admixture with the biological fluid prior to illuminating is about 15 μM to about 150 μM, and wherein the biological fluid comprises about 5 μM or less, such as about any of 4 μM or less, 3 μM or less, 2 μM or less, or 1 μM or less of PIC, after illumination. In some embodiments, the method for treating is sufficient to inactivate at least about 1 log of a pathogen, if present (e.g., when present), such as at least about any of 2 logs, 3 logs, 4 logs, 5 logs, 6 logs, 7 logs, 8 logs, 9 logs, or 10 logs, wherein a concentration of the pathogen inactivation compound in admixture with the biological fluid prior to illuminating is about 15 μM to about 150 μM (e.g., about 30 μM to about 110 μM, about 60 μM to about 90 μM about 75 μM), wherein a total dose of ultraviolet light illuminating the biological fluid is about 0.5 J/cm$^2$ to about 50 J/cm$^2$, (e.g., about 3 J/cm$^2$ to about 15 J/cm$^2$) and wherein the biological fluid comprises about 5 μM or less, such as about any of 4 μM or less, 3 μM or less, 2 μM or less, or 1 μM or less of PIC, after illumination. In some embodiments, the method for treating is sufficient to inactivate at least about 4 log of a pathogen, if present (e.g., when present), wherein a concentration of the pathogen inactivation compound in admixture with the biological fluid prior to illuminating is about 30 μM to about 110 μM, and wherein the biological fluid comprises about 5 μM of PIC, after illumination. In some embodiments of any of the aforementioned methods, the biological fluid after illuminating is suitable for infusion into a subject without further processing to remove residual pathogen inactivation compound or photoproduct(s) thereof.

In some embodiments of any of the methods provided herein, the biological fluid comprises a blood product. In some embodiments, the biological fluid comprises a whole blood composition. In some embodiments, the biological fluid comprises a red blood cell composition. In some embodiments, the biological fluid comprises a platelet composition (e.g., platelets). In some embodiments, the biological fluid comprises a plasma composition (e.g., plasma). In some embodiments, the biological fluid comprises a platelet composition (e.g., platelets) and a plasma composition (e.g., plasma). In some embodiments, the biological fluid (e.g., platelet composition) comprises a platelet additive solution. In some embodiments, the biological fluid is a platelet composition, wherein the platelet composition comprises a platelet additive solution and plasma (e.g., about 5 to 50% plasma and about 95 to 50% additive solution; about 30 to 50% plasma and about 70% to 50% platelet additive solution). For example, in some embodiments, methods for treating comprises preparing a platelet composition suitable for infusion into an individual using the systems and methods disclosed herein.

In some embodiments of any of the methods provided herein, the method for treating described herein is sufficient to inactivate at least 1 log (e.g., at least 2 logs, 3 logs, 4 logs or more) of a pathogen (e.g., when present), wherein the biological fluid after illumination is suitable for infusion into a subject without further processing to remove residual PIC or photoproducts thereof. In some embodiments, the method for treating is sufficient to inactivate at least 1 log (e.g., at least 2 logs, 3 logs, 4 logs or more) of a pathogen (e.g., when present), wherein the platelet composition after illumination comprises 5 µM or less of PIC. In some embodiments, the concentration of PIC in the admixture prior to illumination is at least 10 µM. In some embodiments, the concentration of PIC in the admixture prior to illumination is at least 30 µM, at least 50 µM, at least 70 µM, at least 90 µM, or at least 110 µM or more. In some embodiments, the concentration of PIC in the admixture prior to illumination is between about 15 µM and about 150 µM. In some embodiments, the concentration of PIC in the admixture prior to illumination is between about 15 µM and about 110 µM, between about 30 µM and about 110 µM, between about 60 µM and about 110 µM, between about 30 µM and about 90 µM, or between about 60 µM and about 90 µM. In some embodiments, the concentration of PIC in the admixture prior to illumination is about 75 µM. In some embodiments, the methods for treating biological fluids disclosed herein do not include subjecting the biological fluid to further processing, such as exposure to a compound adsorption device (CAD), after illuminating the biological fluid for a duration and at an intensity sufficient to inactivate one or more pathogens in the biological fluid, if present. In some embodiments, the methods for treating biological fluids disclosed herein do not include subjecting the biological fluid to further processing, such as exposure to a compound adsorption device (CAD) to remove residual PIC or photoproducts thereof, after illuminating the biological fluid for a duration and at an intensity sufficient to inactivate one or more pathogens in the biological fluid, if present (e.g., when present), wherein the method is sufficient to inactivate at least 1 log of the pathogen (e.g., at least 4 logs of the pathogen), and wherein the biological fluid, after being illuminated according to the methods disclosed herein, is suitable for infusion into a subject. In some embodiments, the biological sample, after illuminating the biological sample according to the methods disclosed herein, comprises less than 5 µM of PIC (e.g., less than 2 µM of PIC).

In some embodiments of any of the methods provided herein, the method for treating comprises obtaining or pre-mixing a PIC with a platelet additive solution (PAS) at a desired (e.g., standardized) concentration and then dosing the PIC/PAS solution into a platelet preparation, thus allowing for, e.g., (i) improved processing flexibility and control, (ii) improved pathogen inactivation, including for example, allowing for reduced amounts of PIC used for pathogen inactivation, (iii) reduced processing steps, such as no requirement for further processing with a compound absorption device (CAD) to remove residual PIC or photoproducts thereof prior to administration to an individual, and/or (iv) improved platelet quality.

In some embodiments of any of the methods provided herein, the method for treating further comprises, prior to illumination: incubating the biological fluid with the photoactive pathogen inactivation compound for a period of from 30 minutes to 24 hours (e.g., 2 hours to 24 hours, 4 hours to 24 hours, 8 hours to 24 hours, 12 hours to 24 hours).

As used herein, the singular form "a", "an", and "the" includes plural references unless indicated otherwise.

It is understood that aspects and embodiments of the disclosure provided herein include "comprising," "consisting," and "consisting essentially of" aspects and embodiments.

It is understood that when a range is provided "between" two numbers, the endpoints of the range are included. For example, the range "between x and y" or "between about x and about y" includes the values x and y.

The disclosure is illustrated further by the following examples, which are not to be construed as limiting the disclosure in scope or spirit to the specific procedures described in them.

EXAMPLES

Example 1. System for Treating Biological Fluids

An exemplary system for treating biological fluids was constructed to house within a treatment chamber two opposing arrays of light sources facing each other, each comprising 72 clusters of 4 LED channels, with each cluster comprising both 340 nm and 365 nm wavelength LEDs (see e.g., FIG. 2A). The system also included a glass platform positioned between the two arrays as a means to illuminate containers of biological fluids placed on the platform with ultraviolet light from opposite sides of the containers (see e.g., FIG. 4). System controls provided for adjustment of the LEDs and treatment of the biological fluid samples with light from either the 340 nm LEDs or the 365 nm LEDs separately, or both the 340 nm and 365 nm wavelengths simultaneously or consecutively, controlling both the timing (e.g., duration) and intensity of illumination by the LEDs.

Example 2. Photochemical Conversion of a Pathogen Inactivation Compound

A study was performed to determine the efficiency of photochemical conversion of a pathogen inactivation compound using a system of the present disclosure. The photochemical agent, amotosalen (also referred to as S-59), is a psoralen pathogen inactivation compound used in a commercially available medical device for pathogen inactivation treatment of plasma and platelet blood components (INTERCEPT® Blood System, Cerus Corporation). To determine the efficiency of photochemical conversion of amotosalen and the profile of photoproducts present after treatment with the LED-based illumination device described in Example 1, studies compared multiple wavelengths and light sources. Illumination was performed with the narrow bandwidth 340 nm wavelength LEDs (Example 1 device), the narrow bandwidth 365 nm wavelength LEDs (Example 1 device) and a commercially available INTERCEPT® Blood System illumination device (INT-100), which is based on fluorescent UVA bulbs. The bulbs in the INT-100 device generate broad bandwidth illumination across the entire UVA spectrum (see e.g., FIG. 9), and a filter within the INT-100 device attenuates the light at wavelengths below 320 nm, thus resulting in UVA illumination from about 320-400 nm, with peak wavelength of approximately 352 nm, as spectral curve 902. Exemplary narrow bandwidth peaks with 340 nm and 365 nm LEDs are also depicted (not to scale) in FIG. 9 for comparison as spectral curves 904 and 906, respectively. For purposes of data described in Examples 1-9 herein using prototype systems, light doses are in Joules (J)/cm²±25%.

For the study, units of three different suspension media were prepared, including: 100% plasma, platelet additive solution (PAS III), or combined plasma+PAS III at 35%/65% ratio. Amotosalen (S-59) was added to each type of units at a concentration of 150 μM, followed by subjecting the units to illumination with approximately 6.4 J/cm² UV light dose (100% plasma), approximately 3.6 J/cm² UV light dose (PAS+plasma) or approximately 3 J/cm² UV light dose (PAS) from the LED-based device at 340 nm or 365 nm (used with all unit types), or approximately 6.4 J/cm² UV light dose from the INT-100 device (used with plasma or PAS units only). Samples taken pre- and post-illumination were analyzed by HPLC as described previously (Schlenke et al., 2008, Transfusion, 48:697-705) to determine the efficiency of S-59 photoconversion as well as the profile of photoproducts.

The percent residual S-59 after illumination is shown in the following Table 1 for the Plasma, PAS or PAS+Plasma (65/35) units. Notably, illumination of S-59 with the 340 nm wavelength LED at approximately 6.4 J/cm² resulted in significantly greater photoconversion of S-59 in each type of medium than with either the 365 nm LED or INT-100 illuminations at a similar light dosage.

TABLE 1

Photoconversion of S-59 (% of input S-59 remaining).

| | PAS 365 nm | PAS 340 nm | PAS INT100 | Plasma 365 nm | Plasma 340 nm | Plasma INT100 | 65/35 365 nm | 65/35 340 nm |
|---|---|---|---|---|---|---|---|---|
| S-59 (%) | 36.8 | 13.4 | 26.2 | 66.8 | 33.1 | 60.5 | 46.2 | 9.1 |

Additionally, HPLC analysis of post-illumination samples was used to determine area counts and relative levels for residual S-59 and photoproducts, following the various treatment conditions. As shown in the following Table 2, differences in the resulting photoproduct profiles were observed for the 340 nm, 365 nm and INT-100 illuminations.

TABLE 2

Post-illumination photoproducts.

| | PAS 365 nm | PAS 340 nm | PAS INT100 | Plasma 365 nm | Plasma 340 nm | Plasma INT100 | 65/35 365 nm | 65/35 340 nm |
|---|---|---|---|---|---|---|---|---|
| Peak B | 107 | 167 | 132 | 215 | 169 | 220 | 307 | 315 |
| Peak C | 161 | 217 | 211 | 210 | 739 | 334 | 229 | 786 |
| Peak D | 1314 | 1423 | 1377 | 146 | 133 | 153 | 438 | 385 |
| S-59 | 4118 | 1436 | 2905 | 9675 | 4957 | 8513 | 5889 | 1249 |
| Peak E | 204 | 213 | 199 | 0 | 32 | 0 | 69 | 113 |

Example 3. Inactivation of Virus

Photochemical inactivation of a virus in human donor plasma was next evaluated using an illumination device of the present disclosure. Pathogen inactivation studies were performed in plasma spiked with the rhabdovirus vesicular stomatitis virus (VSV), and subsequently treated with amotosalen and UVA light using the narrow spectrum 340 nm and 365 nm LED device or broad spectrum INT-100 device, described in Examples 1 and 2.

Pools of ABO-matched plasma were aseptically divided into three units of approximately equal volume of 500 mL, and each was inoculated with VSV. The VSV spiked plasma units were each then connected to a commercially available INTERCEPT® Blood System processing set, mixed with amotosalen at 150 μM and transferred to the illumination container. Samples were collected from each unit prior to UV illumination for determination of pre-treatment virus titers. The VSV containing plasma units were then subjected to ~6.4 Joules/cm² UVA illumination either with the INT-100 device or 340 nm or 365 nm LEDs as the light source (see e.g., Example 2). Samples were collected after illumination for post-treatment virus titer determination using plaque assays on BHK cells.

Virus titer results from pre- and post-treatment samples are shown in the following Table 3, along with the levels of virus inactivation obtained (log inactivation).

TABLE 3

Virus inactivation

| Illumination Device | Pre-treatment titer (log PFU) | Post-treatment titer (log PFU) | Log inactivation |
|---|---|---|---|
| INT-100 | 6.3 | 2.9 | 3.4 |
| 340 nm | 6.3 | 1.7 | 4.6 |
| 365 nm | 6.3 | 3.3 | 3.0 |

These data indicated surprising differences in the levels of photochemical inactivation, with a higher level of virus inactivation using amotosalen and narrow band UVA illumination from 340 nm LEDs as light sources, compared with both the narrow band UVA illumination from 365 nm LEDs and the broad band UVA illumination from the INT-100 device. The level of inactivation from the 365 nm LEDs was comparable to the inactivation from the INT-100 device.

Virus Inactivation and Photoconversion

An additional study compared the inactivation of VSV with a lower 30 μM dose of amotosalen (S-59) and UVA light, in either 220 mL or 350 mL volumes, and using the 340 nm LED or INT-100 illumination devices. Plasma was pooled into at least 1140 mL and inoculated with a stock of VSV at a 1:100 final dilution. The VSV-spiked plasma pool was then split into four units, two with a volume of 220 mL and two with a volume of 350 mL. Each unit was dosed with amotosalen at approximately 30 μM concentration and control samples were collected to determine VSV titer and amotosalen concentration pre-UVA exposure. One 220 mL unit and one 350 mL unit were subjected to ~ 3.0 J/cm² UVA using the INT100 illuminator, while the other 220 mL and 350 mL units were subjected to ~ 3.0 J/cm² UVA using the 340 nm LED illuminator. Following the photochemical treatment, samples were collected from each unit to determine VSV titer and amotosalen concentration post-UVA exposure. VSV titers ($log_{10}$) were determined using standard plaque assay and amotosalen concentrations (μM) were determined by HPLC, as shown for the average of two replicates in the following Table 3b.

TABLE 3b

Virus inactivation and amotosalen photoconversion.

| | | INT 100 | | | 340 nM | | |
|---|---|---|---|---|---|---|---|
| Volume | Pre-Txt Titer | Post-Txt Titer | Log Inact. | Post-Txt S-59 | Post-Txt Titer | Log Inact. | Post-Txt S-59 |
| 220 mL | 6.60 | 4.58 | 2.02 | 6.53 | 4.32 | 2.28 | 0.84 |
| 220 mL | 5.24 | 3.27 | 1.97 | 7.22 | 2.85 | 2.39 | 0.92 |
| 350 mL | 6.60 | 4.93 | 1.76 | 9.32 | 4.26 | 2.34 | 2.21 |
| 350 mL | 5.24 | 3.58 | 1.66 | 10.10 | 3.03 | 2.21 | 2.34 |

These data also indicated a higher level of virus inactivation using amotosalen and UVA illumination with 340 nm LEDs as light sources, compared with the broad band UVA illumination from the INT-100 device. Additionally, the level of amotosalen photoconversion using the 340 nm device was much greater than with the INT-100 device, resulting in post-photochemical treatment levels below 1 µM in the 220 mL units and approaching 2 µM in the 350 mL units.

Additional photochemical inactivation studies were performed on other viruses. Caliciviruses, such as feline calicivirus (FCV) which has been used as a model for hepatitis E virus, have previously been shown to be highly resistant to photochemical inactivation with amotosalen (S-59), with only about 1.7-2.4 log 10 reduction in titer (Irsch et al., Transfus Med Hemother, 38: 19-31 (2011)). A study was performed to evaluate the level of inactivation of FCV in platelet preparations. More specifically, two platelet units prepared in 35% plasma/65% platelet additive solution (PAS) were pooled to generate a combined volume of approximately 400 mL, containing approximately $3.8 \times 10^{11}$ platelets. The pooled platelets were inoculated with a stock of feline calicivirus (FCV) at a 1:100 final dilution. The FCV-spiked platelets were then split into ten smaller units of approximately 28.5 mL each. Nine of these units were divided into amotosalen 'dose' groups, each comprising three units within each dose group, to which amotosalen was added at one of three different concentrations: 90 PM, 30 µM, or 15 µM. Pre-illumination samples were collected for each unit. Within each dose group, the units were incubated at room temperature for 4 hr, 8 hr, or 24 hr (T=4 hr, 8 hr, 24 hr), and then subjected to illumination with about 3 J/cm² of 340 nm UVA light, using the above-described device. For the remaining unit, amotosalen was added at a concentration of 150 µM, a pre-illumination control sample removed for analysis, and the unit then subjected to illumination with 340 nm UVA light without delay (T=0), inadvertently at more than twice the light dosage of the other nine samples. Following UVA treatment, samples were collected for all units and, along with the pre-illumination controls, used to determine FCV titers (by standard plaque assay) and amotosalen concentrations (by HPLC), with data shown in the following Table 3c.

TABLE 3c

Virus inactivation and amotosalen photoconversion.

| S-59 input concentration | Time | Log Inactivation (PFU/mL) | S-59 post-UVA concentration |
|---|---|---|---|
| 150 µM | 0 hr | 2.5 | 2.1 µM |
| 90 µM | 4 hr | >5.6 | 3.8 µM |
| 90 µM | 8 hr | >5.6 | 0.9 µM |
| 90 µM | 24 hr | >5.6 | 3.3 µM |
| 30 µM | 4 hr | 4.0 | 0.8 µM |
| 30 µM | 8 hr | >5.6 | 0.9 µM |
| 30 µM | 24 hr | >5.6 | 0.8 µM |
| 15 µM | 4 hr | 2.7 | 0.6 µM |
| 15 µM | 8 hr | 4.2 | 0.6 µM |
| 15 µM | 24 hr | >5.6 | 0.6 µM |

As shown by these data, S-59 photochemical inactivation of FCV using the 340 nm LED illumination device of the present disclosure was at higher levels than reported by Irsch (ibid) for 150 µM S-59 with broad spectrum ultraviolet A light. Additionally, incubation (e.g., pre-incubation) of the FCV containing platelets with S-59 for a period of time prior to illumination with the LED device resulted in higher levels of FCV inactivation, even with lower input concentrations of the S-59 pathogen inactivation compound. In particular, pre-incubation for 4, 8 or 24 hours in the case of both 90 µM and 30 µM S-59 concentration, 8 or 24 hours in the case of 15 µM S-59 concentration, resulted in at least 4 logs of FCV inactivation with the LED device. For the 150 µM S-59 with no pre-incubation, 2.5 logs of inactivation were obtained. Greater than 5.6 log inactivation of FCV was achieved under several conditions, which reflects inactivation to below the limit of detection for the dilutions tested in the plaque assay. Additionally, HPLC analysis to determine the amount (e.g., concentration) of S-59 remaining in samples after UVA illumination and photoconversion showed that residual S-59 concentrations pathogen inactivation were reduced to less than 5 µM, and in many cases, to less than 2 µM or less than 1 µM. These data indicate that pathogen inactivation treatment conditions can be achieved based on the methods provided herein, which result in high levels of virus inactivation (e.g., >4 logs, >5.6 logs) and also efficient S-59 photoconversion with low levels of residual S-59 concentration.

One-Sided Versus Two-Sided Illumination

A follow up study was performed to evaluate pathogen inactivation using either illumination from LED arrays positioned both above and below a biological fluid container (e.g., two-sided illumination), or illumination from an LED array positioned only above the biological fluid container (e.g., one-sided illumination).

A unit of platelets was prepared in 35% plasma/65% PAS, at a volume of approximately 370 mL, containing approximately $5.2 \times 10^{11}$ platelets, and inoculated with a stock of FCV at a 1:100 final dilution. The FCV-spiked platelets were then split into ten smaller units of approximately 28.5 mL each. Nine of these units were divided into amotosalen 'dose' groups, with amotosalen added at 150 µM in two units, 30 µM in four units, and 15 µM in four units. The 30 µM and 15 µM dose group units were incubated at room temperature for 8 hr or 24 hr (T=8 hr, 24 hr), pre-illumination samples collected for each unit, and the units then subjected to illumination with about 3 J/cm² of 340 nm UVA light, using the above-described device, delivered either from a combination of both the upper and lower LED arrays, or from the upper LED array only. For the 150 µM units, pre-illumination control samples were removed for analysis and the units then subjected to illumination with 340 nm UVA light without delay (T=0), either in the top+bottom (2-sided) LED configuration or the top only (1-sided) LED configuration. Following UVA treatment, samples were collected for all units and, along with the pre-illumination controls, used to determine FCV titers by standard plaque assay and amotosalen concentrations by HPLC, with data shown in the following Table 3d.

TABLE 3d

Virus inactivation and amotosalen photoconversion.

| Time | S-59 input concentration | Log inactivation (PFU/mL) Top/Bottom | Top Only | S-59 post-UVA concentration Top/Bottom | Top Only |
|---|---|---|---|---|---|
| 0 hr | 150 μM | 3.5 | 4.6 | 7.7 μM | 10.8 μM |
| 8 hr | 30 μM | 6.3 | >6.3 | <1 μM | <1 μM |
| 8 hr | 15 μM | 3.9 | 4.1 | <1 μM | <1 μM |
| 24 hr | 30 μM | >6.3 | >6.3 | <1 μM | <1 μM |
| 24 hr | 15 μM | >6.3 | >6.3 | <1 μM | <1 μM |

As shown by these data, incubation of the FCV containing platelets with S-59 (e.g., 8 hr, 24 hr), followed by illumination with the LED device again resulted in high levels of FCV inactivation, even with lower input concentrations of the S-59 pathogen inactivation compound. Inactivation levels greater than could be achieved 150 μM S-59, were again observed. In addition, the inactivation levels were generally comparable regardless if the FCV-containing platelets were subjected to illumination with the 340 nm LEDs from both sides, or from only a single side. HPLC analysis also showed again efficient photoconversion and the ability to achieve very low levels (e.g., <1 μM) of residual S-59 after the photochemical treatment process, using either the 1-sided or 2-sided LED illumination.

Example 4: Inactivation of Bacteria

Inactivation of bacteria in human plasma by photochemical treatment was evaluated using a system of the present disclosure. Pathogen inactivation studies were performed in human donor plasma spiked with the bacteria *E. coli*, and subsequently treated with amotosalen and UVA light using the LED-based system described in Example 1 or the INT-100 device for comparison.

More specifically, a pool of approximately 3000 mL apheresis plasma (FFP) was aseptically divided into five units of approximately equal volume of 585 mL. Each unit was inoculated with an overnight culture of *E. coli* at ~ 6 log CFU/mL. The *E. coli* spiked plasma units were each then admixed with the pathogen inactivation compound amotosalen (S-59) at one of three concentrations (150 μM for two units, 15 μM for two units, 1.5 μM for one unit), in the illumination container of an INTERCEPT® Blood System processing set. Samples were collected from each unit prior to UV illumination for determination of pre-treatment bacterial titers. The remaining *E. coli* spiked plasma was then subjected to UVA illumination either with the commercially available broad band INT-100 device at ~3 J/cm² light dosage for both 150 μm and 15 μm amotosalen containing units, or the narrow band 340 nm LED light source (Example 1 device) for 150 μm, 15 μm and 1.5 μm amotosalen containing units, which were then dosed with the UVA light one time (~3 J/cm²), two times (~6 J/cm²), or three times (~9 J/cm²) as shown in the following table. Samples were collected for each treatment condition to determine post-treatment bacterial titer using standard colony forming unit assays.

Bacterial titer results pre- and post-UVA treatment are shown in the following Table 4, along with the levels of bacterial inactivation obtained (log reduction). Additionally, the efficiency of photoconversion of amotosalen (S-59) was also determined and shown as percent remaining S-59 after each indicated treatment condition. LOQ represents the limit of quantification.

TABLE 4

Bacterial inactivation and S-59 conversion

| Device | S-59 | Dosage (J/cm²) | Pre-UVA (log cfu/mL) | Post-UVA (log cfu/mL) | Log reduction | % S-59 remaining |
|---|---|---|---|---|---|---|
| INT-100 | 150 μM | ~3 | 6.4 | <−0.7 | >7.1 | 63.0 |
| 340 nm | 150 μM | ~3 | 6.3 | <−0.7 | >7.0 | 39.9 |
| INT-100 | 15 μM | ~3 | 6.2 | 2.0 | 4.2 | 40.5 |
| 340 nm | 15 μM | ~3 | 6.1 | 1.4 | 4.7 | 13.5 |
| 340 nm | 15 μM | ~6 | 6.1 | 0.5 | 5.6 | 2.5 |
| 340 nm | 15 μM | ~9 | 6.1 | 0.5 | 5.6 | <LOQ |
| 340 nm | 1.5 μM | ~3 | 6.3 | 5.0 | 1.3 | 9.0 |
| 340 nm | 1.5 μM | ~6 | 6.3 | 4.8 | 1.5 | <LOQ |
| 340 nm | 1.5 μM | ~9 | 6.3 | 4.9 | 1.4 | <LOQ |

These data suggest that somewhat higher levels of photochemical inactivation of bacteria may be achieved using amotosalen and narrow band UVA illumination as a light source, compared with the broader band INT-100 illumination. Additionally, greater than 4 logs reduction of bacteria could be achieved with both the commercially approved 150 μM concentration of amotosalen, as well as a significantly lower 15 μM concentration. Furthermore, the efficiency of S-59 photoconversion was notably improved with the LED-based illumination device in these studies, resulting in much lower levels of S-59 in the treated materials.

In another study, four plasma units were prepared from pooled plasma at either ~220 mL or ~350 mL volumes. Each unit was inoculated with an overnight culture of *E. coli* at ~ 6 log CFU/mL. The *E. coli* spiked plasma units were each then admixed with the pathogen inactivation compound amotosalen (S-59) at a concentration 15 μM in the illumination container of an INTERCEPT® Blood System processing set. Samples were collected from each unit prior to UV illumination for determination of pre-treatment bacterial titers. The remaining *E. coli* spiked plasma was then subjected to UVA illumination with ~6.4 J/cm² light dose using either a narrow bandwidth 340 nm LED device or the commercially available INT-100 device.

Bacterial titers were analyzed pre- and post-UVA treatment to determine bacterial inactivation levels, which are shown as log reduction in the following Table 5. Additionally, S-59 photoconversion was also determined by HPLC and shown as both absolute concentration and percent remaining after each indicated treatment condition.

TABLE 5

Bacterial inactivation and S-59 conversion

| | Plasma Volume | *E. coli* Log Reduction | S-59 (μM) Remaining | % S-59 Remaining |
|---|---|---|---|---|
| INT-100 | 220 mL | 5.3 | 4.0 | 26.0 |
| 340 nm | 220 mL | 6.0 | 0.5 | 3.0 |

TABLE 5-continued

Bacterial inactivation and S-59 conversion

|  | Plasma Volume | E. coli Log Reduction | S-59 (μM) Remaining | % S-59 Remaining |
|---|---|---|---|---|
| INT-100 | 350 mL | 4.4 | 5.5 | 37.0 |
| 340 nm | 350 mL | 4.6 | 1.1 | 8.0 |

Data are average of two samples (n = 2) tested

Data are average of two samples (n=2) tested

These data also suggest that somewhat higher levels of photochemical inactivation of bacteria may be achieved using S-59 and narrow band UVA illumination as a light source, compared with the broader band INT-100 illumination. Additionally, the efficiency of S-59 photoconversion was significantly improved with the LED-based illumination device, resulting in much lower levels of S-59 in the treated materials.

To confirm that the inactivation of E. coli observed above was a photochemical process requiring the pathogen inactivation compound, and not a UVA light-only mediated effect from the LED device, a control experiment was performed with 340 nm LED illumination at increasing dosages, but with no input amotosalen. For this study, a culture of E. coli was prepared and spiked into a ~585 mL unit of plasma at a titer of ~ 6 log CFU/mL. The spiked plasma was transferred to an illumination bag from an INTERCEPT® Blood System plasma processing set, and a sample was taken pre-illumination for determination of the initial control titer. The bacteria-spiked plasma then was subjected to illumination at 340 nm, with sampling for bacterial titer after each of the energy dosages indicated in the following Table 6. Pre- and post-illumination titers are shown, as well as the log reduction calculated. No inactivation of E. coli was observed at the different light 340 nm UVA light dosage levels in the absence of pathogen inactivation compound.

TABLE 6

Bacterial inactivation

| Illuminator | ~Dosage (J/cm$^2$) | Pre-UV titer (log cfu/mL) | Post-UVA titer (log cfu/mL) | Log reduction |
|---|---|---|---|---|
| 340 nm | 0 | 6.2 | NA | NA |
| 340 nm | 0.5 | NA | 6.3 | −0.1 |
| 340 nm | 0.9 | NA | 6.2 | 0.0 |
| 340 nm | 1.4 | NA | 6.2 | 0.0 |
| 340 nm | 2.8 | NA | 6.2 | 0.0 |
| 340 nm | 3.8 | NA | 6.3 | −0.1 |
| 340 nm | 4.7 | NA | 6.1 | 0.1 |

Example 5. Treatment of Platelets in Plasma and Additive Solution

Platelets collected in PAS/Plasma (65% PAS III/35% Plasma) were pooled and split into three 285 mL units for the study. Amotosalen (S-59) was added to a concentration of 150 μM, and the units were illuminated one time (~3.6 J/cm$^2$ total dose), two times (~7.2 J/cm$^2$ total dose), or three times (~10.8 J/cm$^2$ total dose) with the narrow band 340 nm LEDs or 365 nm LEDs using the device of Example 1, or with the INT-100 device. Efficiency of S-59 photoconversion, as well as photoproducts formation, was assessed post-UVA illumination by HPLC as in previous Examples. S-59 concentrations post-illumination were 32 μM, 11 μM and 5 μM for the INT-100 device (~3.6, 7.2, 10.8 J/cm$^2$, respectively), 9 μM, 2 μM and 0.98 μM (<LOQ) for the 340 nm LED (~3.6, 7.2, 10.8 J/cm$^2$, respectively), and 42 μM, 15 μM and 7 μM for the 365 nm LED (~3.6, 7.2, 10.8 J/cm$^2$, respectively). These data indicate a greater degree of S-59 photoconversion with the narrow band 340 nm LED illumination device, with residual S-59 levels at or below 2 μM after two or three illuminations (e.g., ~7.2 or 10.8 J/cm$^2$).

HPLC analysis of post-illumination samples was used to determine area counts and relative levels for photoproducts generated from the various treatment conditions. As shown in the following Tables 7-9, differences in the resulting photoproduct profiles were observed for the 340 nm, 365 nm and INT-100 illuminations, with lower photoproduct levels generally seen after illumination with the narrow band 340 nm wavelength light.

TABLE 7

INT-100 illumination photoproducts

| INT 100 | S-59 | Peak B | Peak C | Peak D | Peak E | Peak G |
|---|---|---|---|---|---|---|
| 0 | 1753 | 0 | 0 | 0 | 0 | 0 |
| 3.6 | 396 | 19 | 24 | 127 | 27 | 9 |
| 7.2 | 129 | 18 | 338 | 102 | 26 | 11 |
| 10.8 | 56 | 15 | 34 | 72 | 24 | 12 |

TABLE 8

340 nm illumination photoproducts

| 340 nm | S-59 | Peak B | Peak C | Peak D | Peak E | Peak G |
|---|---|---|---|---|---|---|
| 0 | 1826 | 0 | 0 | 0 | 0 | 0 |
| 3.6 | 106 | 4 | 29 | 93 | 28 | 5 |
| 7.2 | 24 | 2 | 27 | 33 | 25 | 5 |
| 10.8 | 11 | 3 | 23 | 13 | 22 | 5 |

TABLE 9

365 nm illumination photoproducts

| 365 nm | S-59 | Peak B | Peak C | Peak D | Peak E | Peak G |
|---|---|---|---|---|---|---|
| 0 | 1753 | 0 | 0 | 0 | 0 | 0 |
| 3.6 | 514 | 18 | 30 | 152 | 28 | 10 |
| 7.2 | 183 | 17 | 42 | 156 | 29 | 11 |
| 10.8 | 84 | 14 | 43 | 144 | 29 | 13 |

Platelets in PAS/Plasma (65% PAS III/35% Plasma) treated at 150 μM amotosalen, with illumination one time (~3.6 J/cm$^2$ total dose), two times (~7.2 J/cm$^2$ total dose), or three times (~10.8 J/cm$^2$ total dose), comparing the 340 nm LED and the broadband INT-100 device, were also analyzed for S-59 photoconversion and photoproducts post-treatment using liquid chromatography mass spectrometry. As mass spec extinction coefficients for photoproducts were assumed identical as S-59 extinction coefficients, only relative difference in concentrations (μM) between samples are compared in the following Table 9b, rather than absolute concentrations.

TABLE 9b

| | Post-illumination photoproducts | | | | | |
|---|---|---|---|---|---|---|
| | ~3.6 J/cm² | | ~7.2 J/cm² | | ~10.8 J/cm² | |
| | INT100 | 340 nm | INT100 | 340 nm | INT100 | 340 nm |
| Peak A | 1.0 | 0.1 | 0.3 | 0.0 | 0.7 | 0.2 |
| Peak B | 21.1 | 4.7 | 9.9 | 3.4 | 19.1 | 1.9 |
| Peak B1 | 1.3 | 0.1 | 0.6 | 0.2 | 1.1 | 0.3 |
| Peak C | 4.0 | 3.4 | 2.4 | 3.7 | 5.5 | 2.2 |
| Peak D | 17.6 | 13.3 | 13.8 | 7.1 | 14.2 | 3.6 |
| S-59 | 37.0 | 21.3 | 11.6 | 4.8 | 12.0 | 2.5 |
| Peak E | 12.1 | 11.4 | 10.8 | 11.1 | 11.9 | 9.2 |
| Peak G | 12.3 | 2.8 | 6.1 | 2.9 | 11.1 | 2.3 |

Additionally, various measures of platelet quality were evaluated by standard methodologies immediately after three times UVA illumination (~10.8 J/cm²), to identify potential differences among the light sources. As shown in the following Table 10, these platelet parameters remained similar among each of the illumination conditions.

TABLE 10

| | Platelet parameters after 3x illumination | | |
|---|---|---|---|
| | INT 100 | 340 nm | 365 nm |
| Platelet count | ~1.2 × 10⁶/mL | ~1.2 × 10⁶/mL | ~1.2 × 10⁶/mL |
| pH (37° C.) | 6.60 | 6.61 | 6.74 |
| Lysis (%) | 2.25 | 2.36 | 1.72 |
| ATP mmol/×10⁸ | 4.1 | 4.0 | 4.8 |
| % Residual S-59 | 3.1 | 0.5 | 4.9 |

Example 6. Treatment of Apheresis Collected Platelets in 100% Plasma or Plasma/PAS A study was performed to evaluate the photoconversion of amotosalen in platelets in 100% plasma, as well as function of the platelets over 7 days (Day 3, Day 7) following photochemical treatment with different light doses using the 340 nm device of the present disclosure. Five apheresis units of platelets in 100% plasma were pooled and split into ~285 mL units for the study. Amotosalen (S-59) was added to a concentration of 15 µM. Three of the units were illuminated with the narrow band 340 nm LED device of Example 1 at one of three different light doses by illuminating with ~3.6 J/cm² one time (1×), two times (2×, ~7.2 J/cm²), or three times (3×, ~ 10.8 J/cm²). Additional units were illuminated with the INT-100 device at ~3.6 J/cm² for comparison or maintained as an untreated control. S-59 photoconversion was assessed post-UVA illumination by HPLC as in previous Examples. S-59 concentrations post-illumination were 4.11 µM for the INT-100 device and significantly less with the 340 nm LED illumination device: 0.86 µM (<LOQ) for 1×, 0.19 µM (<LOQ) for 2×, and 0.00 µM (<LOQ) for 3× light doses, indicating a greater degree of photoconversion.

Additionally, various biochemical and/or functional measures of platelet quality were evaluated pre- and/or post-UVA illumination, as well as days 3, 5, and 7 after treatment. As shown in the following Tables 11-19, for platelet quality parameters, results were generally similar among the controls and INT-100 and 340 nm test samples, except for the 3×340 nm dosage for certain parameters.

TABLE 11

| | Platelet counts (×10³ cells/µL) | | | | |
|---|---|---|---|---|---|
| | Pre-UVA | Post-UVA | D3 | D5 | D7 |
| Control | 1425 | | 1487 | 1436 | 1453 |
| INT-100 | 1481 | 1415 | 1395 | 1400 | 1439 |
| 340 nm (1x) | 1453 | 1366 | 1391 | 1338 | 1391 |
| 340 nm (2x) | 1448 | 1301 | 1317 | 1370 | 1376 |
| 340 nm (3x) | 1452 | 1322 | 1372 | 1550 | 1474 |

TABLE 12

| | pH at 37° C. | | | | |
|---|---|---|---|---|---|
| | Pre-UVA | Post-UVA | D3 | D5 | D7 |
| Control | 6.91 | | 6.62 | 6.70 | 6.62 |
| INT-100 | 6.87 | 6.89 | 6.82 | 6.67 | 6.54 |
| 340 nm (1x) | 6.90 | 6.89 | 6.84 | 6.70 | 6.58 |
| 340 nm (2x) | 6.90 | 6.89 | 6.86 | 6.72 | 6.56 |
| 340 nm (3x) | 6.87 | 6.87 | 6.56 | 5.57 | 5.49 |

TABLE 13

| | Adenosine triphosphate (ATP; mmole/10⁸ platelets) | | | |
|---|---|---|---|---|
| | Pre-UVA | D3 | D5 | D7 |
| Control | 4.2 | 3.6 | 3.7 | 3.3 |
| INT-100 | 3.9 | 4.3 | 4.0 | 3.5 |
| 340 nm (1x) | 4.0 | 4.4 | 4.0 | 3.7 |
| 340 nm (2x) | 3.9 | 4.4 | 4.1 | 3.7 |
| 340 nm (3x) | 3.6 | 3.8 | 0.4 | -0.1 |

TABLE 14

| | pCO₂ at 37° C. (mmHg) | | | | |
|---|---|---|---|---|---|
| | Pre-UVA | Post-UVA | D3 | D5 | D7 |
| Control | 87.7 | | 59.1 | 27.1 | 29.1 |
| INT-100 | 101.1 | 91.4 | 55.8 | 36.4 | 35.0 |
| 340 nm (1x) | 89.6 | 91.9 | 54.4 | 35.7 | 34.3 |
| 340 nm (2x) | 88.5 | 94.1 | 54.5 | 37.5 | 36.4 |
| 340 nm (3x) | 98.2 | 98.1 | 62.5 | 13.9 | 4.4 |

TABLE 15

| | pO₂ at 37° C. (mmHg) | | | | |
|---|---|---|---|---|---|
| | Pre-UVA | Post-UVA | D3 | D5 | D7 |
| Control | 35.0 | | 15.3 | 37.3 | 37.6 |
| INT-100 | 98.4 | 36.4 | 18.9 | 20.1 | 19.7 |
| 340 nm (1x) | 41.8 | 14.3 | 11.8 | 22.5 | 16.6 |
| 340 nm (2x) | 45.9 | 14.2 | 14.8 | 15.3 | 14.1 |
| 340 nm (3x) | 90.9 | 19.7 | 27.7 | 159.5 | 178.6 |

TABLE 16

| | Lactate (mmol/L) | | | |
|---|---|---|---|---|
| | Post-UVA | D3 | D5 | D7 |
| Control | 8.76 | 19.37 | 21.31 | 22.27 |
| INT-100 | 8.85 | 14.71 | 20.18 | 23.31 |

TABLE 16-continued

Lactate (mmol/L)

|  | Post-UVA | D3 | D5 | D7 |
|---|---|---|---|---|
| 340 nm (1x) | 9.05 | 15.17 | 19.81 | 21.83 |
| 340 nm (2x) | 8.77 | 14.55 | 19.06 | 22.13 |
| 340 nm (3x) | 9.48 | 20.42 | 36.09 | 36.36 |

TABLE 17

Glucose (mmol/L)

|  | Post-UVA | D3 | D5 | D7 |
|---|---|---|---|---|
| Control | 16.96 | 11.48 | 9.59 | 8.22 |
| INT-100 | 17.24 | 13.11 | 10.26 | 8.19 |
| 340 nm (1x) | 17.45 | 13.49 | 10.27 | 8.32 |
| 340 nm (2x) | 16.98 | 13.63 | 10.69 | 8.34 |
| 340 nm (3x) | 16.77 | 10.87 | 1.33 | 0.43 |

TABLE 18

Platelet lysis (%)

|  | Pre-UVA | Post-UVA | D3 | D5 | D7 |
|---|---|---|---|---|---|
| Control | 4.30 |  | 5.01 | 6.73 | 5.63 |
| INT-100 | 4.30 | 4.74 | 4.69 | 4.50 | 5.18 |
| 340 nm (1x) | 4.30 | 4.48 | 4.90 | 4.43 | 5.23 |
| 340 nm (2x) | 4.30 | 4.50 | 4.59 | 4.92 | 5.19 |
| 340 nm (3x) | 4.30 | 4.77 | 4.78 | 6.62 | 16.6 |

TABLE 19

LDH (LDH IU/$10^{11}$ platelets)

|  | Pre-UVA | Post-UVA | D3 | D5 | D7 |
|---|---|---|---|---|---|
| Control | 10.7 |  | 12.0 | 17.1 | 17.1 |
| INT-100 | 10.3 | 11.5 | 11.9 | 11.6 | 12.6 |
| 340 nm (1x) | 10.5 | 11.3 | 12.1 | 12.1 | 13.1 |
| 340 nm (2x) | 10.5 | 12.1 | 12.1 | 13.0 | 13.2 |
| 340 nm (3x) | 10.5 | 12.1 | 11.6 | 16.0 | 33.7 |

Treatment of Platelets at Different Amotosalen Concentrations

A study was performed to evaluate the photoconversion of amotosalen in platelets in 10000 plasma, as well as function of the platelets over 7 days (Day 3, Day 7) following photochemical treatment using the 340 nm device of the present disclosure. Multiple donor platelet units in 10000 plasma (5 units, ~278-391 mL) were pooled and split into 5 units of ~285 mL each, to be used as an untreated control, or treated with amotosalen at different concentrations, with ultraviolet A illumination using the 340 nm device. Amotosalen was added to a concentration of 30, 60, 90 or 110 µM, then pre-illumination (pre-UV) samples were removed for analysis, and the remainder of the units subjected to illumination at ~7.2 J/cm². Post-illumination (Post-UV) samples were then removed for post-treatment analysis. Parameters shown in the following Tables 20-29 (left side columns) for untreated control and amotosalen/UVA treated units were measured using standard analytical methods known in the art, and additionally residual amotosalen concentration was determined by HPLC analysis.

A similar study was performed to evaluate the photoconversion of amotosalen in platelets in platelet additive solution (35% plasma/65% PAS III), as well as function of the platelets over 7 days (Day 4, Day 7) following photochemical treatment using the 340 nm device of the present disclosure. Multiple donor platelet units in plasma/PAS (6 units, ~202-318 mL) were pooled and split into 5 units of ~285 mL each, to be used as an untreated control, or treated with amotosalen at different concentrations, with ultraviolet A illumination using the 340 nm device. Amotosalen was added to a concentration of 30, 60, 90 or 110 µM, then pre-illumination (pre-UV) samples were removed for analysis, and the remainder of the units subjected to illumination at ~7.2 J/cm². Post-illumination (Post-UV) samples were then removed for post-treatment analysis. Parameters shown in the following Tables 20-29 (right side columns) for untreated control and amotosalen/UVA treated units were also measured using standard analytical methods known in the art, and additionally residual amotosalen concentration was determined by HPLC analysis.

TABLE 20

Platelet counts (x$10^3$ cells/µL)

|  | Plasma | | | | PAS/Plasma | | | |
|---|---|---|---|---|---|---|---|---|
|  | Pre-UV | Post-UV | D3 | D7 | Pre-UV | Post-UV | D4 | D7 |
| Control | 1225 | N/A | 1132 | 1162 | 1389 | N/A | 1360 | 1317 |
| 30 µM | 1200 | 1115 | 1155 | 1155 | 1346 | 1308 | 1385 | 1392 |
| 60 µM | 1160 | 1117 | 1152 | 1041 | 1344 | 1249 | 1379 | 1403 |
| 90 µM | 1165 | 1115 | 1157 | 1199 | 1344 | 1313 | 1373 | 1384 |
| 110 µM | 1209 | 1239 | 1103 | 1153 | 1308 | 1335 | 0 | 0 |

TABLE 21 pH at 37° C.

|  | Plasma | | | | PAS/Plasma | | | |
|---|---|---|---|---|---|---|---|---|
|  | Pre-UV | Post-UV | D3 | D7 | Pre-UV | Post-UV | D4 | D7 |
| Control | 7.14 | N/A | 7.22 | 7.18 | 6.86 | N/A | 6.93 | 6.95 |
| 30 µM | 7.14 | 7.15 | 7.21 | 7.10 | 6.85 | 6.84 | 6.88 | 6.86 |
| 60 µM | 7.14 | 7.15 | 7.20 | 7.09 | 6.85 | 6.83 | 6.88 | 6.86 |
| 90 µM | 7.14 | 7.15 | 7.17 | 7.00 | 6.84 | 6.83 | 6.87 | 6.87 |
| 110 µM | 7.13 | 7.14 | 7.18 | 7.01 | 6.84 | 6.83 | N/A | N/A |

TABLE 22 pH at 22° C.

|  | Plasma | | | | PAS/Plasma | | | |
|---|---|---|---|---|---|---|---|---|
|  | Pre-UV | Post-UV | D3 | D7 | Pre-UV | Post-UV | D4 | D7 |
| Control | 7.36 | N/A | 7.44 | 7.40 | 7.08 | N/A | 7.15 | 7.18 |
| 30 µM | 7.36 | 7.37 | 7.43 | 7.32 | 7.07 | 7.07 | 7.11 | 7.08 |
| 60 µM | 7.36 | 7.37 | 7.43 | 7.32 | 7.08 | 7.06 | 7.11 | 7.08 |
| 90 µM | 7.37 | 7.37 | 7.39 | 7.23 | 7.06 | 7.06 | 7.10 | 7.10 |
| 110 µM | 7.36 | 7.37 | 7.40 | 7.24 | 7.07 | 7.05 | N/A | N/A |

TABLE 23

$pCO_2$ at 37° C. (mm Hg)

| | Plasma | | | | PAS/Plasma | | | |
|---|---|---|---|---|---|---|---|---|
| | Pre-UV | Post-UV | D3 | D7 | Pre-UV | Post-UV | D4 | D7 |
| Control | 53.1 | N/A | 39.1 | 31.8 | 34.4 | N/A | 28.3 | 25.2 |
| 30 μM | 52.4 | 50.2 | 38.1 | 31.2 | 35.0 | 34.9 | 26.7 | 23.6 |
| 60 μM | 52.4 | 49.2 | 38.1 | 31.2 | 33.7 | 35.1 | 26.6 | 23.1 |
| 90 μM | 50.8 | 48.5 | 40.3 | 33.5 | 34.9 | 33.7 | 26.9 | 22.6 |
| 110 μM | 51.8 | 48.1 | 38.6 | 31.7 | 33.7 | 34.2 | N/A | N/A |

TABLE 24

$pO_2$ at 37° C. (mm Hg)

| | Plasma | | | | PAS/Plasma | | | |
|---|---|---|---|---|---|---|---|---|
| | Pre-UV | Post-UV | D3 | D7 | Pre-UV | Post-UV | D4 | D7 |
| Control | 41.2 | N/A | 47.7 | 56.9 | 38.6 | N/A | 20.3 | 43.8 |
| 30 μM | 28.6 | 13.9 | 74.6 | 78.5 | 4.8 | 11.6 | 28.9 | 57.3 |
| 60 μM | 32.7 | 20.4 | 65.8 | 78.0 | 29.4 | 8.0 | 28.8 | 61.0 |
| 90 μM | 54.6 | 24.1 | 82.2 | 87.9 | 9.0 | 29.3 | 25.7 | 61.8 |
| 110 μM | 88.6 | 189.7 | 69.9 | 90.5 | 6.3 | 16.1 | N/A | N/A |

TABLE 25

Lactate (mmol/L)

| | Plasma | | | | PAS/Plasma | | | |
|---|---|---|---|---|---|---|---|---|
| | Pre-UV | Post-UV | D3 | D7 | Pre-UV | Post-UV | D4 | D7 |
| Control | 5.7 | N/A | 6.6 | 9.7 | 7.05 | N/A | 9.97 | 14.01 |
| 30 μM | 5.4 | 5.7 | 6.9 | 12.1 | 8.6 | 8.21 | 7.1 | 15.38 |
| 60 μM | 5.4 | 5.6 | 6.8 | 11.8 | 6.72 | 6.93 | 10.11 | 15.16 |
| 90 μM | 5.3 | 5.7 | 7.3 | 13.6 | 6.95 | 7.11 | 9.83 | 14.62 |
| 110 μM | 5.3 | 5.4 | 7.3 | 13.8 | 6.85 | 7.18 | N/A | N/A |

TABLE 26

Glucose (mmol/L)

| | Plasma | | | | PAS/Plasma | | | |
|---|---|---|---|---|---|---|---|---|
| | Pre-UV | Post-UV | D3 | D7 | Pre-UV | Post-UV | D4 | D7 |
| Control | 16.3 | N/A | 15.6 | 13.3 | 2.4 | N/A | 2.19 | 0.08 |
| 30 μM | 16.0 | 15.9 | 14.9 | 11.9 | 5.2 | 5.45 | 3.27 | 0.16 |
| 60 μM | 16.2 | 15.9 | 15.0 | 11.6 | 5.16 | 5.04 | 2.92 | 0 |
| 90 μM | 15.9 | 15.9 | 14.9 | 10.6 | 4.9 | 4.95 | 2.97 | 0 |
| 110 μM | 15.9 | 16.0 | 14.7 | 10.4 | 4.95 | 4.88 | N/A | N/A |

TABLE 27

Platelet lysis (%)

| | Plasma | | | | PAS/Plasma | | | |
|---|---|---|---|---|---|---|---|---|
| | Pre-UV | Post-UV | D3 | D7 | Pre-UV | Post-UV | D4 | D7 |
| Control | 5.09 | N/A | 5.15 | 5.49 | 1.88 | N/A | 2.65 | 3.06 |
| 30 μM | 4.92 | 5.31 | 5.22 | 6.10 | 2.46 | 2.85 | 2.86 | 3.17 |
| 60 μM | 4.71 | 5.10 | 5.15 | 11.82 | 2.68 | 2.65 | 3.10 | 3.37 |
| 90 μM | 4.97 | 5.13 | 4.88 | 5.42 | 2.76 | 2.64 | 3.23 | 3.53 |
| 110 μM | 4.61 | 4.63 | 5.90 | 6.13 | 2.65 | 2.72 | N/A | N/A |

TABLE 28

LDH (LDH IU/$10^{11}$ platelets)

| | Plasma | | | | PAS/Plasma | | | |
|---|---|---|---|---|---|---|---|---|
| | Pre-UV | Post-UV | D3 | D7 | Pre-UV | Post-UV | D4 | D7 |
| Control | 13.8 | N/A | 15.3 | 16.2 | 5.11 | N/A | 7.28 | 8.58 |
| 30 μM | 13.7 | 15.0 | 14.5 | 17.4 | 7.13 | 7.80 | 7.44 | 8.26 |
| 60 μM | 13.6 | 14.3 | 13.9 | 36.5 | 7.66 | 7.53 | 8.12 | 8.48 |
| 90 μM | 13.8 | 13.9 | 13.1 | 13.9 | 7.59 | 7.01 | 7.94 | 8.67 |
| 110 μM | 12.4 | 12.0 | 17.0 | 16.0 | 7.42 | 6.97 | N/A | N/A |

TABLE 29

Amotosalen concentration (μM)

| | Plasma | | PAS/Plasma | |
|---|---|---|---|---|
| | Pre-UV | Post-UV | Pre-UV | Post-UV |
| 30 μM | 32.7 | 1.1 | 30.5 | 0.3 |
| 60 μM | 62.0 | 2.3 | 61.2 | 0.7 |
| 90 μM | 89.7 | 4.0 | 90.5 | 1.0 |
| 110 μM | 105.8 | 5.5 | 120.7 | 1.2 |

These data show that quality of platelets in either 100% plasma or plasma+PAS is suitably maintained across a range of amotosalen treatment concentrations (e.g., 30 μM to 110 μM) compared to untreated control platelets, and additionally post-treatment levels of amotosalen can be reduced to <5 μM (including <1 μM) following illumination with the 340 nm device.

Additional studies further evaluated the quality of platelets after pathogen inactivation under conditions to achieve <2 μM post-treatment residual amotosalen, using illumination with either the 340 nm LED system or the commercially available INTERCEPT Blood System with INT-100 system. Platelet units in 100% plasma were pooled to 750-900 mL and then split into multiple 250-300 mL units for treatment comprising each of three conditions: 1) 75 μM input concentration of amotosalen illuminated with the 340 nm device at ~6.4; 2) 75 μM input amotosalen illuminated with the 340 nm device at ~7.2 J/cm$^2$; 3) 150 μM input amotosalen illuminated with the INT-100 device at ~3.6 J/cm$^2$ (e.g., standard conditions for this system). Post-treatment INT-100 illuminated units were necessarily subjected to CAD processing to reduce residual amotosalen, while CAD was not needed for the 340 nm illuminated units.

Parameters shown in the following Tables 30-34 were measured using standard analytical and other assay methods known in the art, including $pCO_2$ and $pO_2$ (blood gas analyzer), morphology (Kunicki score), P-selectin (flow cytometry), Extent of Shape Change (aggregometer), Hypotonic Shock Response (aggregometer), and residual amotosalen concentration was determined by HPLC analysis.

TABLE 30 pH

| Treatment | | Pre-UVA | Post-UVA | D5 | D7 |
|---|---|---|---|---|---|
| pH @ 37° C. | INT-100 | 7.08 | 6.94 | 6.93 | 6.74 |
| | 340/~6.4 | 7.06 | 7.07 | 6.92 | 6.72 |
| | 340/~7.2 | 7.08 | 7.09 | 6.88 | 6.72 |
| pH @ 22° C. | INT-100 | 7.31 | 7.17 | 7.16 | 6.96 |
| | 340/~6.4 | 7.29 | 7.30 | 7.15 | 6.95 |
| | 340/~7.2 | 7.31 | 7.32 | 7.11 | 6.94 |

TABLE 31

$pCO_2$ and $pO_2$ (mmHg)

| | Treatment | Pre-UVA | Post-UVA | D5 | D7 |
|---|---|---|---|---|---|
| $pCO_2$ | INT-100 | 54.43 | 54.60 | 31.83 | 28.47 |
| | 340/~6.4 | 55.20 | 43.60 | 35.00 | 30.95 |
| | 340/~7.2 | 54.43 | 47.23 | 37.47 | 32.70 |
| $pO_2$ | INT-100 | 31.77 | 62.87 | 69.77 | 70.37 |
| | 340/~6.4 | 37.60 | 42.90 | 59.75 | 61.80 |
| | 340/~7.2 | 31.77 | 32.93 | 49.33 | 56.07 |

TABLE 32

P-selectin (CD62P) and Extent of Shape Change (ESC)

| | Treatment | Pre-UVA | Post-UVA | D5 | D7 |
|---|---|---|---|---|---|
| CD62 | INT-100 | 27.77 | N/A | 39.07 | 58.77 |
| | 340/~6.4 | 31.95 | N/A | 51.70 | 67.65 |
| | 340/~7.2 | 27.77 | N/A | 45.00 | 56.93 |
| ESC | INT-100 | 23.50 | N/A | 25.20 | 19.82 |
| | 340/~6.4 | 20.60 | N/A | 22.15 | 16.45 |
| | 340/~7.2 | 23.50 | N/A | 26.73 | 19.47 |

TABLE 33

Hypotonic Shock Response (HSR) and Morphology

| | Treatment | Pre-UVA | Post-UVA | D5 | D7 |
|---|---|---|---|---|---|
| HSR | INT-100 | 49.67 | N/A | 55.10 | 46.00 |
| | 340/~6.4 | 45.40 | N/A | 56.50 | 45.98 |
| | 340/~7.2 | 49.67 | N/A | 51.87 | 49.47 |
| Morphology | INT-100 | 279.33 | N/A | 265.67 | 274.67 |
| | 340/~6.4 | 265.50 | N/A | 271.50 | 259.00 |
| | 340/~7.2 | 279.33 | N/A | 287.67 | 254.67 |

TABLE 34

Amotosalen concentration

| | Treatment | Pre-UVA | Post-UVA | % Residual | Post-CAD |
|---|---|---|---|---|---|
| S-59 (μM) | INT-100 | 173.2 | 69.4 | 40.1 | 0.2 |
| | 340/~6.4 | 93.3 | 2.4 | 2.5 | N/A |
| | 340/~7.2 | 94.0 | 1.9 | 2.0 | N/A |

These data show that quality of platelets is suitably maintained at both amotosalen treatment conditions with 340 nm illumination, and that post-treatment residual levels of amotosalen were reduced to ~ 2 μM, without the use of any further processing to remove residual amotosalen.

Example 7. Treatment of Plasma

A study was performed to evaluate the photoconversion of amotosalen in whole-blood derived plasma, as well as properties of the plasma after photochemical treatment using either the broadband UVA device (INT-100) or the 340 nm device of the present disclosure. Multiple donor plasma units (3-4 units, ~250-350 mL each) were pooled and split into three units of ~ 285 mL each, to be used as untreated control, or amotosalen treated with illumination using either the INT-100 or 340 nm devices. This pool and split format was repeated four times to generate four replicates. Amotosalen was added to a concentration of 50 μM, pre-illumination (pre-UVA) samples were removed for analysis, and the remainder of the unit subjected to illumination at ~6.4 J/cm². Post-illumination (Post-UVA) samples were then removed for post-treatment analysis. Parameters in the following Table 35 were measured using standard analytical methods known in the art, and additionally residual amotosalen concentration was determined by HPLC analysis as 17.06 μM using the INT-100 device and 4.65 μM using the 340 nm device.

TABLE 35

Plasma parameters pre- and post-illumination

| | | INT-100 | | 340 nm | |
|---|---|---|---|---|---|
| | Control | Pre-UVA | Post-UVA | Pre-UVA | Post-UVA |
| pH @ 37° C. | 7.20 | 7.22 | 7.24 | 7.19 | 7.20 |
| $pCO_2$ @ 37° C. (mmHg) | 69.38 | 69.20 | 60.68 | 67.38 | 66.75 |
| $pO_2$ @ 37° C. (mmHg) | 139.18 | 141.95 | 41.55 | 131.80 | 42.88 |
| Total Protein (mg/mL) | 66.83 | 80.18 | 70.35 | 72.13 | 72.43 |
| PT (sec) | 11.95 | 11.48 | 12.28 | 11.68 | 12.03 |
| aPTT (sec) | 1 | 30.35 | 33.98 | 31.15 | 33.95 |
| Fibrinogen (mg/dL) | 301.25 | 278.75 | 261.50 | 290.00 | 259.75 |
| Factor II (IU/dL) | 94.13 | 91.45 | 110.93 | 93.43 | 84.00 |
| Factor V (IU/dL) | 101.73 | 98.55 | 90.25 | 97.08 | 88.83 |
| Factor VIII (IU/dL) | 139.50 | 154.25 | 108.85 | 165.50 | 127.18 |
| Factor X (IU/dL) | 89.93 | 92.40 | 84.53 | 96.68 | 84.68 |
| Factor XI (IU/dL) | 79.90 | 89.55 | 76.63 | 85.65 | 73.93 |
| Protein C (IU/dL) | 118.88 | 98.55 | 109.30 | 133.90 | 122.33 |
| Protein S (IU/dL) | 102.63 | 111.88 | 121.80 | 119.00 | 118.03 |

These data show that plasma quality after photochemical treatment is suitably maintained as compared to untreated control plasma, and additionally post-treatment levels of amotosalen were reduced to <5 μM following illumination with the 340 nm device, but not with the INT-100 device.

Example 8. System for Treating Biological Fluids

Another exemplary system for treating biological fluids was constructed to provide within the device, a treatment chamber with interchangeable arrays of light sources, with each array having LED channels of narrow bandwidth single peak wavelengths (e.g., first peak wavelength) of 265 nm, 280 nm, 310 nm, 325 nm, 340 nm, 365 nm or 385 nm in the UVA, UVB, or UVC spectrum. This system comprised single arrays facing (e.g., opposing) a platform positioned for the illumination of biological fluids placed on the platform (see e.g., FIG. 5). System controls provided for adjustment of the LEDs during treatment of the biological fluid samples, controlling both the timing and intensity of illumination by the LEDs to achieve a desired light UV light dose. Evaluation of photochemical conversion, photoproduct formation, pathogen inactivation, and plasma and/or platelet quality parameters are performed for each light source wavelength as described previously.

In one study using the device, photochemical inactivation of various bacteria were tested for each of the above-referenced LEDs together with amotosalen. The bacteria included *E. coli* (Gram negative), *S. epidermidis* (Gram positive), and *P. acnes* (anaerobe). As there are known germicidal effects of ultraviolet light with wavelengths in the UVC and UVB range, the study was controlled to determine for each LED wavelength the total inactivation levels, as well as inactivation levels specifically resulting from the UV light (without added amotosalen) or the photochemical treatment process itself.

Bacterial cultures were inoculated at ~ 6 log CFU/mL into plasma units, from which a sample was taken for initial bacterial titer using a standard colony forming unit assay, followed by dividing of the spiked plasma into one of three control or treatment units. Amotosalen treatment arms included 15 μM concentrations for each of the three bacteria, as well as an additional 150 μM concentration treatment arm for *E. coli*.

Plasma+bacteria, no illumination
Plasma+bacteria, with illumination
Plasma+bacteria+amotosalen, with illumination Samples were taken and pre-illumination bacterial titers determined for each spiked unit, and the units aliquoted into six-well plates (2 mL/well) for illumination. The plates were subjected to illumination at 265 nm, 280 nm, 310 nm, 325 nm, 340 nm, 365 nm or 385 nm with ~3 J/cm² light dose for *E. coli* and *S. epidermidis*, and ~ 6.4 J/cm² for *P. acnes*, followed by post-illumination bacterial titer determination using standard colony forming unit assay. The following Tables 36-39 show total log reduction of the bacteria, as well as log reduction attributable to photochemical inactivation with amotosalen (S-59) or attributable to only the UV light (without amotosalen). HPLC analysis also was used to determine residual post-illumination amotosalen concentrations in the samples as described previously.

TABLE 36

Amotosalen and UV light treatment of *E. coli* (150 μM)

| Wavelength | Log reduction total | Log reduction from S-59 | Log reduction from light | Pre-UV S-59 (μM) | Post-UV S-59 (μM) |
|---|---|---|---|---|---|
| 265 nm | 5.01 | 0.54 | 4.81 | 148.9 | 115.0 |
| 280 nm | 5.38 | 0.59 | 5.14 | 152.7 | 148.1 |
| 310 nm | 6.23 | 2.29 | 4.12 | 151.1 | 56.8 |
| 325 nm | 5.70 | 5.36 | 0.53 | 141.6 | 52.1 |
| 340 nm | 5.64 | 4.93 | 0.50 | 142.2 | 48.1 |
| 365 nm | 5.30 | 4.90 | −0.38 | 153.2 | 79.8 |
| 385 nm | 4.95 | 4.34 | 0.54 | 148.4 | 135.1 |

TABLE 37

Amotosalen and UV light treatment of *E. coli* (15 μM)

| Wavelength | Log reduction total | Log reduction from S-59 | Log reduction from light | Pre-UV S-59 (μM) | Post-UV S-59 (μM) |
|---|---|---|---|---|---|
| 265 nm | 4.52 | 0 | 4.52 | 16.0 | 12.7 |
| 280 nm | 4.52 | 0 | 4.52 | 16.2 | 12.6 |
| 310 nm | 4.52 | 1.15 | 3.37 | 15.4 | 5.5 |
| 325 nm | 4.52 | 3.81 | 0.71 | 15.8 | 4.0 |
| 340 nm | 4.52 | 2.94 | 1.58 | 16.0 | 3.7 |
| 365 nm | 4.52 | 2.76 | 1.76 | 16.2 | 8.1 |
| 385 nm | 1.5 | 0.49 | 1.75 | 15.3 | 14.3 |

TABLE 38

Amotosalen and UV light treatment of *S. epidermidis* (15 μM)

| Wavelength | Log reduction total | Log reduction from S-59 | Log reduction from light | Pre-UV S-59 (μM) | Post-UV S-59 (μM) |
|---|---|---|---|---|---|
| 265 nm | 5.23 | 0.89 | 4.35 | 14.4 | 13.0 |
| 280 nm | 5.02 | 1.56 | 3.51 | 14.8 | 11.8 |
| 310 nm | 7.19 | 6.68 | 0.55 | 14.3 | 5.2 |
| 325 nm | 7.18 | 7.17 | 0.14 | 14.9 | 3.7 |
| 340 nm | 7.28 | 7.18 | 0.16 | 14.8 | 3.6 |
| 365 nm | 7.26 | 7.32 | 0.05 | 14.8 | 7.8 |
| 385 nm | 1.76 | 1.85 | 0.07 | 15.0 | 15.1 |

TABLE 39

Amotosalen and UV light treatment of *P. acnes* (15 μM)

| Wavelength | Log reduction total | Log reduction from S-59 | Log reduction from light | Pre-UV S-59 (μM) | Post-UV S-59 (μM) |
|---|---|---|---|---|---|
| 265 nm | 6.03 | 1.60 | 4.43 | 15.7 | 10.8 |
| 280 nm | 1.09 | 0.71 | 0.38 | 15.7 | 16.0 |
| 310 nm | 6.99 | 5.67 | 1.32 | 15.7 | 2.2 |
| 325 nm | 6.69 | 6.54 | 0.15 | 15.7 | 1.1 |
| 340 nm | 6.99 | 6.78 | 0.21 | 15.7 | 1.4 |
| 365 nm | 6.99 | 6.67 | 0.32 | 15.7 | 5.5 |
| 385 nm | 1.97 | 1.64 | 0.33 | 15.7 | 13.7 |

High level bacterial inactivation was observed. When comparing the effect of amotosalen+UV light versus UV light only (without amotosalen), the data indicate that photochemical inactivation (amotosalen+UV light) is generally highest for all three bacteria in UVA treatment arms of 325 nm, 340 nm and 365 nm. Photochemical inactivation in the amotosalen+UVB wavelength treatment arm of 310 nm appears more variable and to a lower level than for amotosalen+325 nm, 340 nm or 365 nm UVA light, with an increasing direct germicidal effect observed from the UVB light compared to the UVA light. The amotosalen+UVC treatment arms of 265 nm and 280 nm provided minimal inactivation attributable to the amotosalen, with the inactivation primarily from direct germicidal effects of the UVC light. When also taking into account post-treatment (post-UVA) analysis of residual amotosalen levels, these data show that greater than 4 logs of photochemical inactivation could be achieved with less than 5 μM residual amotosalen in both the amotosalen+325 nm illumination and amotosalen+340 nm illumination treatment conditions.

Example 9. Pathogen Inactivation with Multiple Wavelength Combinations

Additionally, any two or more wavelengths of narrow bandwidth light are evaluated in combination, such as for example, photochemical treatment of a biological fluid using amotosalen and ultraviolet light of a first peak wavelength and ultraviolet light of a second peak wavelength, sequentially or concurrently. More specifically, in one example pathogen inactivation of *E. coli* (Gram negative) and *S. epidermidis* (Gram positive) bacteria was evaluated using amotosalen and the device with LEDs of wavelengths described in Example 8. Bacterial cultures were inoculated at ~ 6 log CFU/mL into plasma units, from which a sample was taken for initial bacterial titer using standard colony forming unit assay. The spiked plasma units were divided into control (no amotosalen+UV light) and treatment (with amotosalen) conditions, with amotosalen used at 15 µM concentration. The units were aliquoted into six-well plates (5 mL/well) for illumination. Pre-illumination samples were taken and control bacterial titers determined using standard colony forming unit assay. The plates were subjected to two sequential light doses of ~3 J/cm² each, using combinations of a 265 nm or 280 nm UVC light dose together with a 325 nm, 340 nm or 365 nm UVA light dose, followed by post-illumination bacterial titer determination, and analysis of residual amotosalen. Data for pre-illumination titers, post-first illumination titer, post-second illumination titer, and post-treatment (after second illumination) residual amotosalen (S-59) are shown in the following Tables 40-41.

TABLE 40

Amotosalen and UV light treatment of E. coli

| UV 1 | UV 2 | Titer Pre-UV | Titer Post-First | Titer Post-Second | S-59 (µM) |
|---|---|---|---|---|---|
| 265 nm | 325 nm | 6.57 | 3.58 | <-0.11 | 4.76 |
| 265 nm | 340 nm | 6.57 | 3.86 | <-0.11 | 3.89 |
| 265 nm | 365 nm | 6.57 | 2.95 | <-0.11 | 8.07 |
| 280 nm | 325 nm | 6.57 | 3.66 | <-0.11 | 4.44 |
| 280 nm | 340 nm | 6.57 | 4.15 | <-0.11 | 3.62 |
| 280 nm | 365 nm | 6.57 | 4.11 | <-0.11 | 7.96 |
| 325 nm | 265 nm | 6.57 | <-0.11 | <-0.11 | 4.88 |
| 325 nm | 280 nm | 6.57 | <-0.11 | <-0.11 | 4.66 |
| 340 nm | 265 nm | 6.57 | <-0.11 | <-0.11 | 4.43 |
| 340 nm | 280 nm | 6.57 | <-0.11 | <-0.11 | 4.46 |
| 365 nm | 265 nm | 6.57 | <-0.11 | <-0.11 | 8.13 |
| 365 nm | 280 nm | 6.57 | <-0.11 | <-0.11 | 8.00 |

TABLE 41

Amotosalen and UV light treatment of S. epidermidis

| Light 1 | Light 2 | Titer Pre-UV | Titer Post-First | Titer Post-Second | S-59 (µM) |
|---|---|---|---|---|---|
| 265 nm | 325 nm | 7.51 | 4.19 | <-0.11 | 4.82 |
| 265 nm | 340 nm | 7.51 | 4.37 | <-0.11 | 3.93 |
| 265 nm | 365 nm | 7.51 | 4.12 | <-0.11 | 8.17 |
| 280 nm | 325 nm | 7.51 | 4.13 | <-0.11 | 4.50 |
| 280 nm | 340 nm | 7.51 | 4.51 | <-0.11 | 3.77 |
| 280 nm | 365 nm | 7.51 | 4.19 | <-0.11 | 8.01 |
| 325 nm | 265 nm | 7.51 | <-0.11 | <-0.11 | 4.92 |
| 325 nm | 280 nm | 7.51 | <-0.11 | <-0.11 | 4.63 |
| 340 nm | 265 nm | 7.51 | <-0.11 | <-0.11 | 4.47 |
| 340 nm | 280 nm | 7.51 | 0.73 | <-0.11 | 4.46 |
| 365 nm | 265 nm | 7.51 | <-0.11 | <-0.11 | 8.39 |
| 365 nm | 280 nm | 7.51 | <-0.11 | <-0.11 | 8.07 |

High level bacterial inactivation was observed. Similar pathogen inactivation studies are performed using other bacteria identified as less sensitive to amotosalen/UV and/or UVC treatment. Additionally, similar studies are performed with other combinations of sequential light doses, including using combinations of a 310 nm UVB light dose together with a 325 nm, 340 nm or 365 nm UVA light dose (either order), as well as combinations of a 325 nm, 340 nm or 365 nm UVA light dose, followed by another different 325 nm, 340 nm or 365 nm UVA light dose (either order). In addition, using these or other devices of the present disclosure, similar studies may evaluate any of the above wavelength combinations with concurrent illumination, rather than sequential illumination, and/or using different containers (e.g., blood product bags).

While specific components, configurations, features, and functions are provided above, it will be appreciated by one of ordinary skill in the art that other variations may be used. Additionally, although a feature may appear to be described in connection with a particular embodiment, one skilled in the art would recognize that various features of the described embodiments may be combined. Moreover, aspects described in connection with an embodiment may stand alone.

Although embodiments have been fully described with reference to the accompanying drawings, it should be noted that various changes and modifications will be apparent to those skilled in the art. Such changes and modifications are to be understood as being included within the scope of the various embodiments as defined by the appended claims.

Variations of the embodiments provided herein may become apparent to those working in the art upon reading the foregoing description. It is expected that skilled artisans will be able to employ such variations as appropriate, and the practice of the compositions, methods, and kits described herein otherwise than as specifically described herein. Accordingly, the systems and methods described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context. The following is a list of particular embodiments of the present disclosure. The list is exemplary is it not intended to be limiting of the disclosure provided herein.

Embodiment 1. A system for treating a biological fluid, the system comprising:
  a treatment chamber for receiving a biological fluid;
  one or more sensors configured to detect light in the treatment chamber; and
  a first array of light sources positioned to illuminate the biological fluid in the treatment chamber, wherein the first array of light sources comprises a first light source channel configured to emit ultraviolet light with a first peak wavelength and a second light source channel configured to emit light with a second peak wavelength, wherein the second peak wavelength differs from the first peak wavelength by at least 5 nanometers.

Embodiment 2. The system of embodiment 1, wherein the first array of light sources comprises a plurality of light source clusters, wherein each light source cluster of the first array of light sources comprises a first light source of the first light source channel configured to emit ultraviolet light with the first peak wavelength and a second light source of the second light source channel configured to emit light with the second peak wavelength.

Embodiment 3. The system of embodiment 1 or embodiment 2, wherein the second light source channel is configured to emit ultraviolet light.

Embodiment 4. The system of any one of embodiments 1-3, wherein the first peak wavelength is in an ultraviolet A spectrum.

Embodiment 5. The system of any one of embodiments 1-4, wherein the first peak wavelength is in an ultraviolet A spectrum and the second peak wavelength is in an ultraviolet C spectrum.

Embodiment 6. The system of any one of embodiments 1-5, wherein the first light source channel and the second light source channel comprise LEDs.

Embodiment 7. The system of any one of embodiments 1-6, wherein the light intensity at 50% of the maximum peak intensity of light emitted by the first light source channel is within a spectral width of less than 20 nanometers of the first peak wavelength.

Embodiment 8. The system of any one of embodiments 1-6, wherein the full-width half-maximum (FWHM) spectral width of light emitted by the first light source channel is within 20 nanometers of the first peak wavelength.

Embodiment 9. The system of any one of embodiments 1-8, further comprising a first platform positioned in the treatment chamber, the first platform configured to carry the biological fluid.

Embodiment 10. The system of any one of embodiments 1-9, wherein the light sources of the first array of light sources are positioned in a non-uniform distribution on the array.

Embodiment 11. The system of embodiment 10, wherein the first array comprises a continuous inner region containing the midpoint of the first array and a continuous outer region surrounding the inner region, wherein the inner region occupies less than 50% of the surface area of the first array, and wherein the outer region occupies a remaining percentage of the surface area of the first array.

Embodiment 12. The system of embodiment 11, wherein a first density of light sources positioned in the outer region is greater than a second density of light sources positioned in the inner region.

Embodiment 13. The system of any one of embodiments 1-10, wherein the first array comprises a first region of light sources configured to illuminate a first biological fluid in the treatment chamber, and a second region of light sources configured to illuminate a second biological fluid in the treatment chamber.

Embodiment 14. The system of any one of embodiments 1-13, wherein the first array is configured such that the light sources illuminate the biological fluid in the treatment chamber with less than 25% variance in irradiance across a surface of the biological fluid facing the first array.

Embodiment 15. The system of any one of embodiments 1-14, wherein the first array of light sources further comprises a third light source channel configured to emit light of a third peak wavelength.

Embodiment 16. The system of any one of embodiments 1-15, wherein the first array of light sources further comprises a third light source channel configured to emit light of a third peak wavelength and a fourth light source channel configured to emit light of a fourth peak wavelength.

Embodiment 17. The system of any one of embodiments 1-16, further comprising a barrier positioned in the treatment chamber between the first array of light sources and the biological fluid.

Embodiment 18. The system of embodiment 17, wherein the barrier is transparent to light with a wavelength within 30 nm of the first peak wavelength.

Embodiment 19. The system of any one of embodiments 9-18, wherein the first platform and the first array of light sources are configured to translate relative to each other to vary a distance between the first array of light sources and the first platform.

Embodiment 20. The system of any one of embodiments 9-19, wherein the first platform is configured to separately hold at least a first container with a first biological fluid and a second container with a second biological fluid.

Embodiment 21. The system of any one of embodiments 9-20, wherein the first platform is slidably moveable for introducing and removing the biological fluid to and from the treatment chamber.

Embodiment 22. The system of any one of embodiments 1-21, wherein the system is configured to agitate the biological fluid during treatment.

Embodiment 23. The system of any one of embodiments 1-22, further comprising one or more sensors for detecting the presence of a biological fluid within the treatment chamber.

Embodiment 24. The system of any one of embodiments 1-23, further comprising a second array of light sources facing an opposite direction as the first array of light sources, wherein the second array of light sources comprises a third light source channel configured to emit light with the first peak wavelength and a fourth light source channel configured to emit light with the second peak wavelength.

Embodiment 25. The system of embodiment 24, wherein the first array of light sources and the second array of light sources are configured to translate relative to each other to vary a distance between the first array of light sources and the second array of light sources.

Embodiment 26. The system of embodiment 24 or embodiment 25, further comprising a first platform positioned in the treatment chamber between the first array of light sources and the second array of light sources, the first platform configured to carry the biological fluid.

Embodiment 27. The system of any one of embodiments 1-23, further comprising a second array of light sources facing a same direction as the first array of light sources, wherein the second array of light sources comprises a third light source channel configured to emit light with the first peak wavelength and a fourth light source channel configured to emit light with the second peak wavelength, and wherein the first array of light sources and the second array of light sources define a first region between the first array of light sources and the second array of light sources.

Embodiment 28. The system of embodiment 27, further comprising:
  a first platform positioned in the treatment chamber in the first region, the first platform configured to carry a first biological fluid; and
  a second platform positioned in the treatment chamber outside the first region, the second platform configured to carry a second biological fluid, wherein the second array of light sources faces the second platform.

Embodiment 29. The system of any one of embodiments 1-28, further comprising control circuitry.

Embodiment 30. The system of embodiment 29, wherein the control circuitry is configured to adjust or set an intensity of each light source of the first array of light sources.

Embodiment 31. The system of embodiment 29 or 30, wherein the control circuitry is configured to adjust or set a first intensity of light emitted by each first light source channel and to adjust or set a second intensity of light emitted by each second light source channel.

Embodiment 32. The system of any one of embodiments 29-31, wherein the control circuitry is configured to adjust or set a duration of emission of light from each light source of the first array of light sources.

Embodiment 33. The system of any one of embodiments 29-32, wherein the control circuitry is configured to adjust or set a first duration of emission of light from each first light source channel and to adjust or set a second duration of emission of light from each second light source channel.

Embodiment 34. The system of any one of embodiments 29-33, wherein the control circuitry is configured to adjust or set a duration of emission of light from each light source of the first array of light sources based at least in part on a first set of parameters detected by at least one sensor of the one or more sensors configured to detect light.

Embodiment 35. The system of any one of embodiments 29-34, wherein the control circuitry is configured to adjust or set an intensity of emission of light from each light source of the first array of light sources based at least in part on a first set of parameters detected by at least one sensor of the one or more sensors configured to detect light.

Embodiment 36. A system for treating a biological fluid, the system comprising:
a treatment chamber for receiving a biological fluid;
one or more sensors configured to detect light in the treatment chamber; and
a first array of light sources positioned to illuminate the biological fluid in the treatment chamber, wherein the first array of light sources comprises a first light source channel configured to emit ultraviolet light with a first peak wavelength in an ultraviolet A spectrum, wherein the full-width half-maximum (FWHM) spectral bandwidth of light emitted by the first light source channel is less than 20 nanometers.

Embodiment 37. The system of embodiment 36, wherein the first array of light sources comprises a first light source channel configured to emit ultraviolet light with a first peak wavelength between about 330 nm and about 350 nm.

Embodiment 38. The system of embodiment 36 or embodiment 37, wherein 50% of the maximum peak intensity of light emitted by the first light source channel is within 10 nanometers of the first peak wavelength Embodiment 39. The system of embodiment 36 or 37, wherein the light intensity at 50% of the maximum peak intensity of light emitted by the first light source channel is within a spectral width less than 20 nanometers.

Embodiment 40. The system of any one of embodiments 36-39, wherein the first array of light sources further comprises a second light source channel configured to emit light with a second peak wavelength.

Embodiment 41. The system of embodiment 40, wherein the second peak wavelength differs from the first peak wavelength by at least 5 nanometers.

Embodiment 42. The system of embodiment 40 or embodiment 41, wherein the second peak wavelength is in an ultraviolet A spectrum.

Embodiment 43. The system of embodiment 40 or embodiment 41, wherein the second peak wavelength is in an ultraviolet B spectrum.

Embodiment 44. The system of embodiment 40 or embodiment 41, wherein the second peak wavelength is in an ultraviolet C spectrum.

Embodiment 45. The system of any one of embodiments 40-44, wherein 50% of the maximum peak intensity of light emitted by the second light source channel is within 10 nanometers of the second peak wavelength.

Embodiment 46. The system of any one of embodiments 40-44, wherein the full-width half-maximum (FWHM) spectral bandwidth of light emitted by the second light source channel is less than 20 nanometers.

Embodiment 47. The system of any one of embodiments 40-46, wherein the first array of light sources comprises a plurality of light source clusters, and wherein each light source cluster of the first array of light sources comprises a first light source of the first light source channel configured to emit ultraviolet light with the first peak wavelength and a second light source of the second light source channel configured to emit light with a second peak wavelength.

Embodiment 48. The system of any one of embodiments 36-47, wherein the first light source channel comprises one or more LEDs.

Embodiment 49. The system of any one of embodiments 40-48, wherein the second light source channel comprises one or more LEDs.

Embodiment 50. The system of any one of embodiments 36-49, further comprising a first platform positioned in the treatment chamber, the first platform configured to carry the biological fluid.

Embodiment 51. The system of any one of embodiments 36-50, wherein the light sources of the first array of light sources are positioned in a non-uniform distribution on the array.

Embodiment 52. The system of embodiment 51, wherein the first array comprises a continuous inner region containing the midpoint of the first array and a continuous outer region surrounding the inner region, wherein the inner region occupies less than 50% of the surface area of the first array, and wherein the outer region occupies a remaining percentage of the surface area of the first array.

Embodiment 53. The system of embodiment 52, wherein a first density of light sources positioned in the outer region is greater than a second density of light sources positioned in the inner region.

Embodiment 54. The system of any one of embodiments 36-51, wherein the first array comprises a first region of light sources configured to illuminate a first biological fluid in the treatment chamber, and a second region of light sources configured to illuminate a second biological fluid in the treatment chamber.

Embodiment 55. The system of any one of embodiments 36-54, wherein the first array is configured such that the light sources illuminate the biological fluid in the treatment chamber with less than 25% variance in irradiance across a surface of the biological fluid facing the first array.

Embodiment 56. The system of any one of embodiments 40-55, wherein the first array of light sources further comprises a third light source channel configured to emit light of a third peak wavelength.

Embodiment 57. The system of any one of embodiments 40-56, wherein the first array of light sources further comprises a third light source channel configured to emit light of a third peak wavelength and a fourth light source channel configured to emit light of a fourth peak wavelength.

Embodiment 58. The system of any one of embodiments 36-57, further comprising a barrier positioned in the treatment chamber between the first array of light sources and the biological fluid.

Embodiment 59. The system of embodiment 58, wherein the barrier is transparent to light with a wavelength within 30 nm of the first peak wavelength.

Embodiment 60. The system of any one of embodiments 50-59, wherein the first platform and the first array of light sources are configured to translate relative to each other to vary a distance between the first array of light sources and the first platform.

Embodiment 61. The system of any one of embodiments 50-60, wherein the first platform is configured to separately hold at least a first container with a first biological fluid and a second container with a second biological fluid.

Embodiment 62. The system of any one of embodiments 50-61, wherein the first platform is slidably moveable for introducing and removing the biological fluid into and out of the treatment chamber.

Embodiment 63. The system of any one of embodiments 36-62, wherein the system is configured to agitate the biological fluid during treatment.

Embodiment 64. The system of any one of embodiments 36-63, further comprising one or more sensors for detecting the presence of a biological fluid within the treatment chamber.

Embodiment 65. The system of any one of embodiments 36-64, further comprising a second array of light sources facing an opposite direction as the first array of light sources, wherein the second array of light sources comprises a second light source channel configured to emit light of the first peak wavelength in the ultraviolet A spectrum.

Embodiment 66. The system of any one of embodiments 36-65, further comprising a second array of light sources facing an opposite direction as the first array of light sources, wherein the second array of light sources comprises a second light source channel configured to emit light of a second peak wavelength, wherein the second peak wavelength differs from the first peak wavelength by at least 5 nanometers.

Embodiment 67. The system of embodiment 65 or embodiment 66, wherein 50% of the maximum peak intensity of light emitted by the second light source channel is within 10 nanometers of the first peak wavelength.

Embodiment 68. The system of embodiment 65 or embodiment 66, wherein the full-width half-maximum (FWHM) spectral bandwidth of light emitted by the second light source channel is less than 20 nanometers.

Embodiment 69. The system of any one of embodiments 65-68, wherein the first array of light sources and the second array of light sources are configured to translate relative to each other to vary a distance between the first array of light sources and the second array of light sources.

Embodiment 70. The system of any one of embodiments 65-69, further comprising a first platform positioned in the treatment chamber between the first array of light sources and the second array of light sources, the first platform configured to carry the biological fluid.

Embodiment 71. The system of any one of embodiments 36-64, further comprising a second array of light sources facing a same direction as the first array of light sources, wherein the second array of light sources comprises a second light source channel configured to emit ultraviolet light of the first peak wavelength in the ultraviolet A spectrum, and wherein the first array of light sources and the second array of light sources define a first region between the first array of light sources and the second array of light sources.

Embodiment 72. The system of embodiment 71, wherein 50% of the maximum peak intensity of light emitted by the second source channel is within 10 nanometers of the first peak wavelength.

Embodiment 73. The system of embodiment 71, wherein the full-width half-maximum (FWHM) spectral bandwidth of light emitted by the second light source channel is less than 20 nanometers.

Embodiment 74. The system of any one of embodiments 71-73, further comprising:
a first platform positioned in the treatment chamber in the first region, the first platform configured to carry a first biological fluid; and
a second platform positioned in the treatment chamber outside the first region, the second platform configured to carry a second biological fluid, wherein the second array of light sources faces the second platform.

Embodiment 75. The system of any one of embodiments 36-74, further comprising control circuitry.

Embodiment 76. The system of embodiment 75, wherein the control circuitry is configured to adjust or set an intensity of each light source of the first array of light sources.

Embodiment 77. The system of embodiment 75 or embodiment 76, wherein the control circuitry is configured to adjust or set a duration of emission of light from each light source of the first array of light sources.

Embodiment 78. The system of any one of embodiments 75-77, wherein the control circuitry is configured to adjust or set a duration of emission of light from each of light source of the first array of light sources based at least in part on a first set of parameters detected by at least one sensor of the one or more sensors configured to detect light.

Embodiment 79. The system of any one of embodiments 75-78, wherein the control circuitry is configured to adjust or set an intensity of each light source of the first array of light sources based at least in part on a first set of parameters detected by at least one sensor of the one or more sensors configured to detect light.

Embodiment 80. A method for treating a biological fluid, the method comprising:
providing a biological fluid in admixture with a pathogen inactivation compound;
illuminating the biological fluid with ultraviolet light of a first peak wavelength; and
illuminating the biological fluid with light of a second peak wavelength, wherein the first peak wavelength differs from the second peak wavelength by at least 5 nm, wherein illuminating the biological fluid occurs for a duration and at an intensity sufficient to inactivate a pathogen in the biological fluid.

Embodiment 81. The method of embodiment 80, wherein the ultraviolet light of a first peak wavelength is provided by a first light source and wherein the light of the second peak wavelength is provided by a second light source.

Embodiment 82. The method of embodiment 81, wherein 50% of the maximum peak intensity of light emitted by the first light source is within 10 nanometers of the first peak wavelength.

Embodiment 83. The method of embodiment 81, wherein the full-width half-maximum (FWHM) spectral bandwidth of light emitted by the first light source is less than 20 nanometers.

Embodiment 84. The method of any one of embodiments 80-83, wherein the ultraviolet light of the first peak wavelength is in an ultraviolet A spectrum.

Embodiment 85. The method of any one of embodiments 80-84, wherein the light of the second peak wavelength is in an ultraviolet B spectrum, an ultraviolet C spectrum, or a visible light spectrum.

Embodiment 86. The method of any one of embodiments 80-85, wherein illuminating the biological fluid with ultraviolet light of the first peak wavelength and illuminating the biological fluid with light of the second peak wavelength occurs sequentially.

Embodiment 87. The method of any one of embodiments 80-86, wherein illuminating the biological fluid with ultraviolet light of the first peak wavelength includes illuminating the biological fluid with ultraviolet light of the first peak wavelength for a first duration and wherein illuminating the biological fluid with light of the second peak wavelength includes illuminating the biological fluid with light of the second peak wavelength for a second duration.

Embodiment 88. The method of embodiment 87, wherein the first duration is different from the second duration.

Embodiment 89. The method of any one of embodiments 80-88, wherein illuminating the biological fluid with ultraviolet light of the first peak wavelength is performed by a first set of light sources, wherein illuminating the biological fluid with light of the second peak wavelength is performed by a second set of light sources, and wherein the first and the second set of light sources are disposed on an array of light source clusters.

Embodiment 90. The method of any one of embodiments 80-89, wherein first light source and the second light source comprise LEDs.

Embodiment 91. The method of any one of embodiments 80-90, wherein the pathogen inactivation compound is a photoactive pathogen inactivating compound selected from the group consisting of a psoralen, an isoalloxazine, an alloxazine, a phthalocyanine, a phenothiazine, a porphyrin, and merocyanine 540.

Embodiment 92. The method of embodiment 91, wherein the pathogen inactivation compound is a psoralen.

Embodiment 93. A method for treating a biological fluid comprising:
providing a biological fluid in admixture with a pathogen inactivation compound; and
illuminating the biological fluid with ultraviolet light of a first peak wavelength provided by a first ultraviolet light source, wherein the full-width half-maximum (FWHM) spectral bandwidth of the ultraviolet light emitted by the first ultraviolet light source is less than 20 nanometers, and
wherein illuminating the biological fluid occurs for a duration and at an intensity sufficient to inactivate a pathogen in the biological fluid.

Embodiment 94. The method of embodiment 93, wherein the ultraviolet light of the first peak wavelength is in an ultraviolet A spectrum.

Embodiment 95. The method of embodiment 94, wherein the first peak wavelength is between 330 nanometers and 350 nanometers.

Embodiment 96. The method of any one of embodiments 93-95, wherein the first light source comprises an LED.

Embodiment 97. The method of any one of embodiments 93-96, wherein the biological fluid is within a container and wherein illuminating the biological fluid with ultraviolet light of the first peak wavelength is performed by a first set of light sources disposed on an array of light sources, the first set of light sources facing only one side of the container.

Embodiment 98. The method of any one of embodiments 93-97, wherein the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540.

Embodiment 99. The method of embodiment 98, wherein the pathogen inactivation compound is a psoralen.

Embodiment 100. A method for treating a biological fluid, comprising:
introducing a biological fluid in admixture with a pathogen inactivating compound into a treatment chamber, the treatment chamber comprising, one or more light sensors configured to detect light in the treatment chamber and a first array of light sources configured to illuminate the biological fluid in the treatment chamber, wherein the first array of light sources comprises a first light source channel configured to emit ultraviolet light with a first peak wavelength and a second light source channel configured to emit light with a second peak wavelength, the first peak wavelength differing from the second peak wavelength by at least 5 nanometers; and
illuminating the biological fluid by emitting light with the first peak wavelength from the first light source channel and emitting light with the second peak wavelength from the second light source channel for a duration and at an intensity sufficient to inactivate a pathogen in the biological fluid.

Embodiment 101. The method of embodiment 100, further comprising
determining a set of characteristics of the biological fluid;
determining a treatment profile based on the set of characteristics of the biological fluid; and
adjusting or setting a set of parameters of the treatment chamber in accordance with the treatment profile.

Embodiment 102. The method of embodiment 100 or embodiment 101, wherein illuminating the biological fluid is performed in accordance with the treatment profile.

Embodiment 103. The method of any one of embodiments 100-102, wherein the duration and the intensity sufficient to inactivate the pathogen is determined from the treatment profile.

Embodiment 104. The method of any one of embodiments 100-103, wherein the first array of light sources comprises a plurality of light source clusters, wherein each light source cluster of the first array of light sources comprises a first light source of the first light source channel configured to emit ultraviolet light with the first peak wavelength and a second light source of the second light source channel configured to emit light with the second peak wavelength.

Embodiment 105. The method of any one of embodiments 100-104, wherein 50% of the maximum peak intensity of light emitted by the first light source channel is within 10 nanometers of the first peak wavelength.

Embodiment 106. The method of any one of embodiments 100-104, wherein the full-width half-maximum (FWHM) spectral bandwidth of light emitted by the first light source channel is less than 20 nanometers.

Embodiment 107. The method of any one of embodiments 100-106, wherein the set of characteristics of the biological fluid includes at least one of: a volume of the biological fluid, a type of the biological fluid, or a temperature of the biological fluid.

Embodiment 108. The method of any one of embodiments 100-107, wherein determining the treatment profile based on the set of characteristics comprises determining the first peak wavelength and the second peak wavelength.

Embodiment 109. The method of any one of embodiments 100-108, wherein determining the treatment profile based on the set of characteristics comprises determining a first intensity of ultraviolet light with the first peak wavelength and a second intensity of light with the second peak wavelength.

Embodiment 110. The method of any one of embodiments 100-109, wherein determining the treatment profile based on the set of characteristics comprises determining a first duration of emission of ultraviolet light with the first peak wavelength and a second duration of emission of light with the second peak wavelength.

Embodiment 111. The method of any one of embodiments 100-110, the treatment chamber further comprising a first platform positioned in the treatment chamber, the first platform carrying the biological fluid.

Embodiment 112. The method of embodiment 111, wherein adjusting or setting the set of parameters of the treatment chamber comprises adjusting or setting a distance between the first array of light sources and the first platform.

Embodiment 113. The method of any one of embodiments 100-112, further comprising agitating the biological fluid.

Embodiment 114. The method of embodiment 113, wherein adjusting or setting the set of parameters of the treatment chamber comprises adjusting or setting a parameter associated with agitation of the biological fluid.

Embodiment 115. A method for treating a biological fluid, comprising:

introducing the biological fluid in admixture with a pathogen inactivation compound into a treatment chamber, the treatment chamber comprising one or more light sensors configured to detect light in the treatment chamber and a first array of light sources configured to illuminate the biological fluid in the treatment chamber, wherein the first array of light sources comprises a first light source channel configured to emit ultraviolet light with a first peak wavelength in the ultraviolet A spectrum wherein the full-width half-maximum (FWHM) spectral bandwidth of light emitted by the first light source channel is less than 20 nanometers; and illuminating the biological fluid by emitting light with the first peak wavelength from the first light source channel for a first duration and at first intensity sufficient to inactivate a pathogen in the biological fluid.

Embodiment 116. The method of embodiment 115, wherein each light source of the first light source channel is configured to emit ultraviolet light with a first peak wavelength between about 330 nm and about 350 nm.

Embodiment 117. The method of embodiment 115 or embodiment 116, further comprising, determining a set of characteristics of the biological fluid;

determining a treatment profile based on the set of characteristics of the biological fluid; and adjusting or setting a set of parameters of the treatment chamber in accordance with the treatment profile.

Embodiment 118. The method of embodiment 117, wherein illuminating the biological fluid is performed in accordance with the treatment profile.

Embodiment 119. The method of embodiment 117 or embodiment 118, wherein the first duration and the first intensity sufficient to inactivate the pathogen is determined from the treatment profile.

Embodiment 120. The method of any one of embodiments 115-119, wherein 50% of the maximum peak intensity of light emitted by the first light source channel is within 20 nanometers of the first peak wavelength.

Embodiment 121. The method of any one of embodiments 115-120, wherein the first array of light sources comprises a second light source channel configured to emit light of a second peak wavelength.

Embodiment 122. The method of embodiment 121, wherein the second peak wavelength differs from first peak wavelength by at least 5 nm Embodiment 123. The method of embodiment 121 or embodiment 122, wherein 50% of the maximum peak intensity of light emitted by the second light source channel is within 10 nanometers of the second peak wavelength.

Embodiment 124. The method of embodiment 121 or embodiment 122, wherein a full-width half-maximum (FWHM) spectral bandwidth of light emitted by the second light source channel is less than 20 nanometers.

Embodiment 125. The method of any one of embodiments 121-124, wherein the first array of light sources comprises a plurality of light source clusters, and wherein each light source cluster of the first array of light sources comprises a first light source of the first light source channel configured to emit ultraviolet light with the first peak wavelength and a second light source of the second light source channel configured to emit ultraviolet light with the second peak wavelength.

Embodiment 126. The method of any one of embodiments 117-125, wherein the set of characteristics of the biological fluid includes at least one of: a volume of the biological fluid, a type of the biological fluid, or a temperature of the biological fluid.

Embodiment 127. The method of any one of embodiments 117-126, wherein determining the treatment profile based on the set of characteristics comprises determining the first peak wavelength.

Embodiment 128. The method of any one of embodiments 117-127, wherein determining the treatment profile based on the set of characteristics comprises determining the first intensity of light with the first peak wavelength.

Embodiment 129. The method of any one of embodiments 117-128, wherein determining the treatment profile based on the set of characteristics comprises determining the first duration of emission of light with the first peak wavelength.

Embodiment 130. The method of any one of embodiments 115-129, the treatment chamber further comprising a first platform positioned in the treatment chamber, the first platform carrying the biological fluid.

Embodiment 131. The method of embodiment 130, wherein adjusting or setting the set of parameters of the treatment chamber comprises adjusting or setting a distance between the first array of light sources and the first platform.

Embodiment 132. The method of any one of embodiments 115-131, further comprising agitating the biological fluid.

Embodiment 133. The method of embodiment 132, wherein adjusting or setting the set of parameters of the treatment chamber comprises adjusting or setting a parameter associated with agitation of the biological fluid.

Embodiment 134. The method of any one of embodiments 80-133, wherein the treating is sufficient to inactivate at least 1 log of a pathogen in the biological fluid, and wherein the biological fluid after illuminating is suitable for infusion into a subject without further processing to remove residual pathogen inactivation compound or photoproducts thereof.

Embodiment 135. The method of any one of embodiments 80-133, wherein the treating is sufficient to inactivate at least 1 log of a pathogen in the biological fluid, and wherein the biological fluid comprises 5 µM or less of pathogen inactivation compound after illuminating.

Embodiment 136. The method of embodiment 134 or embodiment 135, wherein the concentration of pathogen inactivation compound in admixture with the biological fluid prior to illumination is at least 10 µM.

Embodiment 137. The method of any one of embodiments 134-136, wherein the concentration of pathogen inactivation compound in admixture with the biological fluid after illuminating is at least 3-fold less than the concentration of pathogen inactivation compound in admixture with the biological fluid prior to illuminating.

Embodiment 138. A pathogen inactivated biological fluid prepared by the methods of any one of embodiments 80-137.

Embodiment 139. The pathogen inactivated biological fluid of embodiment 138, wherein the biological fluid comprises 5 µM or less of pathogen inactivation compound after illuminating.

What is claimed is:

1. A method for treating a biological fluid comprising:

providing a biological fluid in admixture with a photoactive pathogen inactivation compound; and illuminating the biological fluid with ultraviolet light with a first peak wavelength of from about 315 nm to about 350 nm emitted by a set of one or more first light sources, wherein each of the one or more first light sources emits light has a full-width half-maximum (FWHM) spectral bandwidth of less than 20 nanometers, and wherein illuminating the biological fluid occurs for a duration and at an intensity sufficient to inactivate a pathogen in the biological fluid when present.

2. The method of claim 1, wherein the first peak wavelength is from about 315 to about 335 nm.

3. The method of claim 1, wherein the first peak wavelength is from about 330 nm to about 350 nm.

4. The method of claim 1, wherein the first peak wavelength is a peak wavelength of one first light source of the set of one or more first light sources.

5. The method of claim 4, wherein the first peak wavelength is a peak wavelength of each of a plurality of first light sources of the set of one or more first light sources.

6. The method of claim 1, wherein the first peak wavelength is an average peak wavelength of the set of one or more first light sources.

7. The method of claim 1, further comprising illuminating the biological fluid with ultraviolet light with a second peak wavelength emitted by a set of one or more second light sources, wherein each of the one or more second light sources emits light has a full-width half-maximum (FWHM) spectral bandwidth of less than 20 nanometers, and wherein the second peak wavelength differs from first peak wavelength by at least 5 nm.

8. The method of claim 7, wherein the second peak wavelength is a peak wavelength of one second light source of the set of one or more second light sources.

9. The method of claim 8, wherein the second peak wavelength is a peak wavelength of each of a plurality of second light sources of the set of one or more second light sources.

10. The method of claim 7, wherein the second peak wavelength is an average peak wavelength of the set of one or more second light sources.

11. The method of claim 1, wherein the set of one or more first light sources comprises one or more LEDs.

12. The method of claim 1, wherein the biological fluid is contained within a container, and wherein the set of one or more first light sources is disposed as an array of light sources, the set of one or more first light sources facing only one side of the container.

13. The method of claim 1, wherein the photoactive pathogen inactivation compound is a psoralen.

14. The method of claim 13, wherein the photoactive pathogen inactivation compound is amotosalen.

15. The method of claim 1, further comprising, prior to illuminating the biological fluid with the ultraviolet light with the first peak wavelength:

introducing the biological fluid in admixture with the photoactive pathogen inactivation compound into a treatment chamber, the treatment chamber comprising one or more light sensors configured to detect light in the treatment chamber and a first array of light sources configured to illuminate the biological fluid in the treatment chamber, wherein the first array of light sources comprises a first light source channel comprising the set of one or more first light sources, wherein illuminating the biological fluid comprises emitting light with the first peak wavelength from the first light source channel for a first duration and at a first intensity sufficient to inactivate a pathogen in the biological fluid when present.

16. The method of claim 15, wherein each light source of the first light source channel is configured to emit ultraviolet light with a first peak wavelength between about 315 nm and about 350 nm.

17. The method of claim 15, further comprising, determining a set of characteristics of the biological fluid; determining a treatment profile based on the set of characteristics of the biological fluid; and
adjusting or setting a set of parameters of the treatment chamber in accordance with the treatment profile.

18. The method of claim 17, wherein illuminating the biological fluid is performed in accordance with the treatment profile, and wherein the first duration and the first intensity sufficient to inactivate the pathogen are determined from the treatment profile.

19. The method of claim 15, wherein the first array of light sources comprises a second light source channel configured to emit light of a second peak wavelength.

20. The method of claim 19, wherein the second peak wavelength differs from the first peak wavelength by at least 5 nm.

21. The method of claim 19, wherein the second peak wavelength is in an ultraviolet A, ultraviolet B, or ultraviolet C spectrum.

22. The method of claim 19, wherein the second light source channel comprises a set of one or more second light sources, wherein each of the one or more second light sources emits light having a full-width half-maximum (FWHM) spectral bandwidth of less than 20 nanometers.

23. The method of claim 17, wherein the set of characteristics of the biological fluid includes one or more of a group comprising: a volume of the biological fluid, a type of the biological fluid, and a temperature of the biological fluid.

24. The method of claim 17, wherein determining the treatment profile based on the set of characteristics of the biological fluid comprises determining the first intensity of light with the first peak wavelength or determining the first duration of emission of light with the first peak wavelength.

25. The method of claim 15, wherein the treatment chamber further comprises a first platform positioned in the treatment chamber, the first platform carrying the biological fluid.

26. The method of claim 25, wherein adjusting or setting a set of parameters of the treatment chamber comprises adjusting or setting a distance between the first array of light sources and the first platform.

27. The method of claim 1, further comprising agitating the biological fluid.

28. The method of claim 1, wherein a total dose of the ultraviolet light illuminating the biological fluid is about 0.5 J/cm$^2$ to about 50 J/cm$^2$.

29. The method of claim 28, wherein the total dose of the ultraviolet light illuminating the biological fluid emitted by the set of one or more first light sources is about 0.5 J/cm$^2$ to about 50 J/cm$^2$.

30. The method of claim 1, wherein the method for treating is sufficient to inactivate at least 1 log of a pathogen in the biological fluid when present, and wherein the biological fluid after illuminating is suitable for infusion into a subject without further processing to remove residual pathogen inactivation compound or photoproduct(s) thereof.

31. The method of claim 1, wherein the method for treating is sufficient to inactivate at least 1 log of a pathogen in the biological fluid when present, and wherein the biological fluid after illuminating is suitable for infusion into a subject without subjecting the biological fluid to a compound removal step to remove residual pathogen inactivation compound or photoproduct(s) thereof.

32. The method of claim 1, wherein the method for treating is sufficient to inactivate at least 1 log of a pathogen in the biological fluid when present, and wherein the biological fluid comprises 5 µM or less of the photoactive pathogen inactivation compound after illuminating.

33. The method of claim 1, wherein the method for treating is sufficient to inactivate at least 1 log of a pathogen in the biological fluid when present, and wherein the biological fluid comprises 2 µM or less of the photoactive pathogen inactivation compound after illuminating.

34. The method of claim 1, wherein a concentration of the photoactive pathogen inactivation compound in admixture with the biological fluid prior to illuminating is at least about 10 µM or at least about 50 µM.

35. The method of claim 1, wherein a concentration of the photoactive pathogen inactivation compound in admixture with the biological fluid prior to illuminating is about 15 µM to about 150 µM.

36. The method of claim 1, wherein a concentration of the photoactive pathogen inactivation compound in admixture with the biological fluid after illuminating is at least 3-fold less than the concentration of the photoactive pathogen inactivation compound in admixture with the biological fluid prior to illuminating.

37. The method of claim 1, wherein the method for treating is sufficient to inactivate at least 4 log of a pathogen in the biological fluid when present.

38. The method of claim 1, wherein the biological fluid after illuminating maintains sufficient biological activity so that the biological fluid is suitable for infusion into a subject.

39. The method of claim 1, wherein the biological fluid comprises a blood product.

40. The method of claim 1, wherein the biological fluid comprises a plasma composition.

41. The method of claim 40, wherein a concentration of fibrinogen in the plasma composition after illuminating is at least 70% of the concentration of fibrinogen in the plasma composition prior to illuminating.

42. The method of claim 40, wherein a concentration of factor VIII in the plasma composition after illuminating is at least 70% of the concentration of factor VIII in the plasma composition prior to illuminating.

43. The method of claim 1, wherein the biological fluid comprises a platelet composition.

44. The method of claim 43, wherein the biological fluid further comprises a platelet additive solution.

45. The method of claim 43, wherein an amount of platelets in the platelet composition after illuminating is at least 80% platelet recovery.

46. The method of claim 43, wherein the pH at 22° C. of the platelet composition after illuminating is at least 6.2.

47. The method of claim 1, wherein the method comprises, prior to illuminating, incubating the biological fluid with the photoactive pathogen inactivation compound for a period of from 30 minutes to 24 hours.

48. The method of claim 3, wherein the first peak wavelength is from about 340 nm to about 350 nm.

49. The method of claim 3, wherein the first peak wavelength is 345±5 nm.

50. The method of claim 2, wherein the first peak wavelength is from about 320 to about 330 nm.

51. The method of claim 2, wherein the first peak wavelength is 325±5 nm.

52. The method of claim 7, wherein the set of one or more second light sources comprises one or more LEDs.

53. The method of claim 1, wherein the biological fluid is contained within a container, and wherein the set of one or more first light sources is disposed as a first array of light sources and a second array of light sources, the first array and the second array facing opposite sides of the container.

54. The method of claim 15, wherein the treatment chamber further comprises a second array of light sources configured to illuminate the biological fluid in the treatment chamber, wherein the second array of light sources comprises a first light source channel of the second array of light sources comprising a set of one or more second light sources configured to emit light of a first peak wavelength of the second array, wherein illuminating the biological fluid comprises emitting light with the first peak wavelength of each of the first array of light sources and second array of light sources, for a first duration and at first intensity sufficient to inactivate a pathogen in the biological fluid when present.

55. The method of claim 54, wherein the first peak wavelength of the second array of light sources is substantially the same as the first peak wavelength of the first array of light sources.

56. The method of claim 54, wherein the second array of light sources comprises a second light source channel of the second array of light sources configured to emit light of a second peak wavelength, and wherein the second peak wavelength of the second array of light sources is substantially the same as the second peak wavelength of the first array of light sources.

57. The method of claim 1, further comprising, prior to illuminating the biological fluid with the ultraviolet light with the first peak wavelength:
introducing the biological fluid in admixture with the photoactive pathogen inactivation compound into a system for treating the biological fluid, the system comprising:
a treatment chamber configured to receive the biological fluid;
one or more sensors configured to detect light in the treatment chamber;
a first array of light sources positioned to illuminate the biological fluid in the treatment chamber, wherein the first array of light sources comprises a first light source channel configured to emit ultraviolet light with a first peak wavelength of from about 315 nm to about 350 nm, and wherein the first light source channel comprises one or more light sources, each of which emits light having a full-width half-maximum (FWHM) spectral bandwidth of less than 20 nanometers; and
control circuitry, wherein the control circuitry comprises:
a memory;
one or more processors; and
one or more programs, wherein the one or more programs are stored in the memory and configured to be executed by the one or more processors, the one or more programs when executed by the one or more processors cause the processor to: illuminate the biological fluid in admixture with the photoactive pathogen inactivation compound by controlling the first array of light sources to illuminate light for a duration and at an intensity sufficient to inactivate a pathogen in the biological fluid when present; and
illuminating the biological fluid for the duration and at the intensity sufficient to inactivate the pathogen in the biological fluid when present.

\* \* \* \* \*